(12) United States Patent
Leclerc et al.

(10) Patent No.: US 8,383,643 B2
(45) Date of Patent: Feb. 26, 2013

(54) SPIRO COMPOUNDS USEFUL AS INHIBITORS OF STEAROYL-COENZYME A DELTA-9 DESATURASE

(75) Inventors: Jean-Philippe Leclerc, Laval (CA); Chun-Sing Li, Dollard-des-Ormeaux (CA); Oscar Miguel Moradei, Kirkland (CA)

(73) Assignee: Merck Canada Inc., Kirkland, Quebec (CA)

( * ) Notice: Subject to any disclaimer, the term of this patent is extended or adjusted under 35 U.S.C. 154(b) by 0 days.

(21) Appl. No.: 13/383,446

(22) PCT Filed: Jul. 21, 2010

(86) PCT No.: PCT/CA2010/001150
§ 371 (c)(1),
(2), (4) Date: Jan. 11, 2012

(87) PCT Pub. No.: WO2011/011872
PCT Pub. Date: Feb. 3, 2011

(65) Prior Publication Data
US 2012/0122912 A1 May 17, 2012

Related U.S. Application Data

(60) Provisional application No. 61/229,049, filed on Jul. 28, 2009.

(51) Int. Cl.
*A61K 31/438* (2006.01)
*C07D 491/107* (2006.01)

(52) U.S. Cl. .......................................... 514/278; 546/17

(58) Field of Classification Search .................. None
See application file for complete search history.

(56) References Cited

U.S. PATENT DOCUMENTS

| | | | |
|---|---|---|---|
| 2008/0182838 A1 | 7/2008 | Leblanc et al. | |
| 2009/0325956 A1 | 12/2009 | Taniguchi et al. | |
| 2010/0069351 A1 | 3/2010 | Taniguchi et al. | |

FOREIGN PATENT DOCUMENTS

| | | | |
|---|---|---|---|
| WO | 2005/011653 | A2 | 2/2005 |
| WO | 2005/011654 | A2 | 2/2005 |
| WO | 2005/011655 | A2 | 2/2005 |
| WO | 2005/011656 | A2 | 2/2005 |
| WO | 2005/011657 | A2 | 2/2005 |
| WO | 2006/014168 | A1 | 2/2006 |
| WO | 2006/034279 | A1 | 3/2006 |
| WO | 2006/034312 | A1 | 3/2006 |
| WO | 2006/034315 | A2 | 3/2006 |
| WO | 2006/034338 | A1 | 3/2006 |
| WO | 2006/034341 | A2 | 3/2006 |
| WO | 2006/034440 | A2 | 3/2006 |
| WO | 2006/034441 | A1 | 3/2006 |
| WO | 2006/034446 | A2 | 3/2006 |
| WO | 2006/086445 | A2 | 8/2006 |
| WO | 2006/086447 | A2 | 8/2006 |
| WO | 2006/101521 | A2 | 9/2006 |
| WO | 2006/125178 | A2 | 11/2006 |
| WO | 2006/125179 | A1 | 11/2006 |
| WO | 2006/125180 | A1 | 11/2006 |
| WO | 2006/125181 | A2 | 11/2006 |
| WO | 2006/125194 | A2 | 11/2006 |
| WO | 2006/130986 | A1 | 12/2006 |
| WO | 2007/009236 | A1 | 1/2007 |
| WO | 2007/044085 | A2 | 4/2007 |
| WO | 2007/046867 | A2 | 4/2007 |
| WO | 2007/046868 | A2 | 4/2007 |
| WO | 2007/050124 | A1 | 5/2007 |
| WO | 2007/056846 | A1 | 5/2007 |
| WO | 2007/071023 | A1 | 6/2007 |
| WO | 2007/130075 | A1 | 11/2007 |
| WO | 2007/134457 | A1 | 11/2007 |
| WO | 2007/136746 | A2 | 11/2007 |
| WO | 2007/143697 | A2 | 12/2007 |
| WO | 2007/143823 | A1 | 12/2007 |
| WO | 2007/143824 | A1 | 12/2007 |
| WO | 2008/003753 | A1 | 1/2008 |
| WO | 2008/017161 | A1 | 2/2008 |
| WO | 2008/024390 | A2 | 2/2008 |
| WO | 2008/029266 | A1 | 3/2008 |
| WO | 2008/036715 | A1 | 3/2008 |
| WO | 2008/044767 | A1 | 4/2008 |
| WO | 2008/046226 | A1 | 4/2008 |
| WO | 2008/056687 | A1 | 5/2008 |
| WO | 2008/062276 | A2 | 5/2008 |
| WO | 2008/064474 | A1 | 6/2008 |
| WO | 2008/074824 | A2 | 6/2008 |
| WO | 2008/074835 | A1 | 6/2008 |
| WO | 2008/096746 | A1 | 8/2008 |
| WO | 2008/127349 | A2 | 10/2008 |

OTHER PUBLICATIONS

A. D. Attie, et al., Journal of Lipid Research, vol. 43, pp. 1899 (2002).

(Continued)

*Primary Examiner* — Joseph K. McKane
*Assistant Examiner* — Alicia L Otton
(74) *Attorney, Agent, or Firm* — Kenrick L. Vidale; John C. Todaro

(57) ABSTRACT

Heteroaromatic compounds of structural formula (I) are selective inhibitors of stearoyl-coenzyme A delta-9 desaturase (SCD1) relative to other known stearoyl-coenzyme A desaturases. The compounds of the present invention are useful for the prevention and treatment of conditions related to abnormal lipid synthesis and metabolism, including cardiovascular disease, such as atherosclerosis; obesity; diabetes; neurological disease; metabolic syndrome; insulin resistance; and liver steatosis.

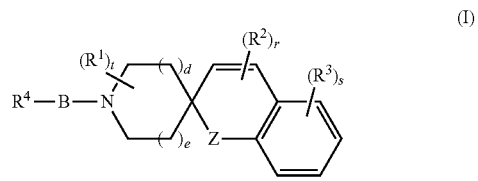

(I)

17 Claims, No Drawings

OTHER PUBLICATIONS

B. Behrouzian, et al., Prostaglandins, Leukotrienes and Essential Fatty Acids, vol. 68, pp. 107-112 (2003).
S. Beiraghi, et al., Gene, vol. 309, pp. 11-12 (2003).
P. Cohen, et al., Science, vol. 297, pp. 240 (2002).
A. Dobrzyn, et al., Obesity Reviews, vol. 6, pp. 169-174 (2005).
K. Donnelly, et al., The Journal of Clinical Investigation, vol. 115, No. 5, pp. 1343 (2005).
G. Jiang, et al., The Journal of Clinical Investigation, vol. 115, No. 4, pp. 1030-1038 (2005).
G. Liu, et al., J. Medicinal Chemistry, vol. 50, pp. 3086-3100 (2007).
M. MacDonald, et al., Journal of Lipid Research, vol. 49, pp. 217 (2008).
I. Marques-Lopes, et at., Am. J. Clinical Nutr., vol. 73, pp. 253-261 (2001).
K. Mihara, J. Biochem., vol. 108, p. 1022 (1990)—abstract.
M. Miyazaki, et al., Prostaglandins, Leukotrienes and Essential Fatty Acids, vol. 68, pp. 113-121 (2003).
M. Miyazaki, et al., The Journal of Biological Chemistry, vol. 278, No. 36, pp. 33904-33911 (2003).
S. Morgan-Lappe, et al., Cancer Research, vol. 67, No. 9, pp. 4390 (2007).
J. Ntambi, et al., PNAS, vol. 99, No. 17, pp. 11482-11486 (2002).
N. Oshino, Archives of Biochemistry and Biophysics, vol. 149, pp. 378-387 (1972).
Y. Park, et al., Biochemica et Biophysica Acta, vol. 1486, pp. 285-292 (2000).
P.K. Raju, et al., The Journal of Biological Chemistry, vol. 242, No. 3, pp. 379-384 (1967).
N. Scaglia, et al., The Journal of Biological Chemistry, vol. 280, No. 27, pp. 25339-25349 (2005).
P. Sjogren, et al., Diabetologia, vol. 51, pp. 328-335 (2008).
P. Strittmatter, et al., Proc. Nat. Acad. Sci. USA, vol. 71, No. 11, pp. 4565-4569 (1974).
M. A. Thiede, et al., The Journal of Biological Chemistry, vol. 261, No. 28, pp. 13230-13235 (1986).
Z. Xin, et al., Bioorganic & Medicinal Chemistry Letters, vol. 18, pp. 4298-4302 (2008).
S. Zhang, et al., Biochem J., vol. 388, pp. 135-142 (2005).
L. Zhang, et al., Biochem J., vol. 340, pp. 255-264 (1999).
H. Zhao, et al., Bioorganic & Medicinal Chemistry Letters, vol. 17, pp. 3388-3391 (2007).
Y. Zheng, et al., Nature Genetics, vol. 23, pp. 268-270 (1999).

SPIRO COMPOUNDS USEFUL AS INHIBITORS OF STEAROYL-COENZYME A DELTA-9 DESATURASE

CROSS-REFERENCE TO RELATED APPLICATIONS

This application is a U.S. National Phase application under 35 U.S.C. §371 of PCT Application No. PCT/CA2010/001150, filed Jul. 21, 2010, which claims priority from and the benefit of U.S. Provisional Application No. 61/229,049, filed Jul. 28, 2009.

FIELD OF THE INVENTION

The present invention relates to heteroaromatic compounds which are inhibitors of stearoyl-coenzyme A delta-9 desaturase (SCD) and the use of such compounds to control, prevent and/or treat conditions or diseases mediated by SCD activity. The compounds of the present invention are useful for the control, prevention and treatment of conditions and diseases related to abnormal lipid synthesis and metabolism, including cardiovascular disease, such as atherosclerosis; obesity; diabetes; neurological disease; metabolic syndrome; insulin resistance; cancer; and hepatic steatosis.

BACKGROUND OF THE INVENTION

At least three classes of fatty acyl-coenzyme A (CoA) desaturases (delta-5, delta-6 and delta-9 desaturases) are responsible for the formation of double bonds in mono- and polyunsaturated fatty acyl-CoAs derived from either dietary sources or de novo synthesis in mammals. The delta-9 specific stearoyl-CoA desaturases (SCDs) catalyze the rate-limiting formation of the cis-double bond at the C9-C10 position in monounsaturated fatty acyl-CoAs. The preferred substrates are stearoyl-CoA and palmitoyl-CoA, with the resulting oleoyl and palmitoleoyl-CoA as the main components in the biosynthesis of phospholipids, triglycerides, cholesterol esters and wax esters (Dobrzyn and Natami, Obesity Reviews, 6: 169-174 (2005)).

The rat liver microsomal SCD protein was first isolated and characterized in 1974 (Strittmatter et al., PNAS, 71: 4565-4569 (1974)). A number of mammalian SCD genes have since been cloned and studied from various species. For example, two genes have been identified from rat (SCD1 and SCD2, Thiede et al., J. Biol. Chem., 261, 13230-13235 (1986)), Mihara, K., J. Biochem. (Tokyo), 108: 1022-1029 (1990)); four genes from mouse (SCD1, SCD2, SCD3 and SCD4) (Miyazaki et al., J. Biol. Chem., 278: 33904-33911 (2003)); and two genes from human (SCD1 and ACOD4 (SCD2)), (Zhang, et al., Biochem. J., 340: 255-264 (1991); Beiraghi, et al., Gene, 309: 11-21 (2003); Zhang et al., Biochem. J., 388: 135-142 (2005)). The involvement of SCDs in fatty acid metabolism has been known in rats and mice since the 1970's (Oshino, N., Arch. Biochem. Biophys., 149: 378-387 (1972)). This has been further supported by the biological studies of a) Asebia mice that carry the natural mutation in the SCD1 gene (Zheng et al., Nature Genetics, 23: 268-270 (1999)), b) SCD1-null mice from targeted gene deletion (Ntambi, et al., PNAS, 99: 11482-11486 (2002), and c) the suppression of SCD1 expression during leptin-induced weight loss (Cohen et al., Science, 297: 240-243 (2002)). The potential benefits of pharmacological inhibition of SCD activity has been demonstrated with anti-sense oligonucleotide inhibitors (ASO) in mice (Jiang, et al., J. Clin. Invest., 115: 1030-1038 (2005)). ASO inhibition of SCD activity reduced fatty acid synthesis and increased fatty acid oxidation in primary mouse hepatocytes. Treatment of mice with SCD-ASOs resulted in the prevention of diet-induced obesity, reduced body adiposity, hepatomegaly, steatosis, postprandial plasma insulin and glucose levels, reduced de novo fatty acid synthesis, decreased the expression of lipogenic genes, and increased the expression of genes promoting energy expenditure in liver and adipose tissues. Thus, SCD inhibition represents a novel therapeutic strategy in the treatment of obesity and related metabolic disorders.

There is compelling evidence to support that elevated SCD activity in humans is directly implicated in several common disease processes. For example, there is an elevated hepatic lipogenesis to triglyceride secretion in non-alcoholic fatty liver disease patients (Diraison, et al., Diabetes Metabolism, 29: 478-485 (2003)); Donnelly, et al., J. Clin. Invest., 115: 1343-1351 (2005)). Elevated SCD activity in adipose tissue is closely coupled to the development of insulin resistance (Sjogren, et al., Diabetologia, 51(2): 328-35 (2007)). The postprandial de novo lipogenesis is significantly elevated in obese subjects (Marques-Lopes, et al., American Journal of Clinical Nutrition, 73: 252-261 (2001)). Knockout of the SCD gene ameliorates Metabolic Syndrome by reducing plasma triglycerides, reducing weight gain, increasing insulin sensitivity, and reduces hepatic lipid accumulation (MacDonald, et al., Journal of Lipid Research, 49(1): 217-29 (2007)). There is a significant correlation between a high SCD activity and an increased cardiovascular risk profile including elevated plasma triglycerides, a high body mass index and reduced plasma HDL (Attie, et al., J. Lipid Res., 43: 1899-1907 (2002)). SCD activity plays a key role in controlling the proliferation and survival of human transformed cells (Scaglia and Igal, J. Biol. Chem., (2005)). RNA interference of SCD-1 reduces human tumor cell survival (Morgan-Lappe, et al., Cancer Research, 67(9): 4390-4398 (2007)).

Other than the above mentioned anti-sense oligonucleotides, inhibitors of SCD activity include non-selective thiafatty acid substrate analogs [B. Behrouzian and P. H. Buist, Prostaglandins, Leukotrienes, and Essential Fatty Acids, 68: 107-112 (2003)], cyclopropenoid fatty acids (Raju and Reiser, J. Biol. Chem., 242: 379-384 (1967)), certain conjugated long-chain fatty acid isomers (Park, et al., Biochim. Biophys. Acta, 1486: 285-292 (2000)), and a series of heterocyclic derivatives disclosed in published international patent application publications WO 2005/011653, WO 2005/011654, WO 2005/011655, WO 2005/011656, WO 2005/011657, WO 2006/014168, WO 2006/034279, WO 2006/034312, WO 2006/034315, WO 2006/034338, WO 2006/034341, WO 2006/034440, WO 2006/034441, WO 2006/034446, WO 2006/086445; WO 2006/086447; WO 2006/101521; WO 2006/125178; WO 2006/125179; WO 2006/125180; WO 2006/125181; WO 2006/125194; WO 2007/044085; WO 2007/046867; WO 2007/046868; WO 2007/050124; WO 2007/130075; WO 2007/136746; and WO 2008/074835, all assigned to Xenon Pharmaceuticals, Inc. SCD inhibitors are also disclosed in the following published international patent application publications: WO 2008/074835; WO 2008/074824; WO 2008/036715; WO 2008/044767; WO 2008/029266; WO 2008/062276; and WO 2008/127349.

A number of international patent applications assigned to Merck Frosst Canada Ltd. that disclose SCD inhibitors useful for the treatment of obesity and Type 2 diabetes have also published: WO 2006/130986 (14 Dec. 2006); WO 2007/009236 (25 Jan. 2007); WO 2007/056846 (24 May 2007); WO 2007/071023 (28 Jun. 2007); WO 2007/134457 (29 Nov. 2007); WO 2007/143823 (21 Dec. 2007); WO 2007/143824

(21 Dec. 2007); WO 2008/017161 (14 Feb. 2008); WO 2008/046226 (24 Apr. 2008); WO 2008/064474 (5 Jun. 2008); and US 2008/0182838 (31 Jul. 2008).

WO 2008/003753 (assigned to Novartis) discloses a series of pyrazolo[1,5-a]pyrimidine analogs as SCD inhibitors; WO 2007/143697 and WO 2008/024390 (assigned to Novartis and Xenon Pharmaceuticals) disclose heterocyclic derivatives as SCD inhibitors; and WO 2008/096746 (assigned to Takeda Pharmaceutical) and WO 2008/056687 (assigned to Daiichi) disclose spiro compounds as SCD inhibitors.

Small molecule SCD inhibitors have also been described by (a) G. Liu, et al., "Discovery of Potent, Selective, Orally Bioavailable SCD1 Inhibitors," in J. Med. Chem., 50: 3086-3100 (2007); (b) H. Zhao, et al., "Discovery of 1-(4-phenoxypiperidin-1-yl)-2-arylaminoethanone SCD 1 inhibitors," Bioorg. Med. Chem. Lett., 17: 3388-3391 (2007); and (c) Z. Xin, et al., "Discovery of piperidine-aryl urea-based stearoyl-CoA desaturase 1 inhibitors," Bioorg. Med. Chem. Lett., 18: 4298-4302 (2008).

The present invention is concerned with novel heteroaromatic compounds as inhibitors of stearoyl-CoA delta-9 desaturase which are useful in the treatment and/or prevention of various conditions and diseases mediated by SCD activity including those related, but not limited, to elevated lipid levels, as exemplified in non-alcoholic fatty liver disease, cardiovascular disease, obesity, diabetes, metabolic syndrome, and insulin resistance.

The role of stearoyl-coenzyme A desaturase in lipid metabolism has been described by M. Miyazaki and J. M. Ntambi, Prostaglandins, Leukotrienes, and Essential Fatty Acids, 68: 113-121 (2003). The therapeutic potential of the pharmacological manipulation of SCD activity has been described by A. Dobrzyn and J. M. Ntambi, in "Stearoyl-CoA desaturase as a new drug target for obesity treatment," Obesity Reviews, 6: 169-174 (2005).

SUMMARY OF THE INVENTION

The present invention relates to heteroaromatic compounds of structural formula I:

$$(I)$$

and pharmaceutically acceptable salts thereof.

These heteroaromatic compounds are effective as inhibitors of SCD. They are therefore useful for the treatment, control or prevention of disorders responsive to the inhibition of SCD, such as diabetes, insulin resistance, lipid disorders, obesity, atherosclerosis, metabolic syndrome, and cancer.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of SCD in a subject in need thereof by administering the compounds and pharmaceutical compositions of the present invention.

The present invention also relates to methods for the treatment, control, or prevention of Type 2 diabetes, insulin resistance, obesity, lipid disorders, atherosclerosis, metabolic syndrome, and cancer by administering the compounds and pharmaceutical compositions of the present invention.

The present invention also relates to methods for the treatment, control, or prevention of obesity by administering the compounds of the present invention in combination with a therapeutically effective amount of another agent known to be useful to treat the condition.

The present invention also relates to methods for the treatment, control, or prevention of Type 2 diabetes by administering the compounds of the present invention in combination with a therapeutically effective amount of another agent known to be useful to treat the condition.

The present invention also relates to methods for the treatment, control, or prevention of insulin resistance by administering the compounds of the present invention in combination with a therapeutically effective amount of another agent known to be useful to treat the condition.

The present invention also relates to methods for the treatment, control, or prevention of atherosclerosis by administering the compounds of the present invention in combination with a therapeutically effective amount of another agent known to be useful to treat the condition.

The present invention also relates to methods for the treatment, control, or prevention of lipid disorders by administering the compounds of the present invention in combination with a therapeutically effective amount of another agent known to be useful to treat the condition.

The present invention also relates to methods for the treatment, control, or prevention of metabolic syndrome by administering the compounds of the present invention in combination with a therapeutically effective amount of another agent known to be useful to treat the condition.

The present invention also relates to methods for the treatment, control, or prevention of cancer by administering the compounds of the present invention in combination with a therapeutically effective amount of another agent known to be useful to treat the condition.

DETAILED DESCRIPTION OF THE INVENTION

The present invention is concerned with heteroaromatic compounds useful as inhibitors of SCD. Compounds of the present invention are described by structural formula I:

$$(I)$$

or a pharmaceutically acceptable salt thereof, wherein:

Z is independently selected from the group consisting of: S, S(O), S(O)$_2$, O, NH and CH$_2$, wherein each NH is unsubstituted or substituted with R$^g$, and wherein CH$_2$ is unsubstituted or substituted with R$^2$;

B is a 5 membered heteroaryl ring containing 1, 2 or 3 heteroatoms selected from NH, O and S, wherein any CH is unsubstituted or substituted with one substituent selected from R$^a$, and wherein any NH is unsubstituted or substituted with one substituent selected from R$^b$;

each R$^1$ is independently selected from the group consisting of: hydrogen, halogen, and C$_{1-3}$ alkyl, wherein alkyl is unsubstituted or substituted with one to three substituents independently selected from halogen and hydroxy;

each R² is independently selected from the group consisting of:
(1) hydrogen,
(2) halogen,
(3) aryl,
(4) heteroaryl,
(5) biphenyl,
(6) $C_{1-6}$ alkyl,
(7) $(CH_2)_nOR^e$,
(8) $(CH_2)_nN(R^e)_2$,
(9) $(CH_2)_nC\equiv N$,
(10) $(CH_2)_nCOR^e$, and
(11) $(CH_2)_nS(O)_qR^e$;
wherein $CH_2$, alkyl, phenyl, aryl and heteroaryl are unsubstituted or substituted with one to three substituents independently selected from $R^f$;
each R³ is independently selected from the group consisting of:
(1) hydrogen,
(2) halogen,
(3) —$C_{1-6}$ alkyl,
(4) —$OC_{1-6}$ alkyl,
(5) $(CH_2)_nOR^e$,
(6) $(CH_2)_nN(R^e)_2$,
(7) $(CH_2)_nC\equiv N$,
(8) $(CH_2)_nCOR^e$, and
(9) $(CH_2)_nS(O)_qR^e$,
wherein alkyl is unsubstituted or substituted with hydroxy or one to three halogens, and wherein any $CH_2$ in R³ is unsubstituted or substituted with one to two groups independently selected from halogen, hydroxy, and $C_{1-4}$ alkyl unsubstituted or substituted with one to five fluorines;
R⁴ is selected from the group consisting of:

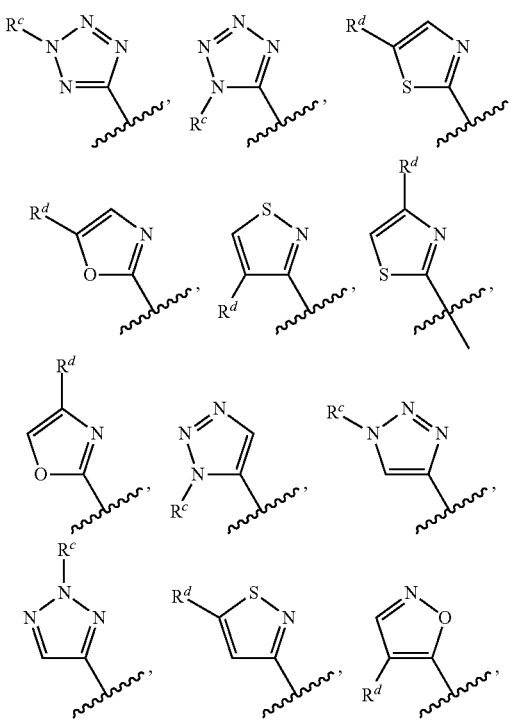
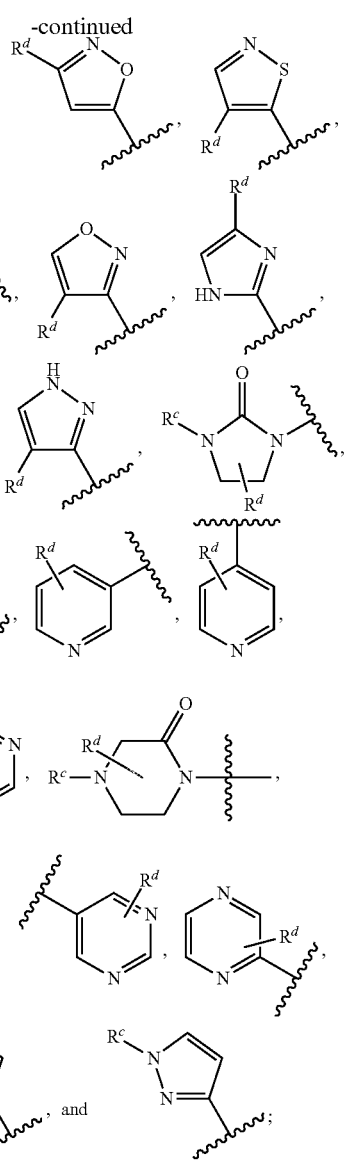

each $R^a$ is independently selected from the group consisting of:
(1) hydrogen,
(2) halogen,
(3) cyano,
(4) $C_{1-4}$ alkyl, unsubstituted or substituted with one to five fluorines,
(5) $C_{1-4}$ alkoxy, unsubstituted or substituted with one to five fluorines,
(6) $C_{1-4}$ alkylthio, unsubstituted or substituted with one to five fluorines,
(7) $C_{1-4}$ alkylsulfonyl,
(8) —$CO_2H$,
(9) $C_{1-4}$ alkyloxycarbonyl, and
(10) $C_{1-4}$ alkylcarbonyl;
each $R^b$ is independently selected from the group consisting of:
(1) hydrogen, and
(2) $C_{1-4}$ alkyl,
wherein alkyl is unsubstituted or substituted with one to five fluorines;
each $R^c$ is independently selected from the group consisting of:

(1) —(CH$_2$)$_m$CO$_2$H,
(2) —(CH$_2$)$_m$CO$_2$C$_{1-3}$ alkyl,
(3) —(CH$_2$)$_m$—NR$^b$—(CH$_2$)$_p$CO$_2$H,
(4) —(CH$_2$)$_m$—NR$^b$—(CH$_2$)$_p$CO$_2$C$_{1-3}$ alkyl,
(5) —(CH$_2$)$_m$—O—(CH$_2$)$_p$CO$_2$H,
(6) —(CH$_2$)$_m$—O—(CH$_2$)$_p$CO$_2$C$_{1-3}$ alkyl,
(7) —(CH$_2$)$_m$—S—(CH$_2$)$_p$CO$_2$H, and
(8) —(CH$_2$)$_m$—S—(CH$_2$)$_p$CO$_2$C$_{1-3}$ alkyl,
wherein any CH$_2$ in R$^c$ is unsubstituted or substituted with one to two groups independently selected from halogen, hydroxy, and C$_{1-4}$ alkyl unsubstituted or substituted with one to five fluorines;
each R$^d$ is independently selected from the group consisting of:
(1) —(CH$_2$)$_n$CO$_2$H,
(2) —(CH$_2$)$_n$CO$_2$C$_{1-3}$ alkyl,
(3) —(CH$_2$)$_n$—NR$^b$—(CH$_2$)$_p$CO$_2$H,
(4) —(CH$_2$)$_n$—NR$^b$—(CH$_2$)$_p$CO$_2$C$_{1-3}$ alkyl,
(5) —(CH$_2$)$_n$—O—(CH$_2$)$_p$CO$_2$H,
(6) —(CH$_2$)$_n$—O—(CH$_2$)$_p$CO$_2$C$_{1-3}$ alkyl,
(7) —(CH$_2$)$_n$—S—(CH$_2$)$_p$CO$_2$H, and
(8) —(CH$_2$)$_n$—S—(CH$_2$)$_p$CO$_2$C$_{1-3}$ alkyl,
wherein any CH$_2$ in R$^d$ is unsubstituted or substituted with one to two groups independently selected from the group consisting of: halogen, hydroxy, and C$_{1-4}$ alkyl unsubstituted or substituted with one to five fluorines;
each R$^e$ is independently selected from the group consisting of:
(1) hydrogen, and
(2) C$_{1-6}$ alkyl,
wherein alkyl is unsubstituted or substituted with one to three substituents independently selected from the group consisting of: halogen, cyano, —C$_{1-4}$ alkoxy, —C$_{1-4}$ alkylthio, —C$_{1-4}$ alkylsulfonyl, —CO$_2$H, and —CO$_2$C$_{1-4}$ alkyl;
each R$^f$ is independently selected from the group consisting of:
(1) hydrogen,
(2) halogen,
(3) —C$_{1-6}$ alkyl,
(4) —OC$_{1-6}$ alkyl,
(5) (CH$_2$)$_n$OR$^e$,
(6) (CH$_2$)$_n$N(R$^e$)$_2$,
(7) (CH$_2$)$_n$C≡N,
(8) (CH$_2$)$_n$C(O)$_e$,
(9) (CH$_2$)$_n$S(O)$_q$R$^e$, and
(10) aryl,
wherein CH$_2$, alkyl and aryl are unsubstituted or substituted with one, two or three groups independently selected from halogen, hydroxy, and C$_{1-4}$ alkyl unsubstituted or substituted with one to five fluorines;
each R$^g$ is independently selected from the group consisting of:
(1) hydrogen, and
(2) C$_{1-6}$ alkyl;
m is an integer from 1 to 3;
n is an integer from 0 to 3;
p is an integer from 1 to 3;
q is an integer from 1 to 2;
r is an integer from 0 to 2;
s is an integer from 0 to 4;
t is an integer from 0 to 8;
d is an integer from 0 to 2; and
e is an integer from 0 to 2,
provided that d+e is 2.

In one embodiment of the present invention, B is a 5-membered heteroaryl ring containing 1, 2 or 3 heteroatoms selected from NH, O and S, wherein any CH is unsubstituted or substituted with one substituent selected from R$^a$, and wherein any NH is unsubstituted or substituted with one substituent selected from R$^b$.

In another class of this embodiment B is a 5-membered heteroaryl ring containing 2 or 3 heteroatoms selected from NH, O and S, wherein any CH is unsubstituted or substituted with one substituent selected from R$^a$, and wherein NH is unsubstituted or substituted with one substituent selected from R$^b$.

In another class of this embodiment, B is selected from the group consisting of:

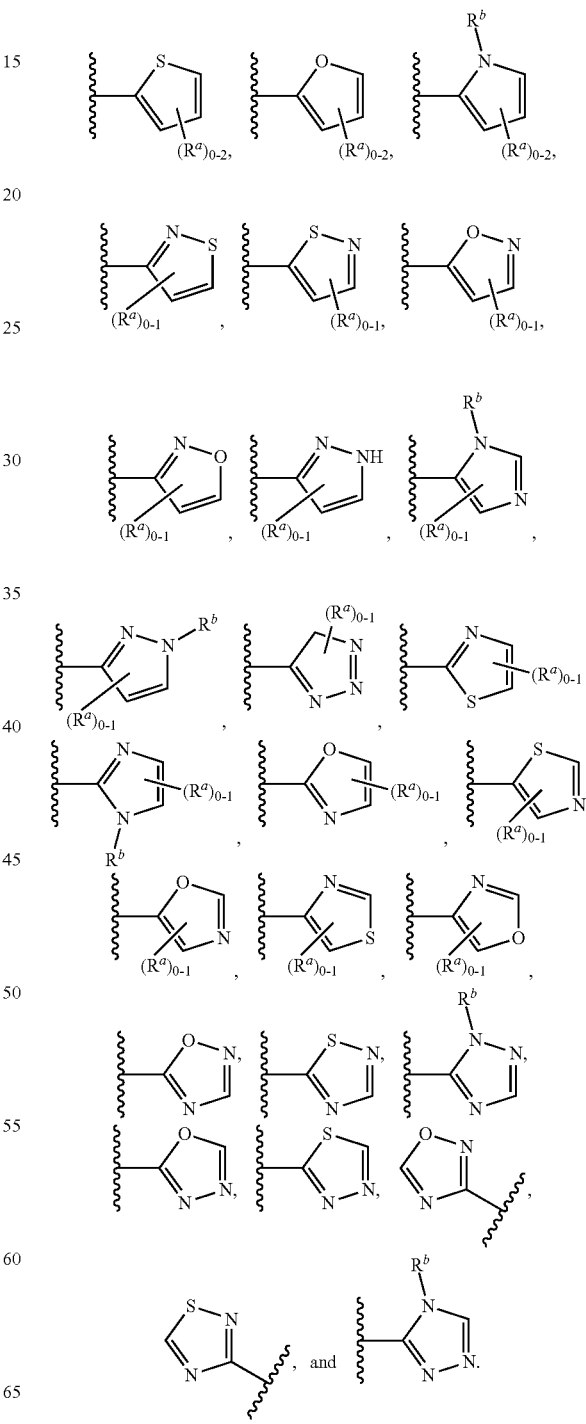

In another class of this embodiment, B is selected from the group consisting of:

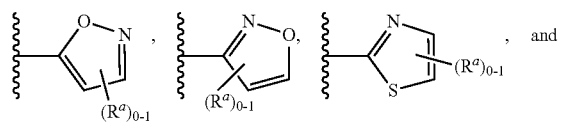

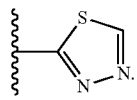

In another class of this embodiment, B is selected from the group consisting of:

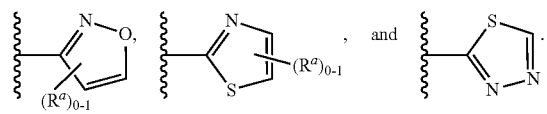

In another class of this embodiment, B is selected from the group consisting of:

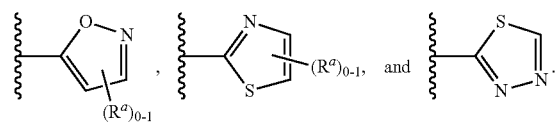

In another class of this embodiment, B is selected from the group consisting of:

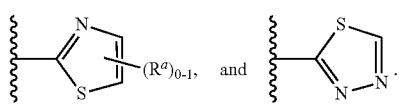

In another class of this embodiment, B is selected from the group consisting of:

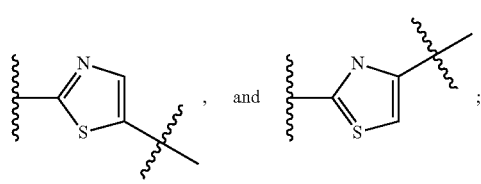

or a pharmaceutically acceptable salt thereof.

In another class of this embodiment, B is selected from the group consisting of:

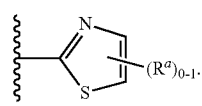

In another class of this embodiment, B is selected from the group consisting of:

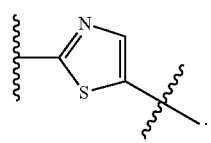 [SMILES: *c1cnc(*)s1]

In another class of this embodiment, B is selected from the group consisting of:

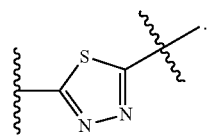 [SMILES: *c1nnc(*)s1]

In another class of this embodiment, B—$R^4$ is

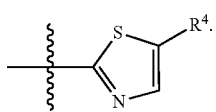

In yet another class of this embodiment, B—$R^4$ is

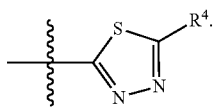

In yet another class of this embodiment, B—$R^4$ is

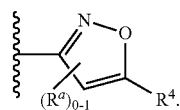

In another embodiment of the present invention, Z is independently selected from the group consisting of: S, S(O), $S(O)_2$, O, NH and $CH_2$, wherein each NH is unsubstituted or substituted with $R^g$, and wherein each $CH_2$ is unsubstituted or substituted with $R^2$. In a class of this embodiment, Z is independently selected from the group consisting of: S, O, NH and $CH_2$, wherein each NH is unsubstituted or substituted with $R^g$, and wherein each $CH_2$ is unsubstituted or substituted with $R^2$. In another class of this embodiment, Z is independently selected from the group consisting of: O, NH and $CH_2$, wherein each NH is unsubstituted or substituted with $R^g$, and wherein each $CH_2$ is unsubstituted or substituted with $R^2$.

In another embodiment of the present invention, Z is O.

In another embodiment of the present invention, each $R^1$ is independently selected from the group consisting of: hydrogen, halogen, and $C_{1-3}$ alkyl, wherein alkyl is unsubstituted or substituted with one to three substituents independently selected from halogen and hydroxy. In a class of this embodiment, each $R^1$ is independently selected from the group consisting of: hydrogen, halogen, or $C_{1-3}$ alkyl. In another class of this embodiment, each $R^1$ is hydrogen.

In another embodiment of the present invention, $R^1$ is hydrogen.

In another embodiment of the present invention, each $R^2$ is independently selected from the group consisting of: hydrogen, halogen, aryl, heteroaryl, biphenyl, $C_{1-6}$ alkyl, $(CH_2)_nOR^e$, $(CH_2)_nN(R^e)_2$, $(CH_2)_nC\equiv N$, $(CH_2)_nCOR^e$, and $(CH_2)_nS(O)_qR^e$, wherein $CH_2$, alkyl, phenyl, aryl and heteroaryl are unsubstituted or substituted with one to three substituents independently selected from $R^f$.

In a class of this embodiment, each $R^2$ is independently selected from the group consisting of: aryl, heteroaryl, biphenyl and —$C_{1-6}$ alkyl, wherein alkyl, biphenyl, aryl and heteroaryl are unsubstituted or substituted with one to three substituents independently selected from $R^f$.

In another class of this embodiment, each $R^2$ is independently selected from the group consisting of: phenyl, naphthalene, heteroaryl, biphenyl and —$C_{1-6}$ alkyl, wherein alkyl, phenyl, biphenyl, naphthalene and heteroaryl are unsubstituted or substituted with one to three substituents independently selected from $R^f$.

In another class of this embodiment, each $R^2$ is independently selected from the group consisting of: phenyl, naphthalene, furan, benzofuran, dibenzofuran, biphenyl and —$C_{1-6}$ alkyl, wherein alkyl, phenyl, biphenyl, naphthalene, furan, benzofuran, and dibenzofuran are unsubstituted or substituted with one to three substituents independently selected from $R^f$.

In another class of this embodiment, each $R^2$ is independently selected from the group consisting of: phenyl, naphthalene, furan, benzofuran, dibenzofuran, biphenyl and —$CH_3$, wherein —$CH_3$, phenyl, biphenyl, naphthalene, furan, benzofuran, dibenzofuran are unsubstituted or substituted with one to three substituents independently selected from $R^f$.

In another class of this embodiment, $R^2$ is selected from the group consisting of: aryl and heteroaryl, wherein each aryl and heteroaryl is unsubstituted or substituted with one to three substituents independently selected from $R^f$. In a subclass of this class, $R^2$ is selected from the group consisting of: phenyl and thiophene, wherein each phenyl and thiophene is unsubstituted or substituted with one to three substituents independently selected from $R^f$.

In another class of this embodiment, $R^2$ is selected from aryl and heteroaryl, wherein each aryl and heteroaryl is unsubstituted or substituted with one or two substituents independently selected from $R^f$. In a subclass of this class, $R^2$ is selected from the group consisting of: phenyl and thiophene, wherein each phenyl and thiophene is unsubstituted or substituted with one or two substituents independently selected from $R^f$.

In another class of this embodiment, $R^2$ is aryl, wherein aryl is unsubstituted or substituted with one to three substituents independently selected from $R^f$. In a subclass of this class, $R^2$ is phenyl, wherein phenyl is unsubstituted or substituted with one to three substituents independently selected from $R^f$.

In another class of this embodiment, $R^2$ is aryl, wherein aryl is unsubstituted or substituted with one to two substituents independently selected from $R^f$. In a subclass of this class, $R^2$ is phenyl, wherein phenyl is unsubstituted or substituted with one to two substituents independently selected from $R^f$.

In another embodiment of the present invention, $R^3$ is hydrogen or halogen. In a class of this embodiment, $R^3$ is hydrogen or chloro. In another embodiment of the present invention, $R^3$ is hydrogen.

In another embodiment of the present invention, $R^3$ is independently selected from the group consisting of: hydrogen, halogen, —$C_{1-6}$ alkyl, —$OC_{1-6}$ alkyl, $(CH_2)_nOR^e$, $(CH_2)_nN(R^e)_2$, $(CH_2)_nC\equiv N$, $(CH_2)_nCOR^e$, and $(CH_2)_nS(O)_qR^e$, wherein alkyl is unsubstituted or substituted with hydroxy or one to three halogens; and wherein any $CH_2$ in $R^3$ is unsubstituted or substituted with one to two groups independently selected from halogen, hydroxy, and $C_{1-4}$ alkyl unsubstituted or substituted with one to five fluorines. In a class of this embodiment, $R^3$ is independently selected from the group consisting of: hydrogen, halogen, —$C_{1-6}$ alkyl, —$OC_{1-6}$ alkyl, $(CH_2)_nOR^e$, $(CH_2)_nN(R^e)_2$, $(CH_2)_nC\equiv N$, and $(CH_2)_nCOR^e$, wherein alkyl is unsubstituted or substituted with hydroxy or one to three halogens; and wherein any $CH_2$ in $R^3$ is unsubstituted or substituted with one to two groups independently selected from halogen, hydroxy, and $C_{1-4}$ alkyl unsubstituted or substituted with one to five fluorines. In a class of this embodiment, $R^3$ is independently selected from the group consisting of: hydrogen, halogen, —$C_{1-6}$ alkyl, —OH, and —$OC_{1-6}$ alkyl, wherein alkyl is unsubstituted or substituted with hydroxy or one to three halogens; and wherein any $CH_2$ in $R^3$ is unsubstituted or substituted with one to two groups independently selected from halogen, hydroxy, and $C_{1-4}$ alkyl unsubstituted or substituted with one to five fluorines. In a subclass of this class, $R^3$ is independently selected from the group consisting of: hydrogen, halogen, —$C_{1-6}$ alkyl, —OH, and —$OC_{1-6}$ alkyl. In another subclass of this class, $R^3$ is independently selected from the group consisting of: hydrogen, halogen, —OH, and —$OC_{1-6}$ alkyl, wherein alkyl is unsubstituted or substituted with hydroxy or one to three halogens, and wherein any $CH_2$ in $R^3$ is unsubstituted or substituted with one to two groups independently selected from halogen, hydroxy, —OH, and $C_{1-4}$ alkyl unsubstituted or substituted with one to five fluorines. In another subclass of this class, $R^3$ is independently selected from the group consisting of: hydrogen, halogen, —OH, and —$OC_{1-6}$ alkyl. In another subclass of this class, $R^3$ is independently selected from the group consisting of: hydrogen, halogen, —OH and $OCH_3$. In another subclass of this class, $R^3$ is independently selected from the group consisting of: —OH and $OCH_3$. In another subclass of this class, $R^3$ is independently selected from the group consisting of: hydrogen, and halogen. In another subclass of this class, $R^3$ is independently selected from the group consisting of: hydrogen, bromo, chloro and fluoro. In another subclass of this class, $R^3$ is independently selected from the group consisting of: hydrogen, chloro and fluoro. In another subclass of this class, $R^3$ is independently selected from the group consisting of: hydrogen, and chloro. In another subclass of this class, $R^3$ is chloro. In another subclass of this class, $R^3$ is halogen. In another subclass of this class, $R^3$ is independently selected from the group consisting of: bromo, chloro and fluoro. In another subclass of this class, $R^3$ is independently selected from the group consisting of: chloro and fluoro. In another class of this embodiment, $R^3$ is chloro.

In another embodiment of the present invention, $R^4$ is selected from the group consisting of: heteroaryl, and cycloheteroalkyl, wherein any NH group is unsubstituted or substituted with $R^c$, and wherein any CH or $CH_2$ group is unsubstituted or substituted with 1 to 2 substituents selected from $R^d$. In a class of this embodiment, $R^4$ is heteroaryl, wherein any NH group is unsubstituted or substituted with $R^c$, and wherein any CH or $CH_2$ group is unsubstituted or substituted with one substituent selected from $R^d$. In a class of this embodiment, $R^4$ is heteroaryl, wherein any NH group is unsubstituted or substituted with $R^c$, and wherein any CH group is unsubstituted or substituted with one substituent selected from $R^d$. In another class of this embodiment, $R^4$ is cycloheteroalkyl, wherein any NH group is unsubstituted or substituted with $R^c$, and wherein any CH or $CH_2$ group is unsubstituted or substituted with one substituent selected from $R^d$. In another class of this embodiment, $R^4$ is cycloheteroalkyl, wherein any NH group is unsubstituted or substituted with $R^c$, and wherein any $CH_2$ group is unsubstituted or substituted with one to two substituents selected from $R^d$.

In another embodiment of the present invention, $R^4$ is selected from the group consisting of:

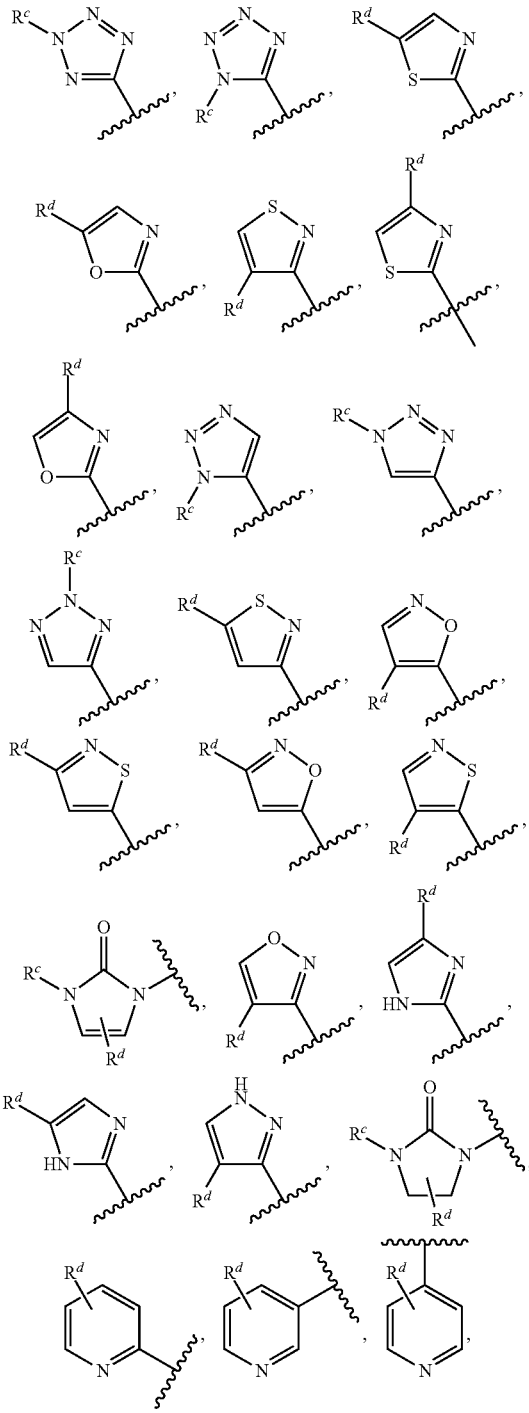

-continued

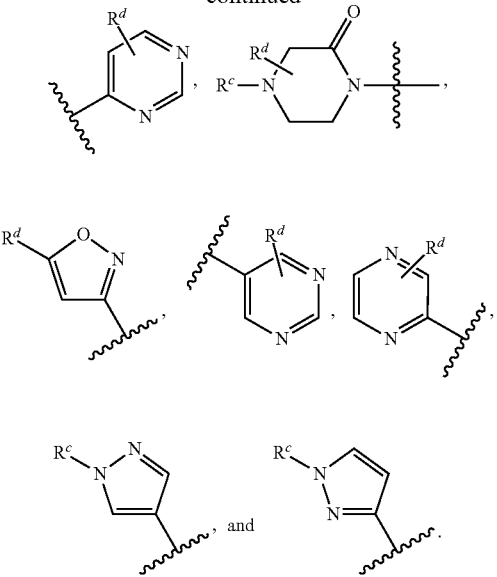

In a class of this embodiment, $R^4$ is selected from the group consisting of:

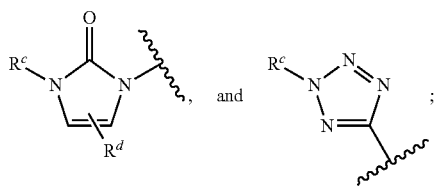

In another class of this embodiment, $R^4$ is:

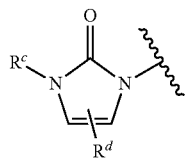

In another class of this embodiment, $R^4$ is:

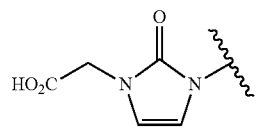

In another class of this embodiment, $R^4$ is:

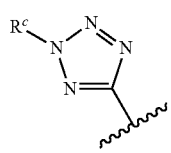

In another class of this embodiment, $R^4$ is:

[Structure: HO₂C-CH₂-N(triazole ring with N, N, N)- attached via wavy bond]

In another embodiment of the present invention, each $R^a$ is independently selected from the group consisting of: hydrogen, halogen, cyano, $C_{1-4}$ alkyl, unsubstituted or substituted with one to five fluorines, $C_{1-4}$ alkoxy, unsubstituted or substituted with one to five fluorines, $C_{1-4}$ alkylthio, unsubstituted or substituted with one to five fluorines, $C_{1-4}$ alkylsulfonyl, —$CO_2H$, $C_{1-4}$ alkyloxycarbonyl, and $C_{1-4}$ alkylcarbonyl. In a class of this embodiment, $R^a$ is independently selected from the group consisting of: hydrogen, halogen, cyano, and $C_{1-4}$ alkyl, unsubstituted or substituted with one to five fluorines. In another class of this embodiment, $R^a$ is independently selected from the group consisting of: hydrogen, and $C_{1-4}$ alkyl, unsubstituted or substituted with one to five fluorines. In another class of this embodiment, $R^a$ is hydrogen. In another class of this embodiment, $R^a$ is $C_{1-4}$ alkyl, unsubstituted or substituted with one to five fluorines. In another class of this embodiment, $R^a$ is $C_{1-4}$ alkyl.

In another embodiment of the present invention, each $R^b$ is independently selected from the group consisting of: hydrogen, and $C_{1-4}$ alkyl, wherein alkyl is unsubstituted or substituted with one to five fluorines. In a class of this embodiment, $R^b$ is hydrogen. In another class of this embodiment, $R^b$ is $C_{1-4}$ alkyl, wherein alkyl is unsubstituted or substituted with one to five fluorines. In another class of this embodiment, $R^b$ is $C_{1-4}$ alkyl.

In another embodiment of the present invention, each $R^c$ is independently selected from the group consisting of: —$(CH_2)_mCO_2H$, —$(CH_2)_mCO_2C_{1-3}$ alkyl, —$(CH_2)_m$—$NR^b$—$(CH_2)_pCO_2H$, —$(CH_2)_m$—$NR^b$—$(CH_2)_pCO_2C_{1-3}$ alkyl, —$(CH_2)_m$—O—$(CH_2)_pCO_2H$, —$(CH_2)_m$—O—$(CH_2)_p CO_2C_{1-3}$ alkyl, —$(CH_2)_m$—S—$(CH_2)_pCO_2H$, and —$(CH_2)_m$—S—$(CH_2)_pCO_2C_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is selected from the group consisting of: —$(CH_2)_mCO_2H$, —$(CH_2)_mCO_2C_{1-3}$ alkyl, —$(CH_2)_mOCOH$, —$(CH_2)_mOCOC_{1-3}$ alkyl, —$(CH_2)_mCOH$, —$(CH_2)_mCOC_{1-3}$ alkyl, —$(CH_2)_m$—$NR^b$—$(CH_2)_pCO_2H$, —$(CH_2)_m$—$NR^b$—$(CH_2)_pCO_2C_{1-3}$ alkyl, —$(CH_2)_m$—O—$(CH_2)_pCO_2H$, and —$(CH_2)_m$—O—$(CH_2)_pCO_2C_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is selected from the group consisting of: —$(CH_2)_mCO_2H$, —$(CH_2)_mCO_2C_{1-3}$ alkyl, —$(CH_2)_mOCOH$, —$(CH_2)_mO$-$COC_1$-3 alkyl, —$(CH_2)_mCOH$, and —$(CH_2)_mCOC_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is selected from the group consisting of: —$(CH_2)_mCO_2H$, —$(CH_2)_mCO_2C_{1-3}$ alkyl, —$(CH_2)_mOCOH$, —$(CH_2)_mO$-$COC_{1-3}$ alkyl, —$(CH_2)_mCOH$, —$(CH_2)_mCOC_{1-3}$ alkyl, —$(CH_2)_m$—$NR^b$—$(CH_2)_pCO_2H$, —$(CH_2)_m$—$NR^b$—$(CH_2)_p CO_2C_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is selected from the group consisting of: —$(CH_2)_mCO_2H$, and —$(CH_2)_mCO_2C_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is —$(CH_2)_m CO_2H$. In another class of this embodiment, $R^c$ is —$(CH_2)_m CO_2C_{1-3}$ alkyl.

In another embodiment of the present invention, each $R^d$ is independently selected from the group consisting of: —$(CH_2)_nCO_2H$, —$(CH_2)_nCO_2C_{1-3}$ alkyl, —$(CH_2)_n$—$NR^b$—$(CH_2)_pCO_2H$, —$(CH_2)_n$—$NR^b$—$(CH_2)_pCO_2C_{1-3}$ alkyl, —$(CH_2)_n$—O—$(CH_2)_pCO_2H$, —$(CH_2)_n$—O—$(CH_2)_p CO_2C_{1-3}$ alkyl, —$(CH_2)_n$—S—$(CH_2)_pCO_2H$, and —$(CH_2)_n$—S—$(CH_2)_pCO_2C_{1-3}$ alkyl, wherein any $CH_2$ in $R^d$ is unsubstituted or substituted with one to two groups independently selected from the group consisting of: halogen, hydroxy, and $C_{1-4}$ alkyl unsubstituted or substituted with one to five fluorines. In another class of this embodiment, each $R^d$ is independently selected from the group consisting of: —$(CH_2)_nCO_2H$, —$(CH_2)_nCO_2C_{1-3}$ alkyl, —$(CH_2)_n$—$NR^b$—$(CH_2)_pCO_2H$, —$(CH_2)_n$—$NR^b$—$(CH_2)_pCO_2C_{1-3}$ alkyl, —$(CH_2)_n$—O—$(CH_2)_pCO_2H$, and —$(CH_2)_n$—O—$(CH_2)_pCO_2C_{1-3}$ alkyl, wherein any $CH_2$ in $R^d$ is unsubstituted or substituted with one to two groups independently selected from the group consisting of: halogen, hydroxy, and $C_{1-4}$ alkyl unsubstituted or substituted with one to five fluorines. In another class of this embodiment, $R^d$ is selected from the group consisting of: —$(CH_2)_nCO_2H$, —$(CH_2)_nCO_2C_{1-3}$ alkyl, —$(CH_2)_n$—$NR^b$—$(CH_2)_pCO_2H$, and —$(CH_2)_n$—$NR^b$—$(CH_2)_pCO_2C_{1-3}$ alkyl, wherein any $CH_2$ in $R^d$ is unsubstituted or substituted with one to two groups independently selected from halogen, hydroxy, and $C_{1-4}$ alkyl unsubstituted or substituted with one to five fluorines. In another class of this embodiment, $R^d$ is selected from the group consisting of: —$(CH_2)_nCO_2H$, and —$(CH_2)_n$—$NR^b$—$(CH_2)_p CO_2H$, wherein any $CH_2$ in $R^d$ is unsubstituted or substituted with one to two groups independently selected from halogen, hydroxy, and $C_{1-4}$ alkyl unsubstituted or substituted with one to five fluorines. In another class of this embodiment, $R^d$ is selected from the group consisting of: —$CH_2CO_2H$, and —$NH$—$CH_2CO_2H$. In another class of this embodiment, $R^d$ is —$CH_2CO_2H$. In another class of this embodiment, $R^d$ is —$NH$—$CH_2CO_2H$.

In another embodiment of the present invention, each $R^e$ is independently selected from the group consisting of: hydrogen, and $C_{1-6}$ alkyl, wherein alkyl is unsubstituted or substituted with one to three substituents independently selected from the group consisting of halogen, cyano, —$C_{1-4}$ alkoxy, —$C_{1-4}$ alkylthio, —$C_{1-4}$ alkylsulfonyl, —$CO_2H$, and —$CO_2C_{1-4}$ alkyl. In a class of this embodiment, each $R^e$ is independently selected from the group consisting of: hydrogen, and $C_{1-6}$ alkyl, wherein alkyl is unsubstituted or substituted with one to three substituents independently selected from the group consisting of halogen. In another class of this embodiment, each $R^e$ is independently selected from the group consisting of: hydrogen, and $C_{1-6}$ alkyl. In another class of this embodiment, $R^e$ is hydrogen. In another class of this embodiment, $R^e$ is $C_{1-6}$ alkyl, wherein alkyl is unsubstituted or substituted with one to three substituents independently selected from the group consisting of: halogen, cyano, —$C_{1-4}$ alkoxy, $C_{1-4}$ alkylthio, —$C_{1-4}$ alkylsulfonyl, —$CO_2H$, and —$CO_2C_{1-4}$ alkyl. In another class of this embodiment, $R^e$ is $C_{1-6}$ alkyl, wherein alkyl is unsubstituted or substituted with one to three substituents independently selected from the group consisting of: halogen. In another class of this embodiment, $R^e$ is $C_{1-6}$ alkyl.

In another embodiment of the present invention, each $R^f$ is independently selected from the group consisting of: hydrogen, halogen, —$C_{1-6}$ alkyl, —$OC_{1-6}$ alkyl, —$(CH_2)_nOR^e$, —$(CH_2)_nN(R^e)_2$, —$(CH_2)_nC\equiv N$, —$(CH_2)_nCOR^e$, —$(CH_2)_nS(O)_qR^e$, and aryl, wherein $CH_2$, alkyl and aryl are unsubstituted or substituted with one, two or three groups independently selected from halogen, hydroxy, and $C_{1-4}$ alkyl unsubstituted or substituted with one to five fluorines. In a class of this embodiment, each $R^f$ is independently selected from the group consisting of: hydrogen, halogen, —$C_{1-6}$ alkyl, —$OC_{1-6}$ alkyl, —$(CH_2)_nOR^e$, —$(CH_2)_nN(R^e)_2$, —$(CH_2)_nC\equiv N$, —$(CH_2)_nCOR^e$, —$(CH_2)_nS(O)_qR^e$, and phenyl, wherein $CH_2$, alkyl and phenyl are unsubstituted or substituted with one, two or three groups independently selected from halogen, hydroxy, and $C_{1-4}$ alkyl unsubstituted or substituted with one to five fluorines. In another class of this embodiment, each $R^f$ is independently selected from the group consisting of: hydrogen, halogen, —$C_{1-6}$ alkyl, —$OC_{1-6}$ alkyl, and phenyl, wherein alkyl and phenyl are unsubstituted or substituted with one, two or three groups independently selected from halogen, hydroxy, and $C_{1-4}$ alkyl unsubstituted or substituted with one to five fluorines. In another class of this embodiment, each $R^f$ is independently selected from the group consisting of: halogen, —$C_{1-6}$ alkyl, —$OC_{1-6}$ alkyl, and phenyl, wherein alkyl and phenyl are unsubstituted or substituted with one, two or three groups independently selected from halogen, hydroxy, and $C_{1-4}$ alkyl unsubstituted or substituted with one to five fluorines.

In another embodiment of the present invention, each $R^f$ is independently selected from the group consisting of: halogen, —$CF_3$, —$OCF_3$, —$C_{1-6}$ alkyl, —$OC_{1-6}$ alkyl, and phenyl, wherein alkyl and phenyl are unsubstituted or substituted with one to two groups independently selected from the group consisting of: halogen, hydroxy, and $C_{1-4}$ alkyl unsubstituted or substituted with one to five fluorines. In a subclass of this class, each $R^f$ is independently selected from the group consisting of: F, Cl, —$CF_3$, —$OCF_3$, —$CH_3$, —$CH(CH_3)_2$, —$OCH_3$, and phenyl, wherein phenyl is unsubstituted or substituted with one to two groups independently selected from the group consisting of: halogen, hydroxy, and $C_{1-4}$ alkyl unsubstituted or substituted with one to five fluorines. In another subclass of this class, each $R^f$ is independently selected from the group consisting of: F, Cl, —$CF_3$, —$OCF_3$, —$CH_3$, —$CH(CH_3)_2$, —$OCH_3$, and phenyl.

In a class of this embodiment, each $R^f$ is independently selected from the group consisting of: halogen, —$CF_3$, —$OCF_3$, —$C_{1-6}$ alkyl, and —$OC_{1-6}$ alkyl, wherein alkyl is unsubstituted or substituted with one to two groups independently selected from the group consisting of: halogen, hydroxy, and $C_{1-4}$ alkyl unsubstituted or substituted with one to five fluorines.

In another class of this embodiment, each $R^f$ is independently selected from the group consisting of: halogen, —$CF_3$, —$OCF_3$, —$C_{1-6}$ alkyl, and —$OC_{1-6}$ alkyl. In a subclass of this class, each $R^f$ is independently selected from the group consisting of: F, Cl, —$CF_3$, —$OCF_3$, —$CH_3$, —$CH(CH_3)_2$, and —$OCH_3$.

In another class of this embodiment, each $R^f$ is independently selected from the group consisting of: halogen, and —$OCF_3$. In a subclass of this class, each $R^f$ is independently selected from the group consisting of: F, Cl, and —$OCF_3$.

In another embodiment of the present invention, each $R^g$ is independently selected from the group consisting of: hydrogen, and $C_{1-6}$ alkyl. In a class of this embodiment, $R^g$ is hydrogen. In another class of this embodiment, $R^g$ is $C_{1-6}$ alkyl.

In another embodiment of the present invention, m is 1, 2, or 3. In a class of this embodiment, m is 1 or 2. In another class of this embodiment, m is 2 or 3. In another class of this embodiment, m is 1 or 3. In another class of this embodiment, m is 1. In another class of this embodiment, m is 2. In another class of this embodiment, m is 3.

In another embodiment of the present invention, n is 0, 1, 2 or 3. In a class of this embodiment, n is 0, 1 or 2. In another class of this embodiment, n is 0 or 1. In another class of this embodiment, n is 1 or 2. In another class of this embodiment, n is 0 or 2. In another class of this embodiment, n is 0. In another class of this embodiment, n is 1. In another class of this embodiment, n is 2. In another class of this embodiment, n is 3.

In another embodiment of the present invention, p is 1, 2, or 3. In a class of this embodiment, p is 1 or 2. In another class of this embodiment, p is 2 or 3. In another class of this embodiment, p is 1 or 3. In another class of this embodiment, p is 1. In another class of this embodiment, p is 2. In another class of this embodiment, p is 3.

In another embodiment of the present invention, q is 1 or 2. In another class of this embodiment, q is 1. In another class of this embodiment, q is 2.

In another embodiment of the present invention, r is 0, 1 or 2. In another class of this embodiment, r is 0 or 1. In another class of this embodiment, r is 1 or 2. In another class of this embodiment, r is 0 or 2. In another class of this embodiment, r is 0. In another class of this embodiment, r is 1. In another class of this embodiment, r is 2. In another class of this embodiment, r is 3.

In another embodiment of the present invention, s is 0, 1, 2, 3 or 4. In a class of this embodiment, s is 0, 1, 2 or 3. In a class of this embodiment, s is 0, 1 or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3.

In another embodiment of the present invention, t is 0, 1, 2, 3, 4, 5, 6, 7 or 8. In a class of this embodiment, t is 0, 1, 2, 3 or 4. In a class of this embodiment, t is 0, 1, 2 or 3. In a class of this embodiment, t is 0, 1 or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3. In another class of this embodiment, t is 4. In another class of this embodiment, t is 5. In another class of this embodiment, t is 6. In another class of this embodiment, t is 7. In another class of this embodiment, t is 8.

In another embodiment of the present invention, d is 0, 1 or 2. In a class of this embodiment, d is 0. In another class of this embodiment, d is 1. In another class of this embodiment, d is 2.

In another embodiment of the present invention, e is 0, 1 or 2. In a class of this embodiment, e is 0. In another class of this embodiment, e is 1. In another class of this embodiment, e is 2.

In another embodiment of the present invention, d is 0, and e is 2. In another embodiment of the present invention, d is 1 and e is 1. In another embodiment of the present invention, d is 2 and e is 0.

In another embodiment of the present invention, the invention relates to compounds of structural formula I, wherein:
Z is O;
B is selected from the group consisting of:

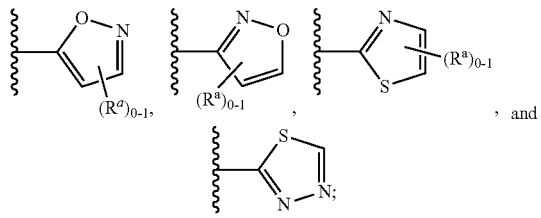

R2 is independently selected from the group consisting of:
(1) aryl,
(2) heteroaryl,
(3) biphenyl,
(4) —C$_{1-6}$ alkyl,
wherein alkyl, biphenyl, aryl and heteroaryl are unsubstituted or substituted with one to three substituents independently selected from R$^f$;
R$^3$ is independently selected from the group consisting of: hydrogen and halogen;
R$^4$ is selected from the group consisting of:

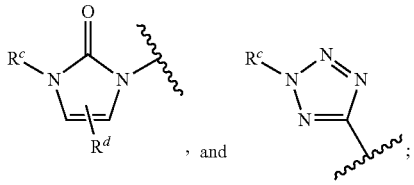

d is 1;
e is 1;
r is 1;
s is 0 or 1; and
t is 0;
or a pharmaceutically acceptable salt thereof.

In another embodiment of the present invention, the invention relates to compounds of structural formula I, wherein:
Z is O;
B is selected from the group consisting of:

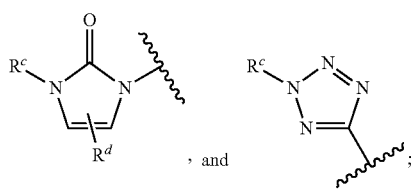

R2 is independently selected from the group consisting of:
(1) aryl,
(2) heteroaryl,
(3) biphenyl,
(4) —C$_{1-6}$ alkyl,
wherein alkyl, biphenyl, aryl and heteroaryl are unsubstituted or substituted with one to three substituents independently selected from R$^f$;
R$^3$ is independently selected from the group consisting of: hydrogen and halogen;
R$^4$ is selected from the group consisting of:

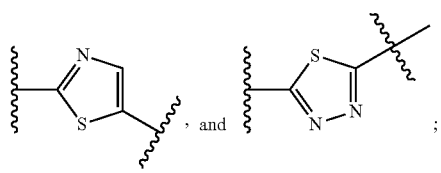

d is 1;
e is 1;
r is 1;
s is 0 or 1; and
t is 0;
or a pharmaceutically acceptable salt thereof.

In another embodiment of the present invention, the invention relates to compounds of structural formula I, wherein:
Z is O;
B is selected from the group consisting of:

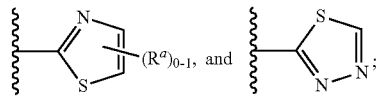

R2 is phenyl, wherein phenyl is unsubstituted or substituted with one to three substituents independently selected from R$^f$;
R$^3$ is independently selected from the group consisting of: hydrogen and halogen;
R$^4$ is

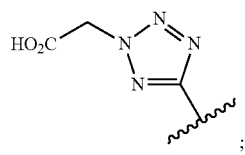 [SMILES: *c1nnn(CC(=O)O)n1 ; ";"]

d is 1;
e is 1;
r is 1;
s is 0 or 1; and
t is 0;
or a pharmaceutically acceptable salt thereof.

In another embodiment of the present invention, the invention relates to compounds of structural formula Ia:

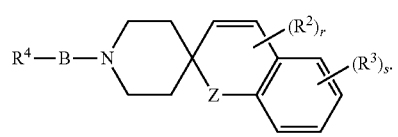

Ia

In another embodiment of the present invention, the invention relates to compounds of structural formula Ib:

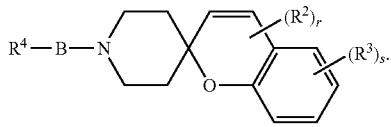

Ib

In another embodiment of the present invention, the invention relates to compounds of structural formula Ic:

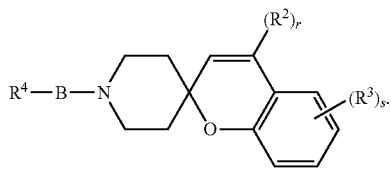

Ic

In another embodiment of the present invention, the invention relates to compounds of structural formula Id:

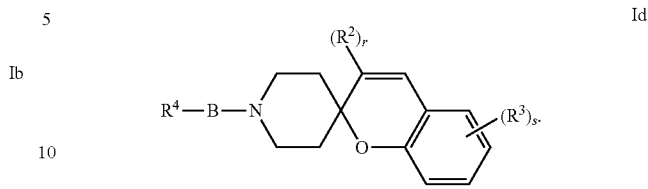

Id

In another embodiment of the present invention, the invention relates to compounds of structural formula Ie:

Ie

R⁴—B—N

Illustrative, but non-limiting, examples of compounds of the present invention that are useful as inhibitors of SCD are the following:

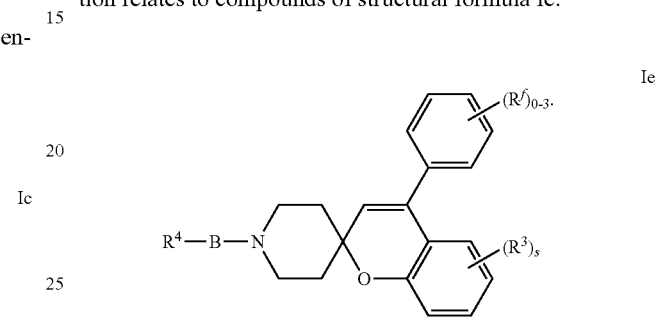

| Example | Structure | IC₅₀ hSCD-1 |
|---|---|---|
| 1 | 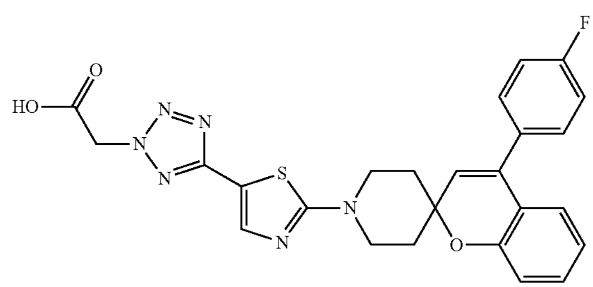 | 0.92 nM |
| 2 | 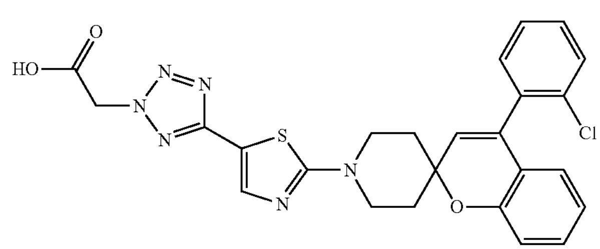 [SMILES: O=C(O)Cn1nnc(-c2cnc(N3CCC4(C=C(c5ccccc5Cl)c5ccccc5O4)CC3)s2)n1] | 0.61 nM |

-continued
| Example | Structure | IC$_{50}$ hSCD-1 |
|---------|-----------|------------------|
| 3 | 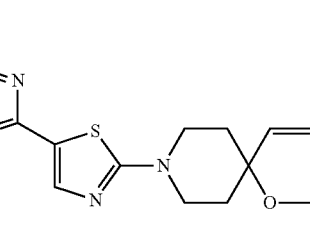 | 1.1 nM |
| 4 | 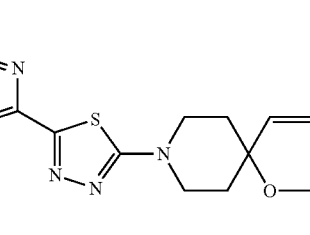 | 2.0 nM |
| 5 | 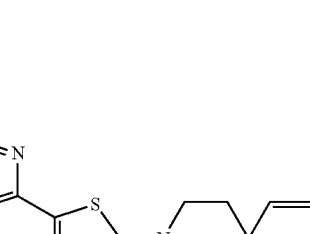 | 1.1 nM |
| 6 | 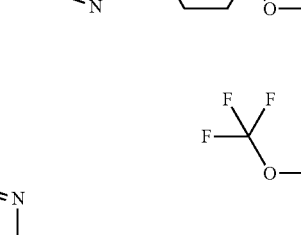 | 1.3 nM |
| 7 | 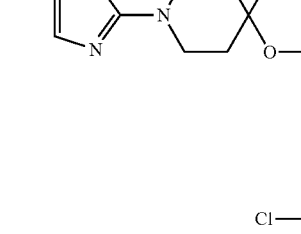 | 0.97 nM |

-continued
| Example | Structure | IC$_{50}$ hSCD-1 |
|---|---|---|
| 8 | 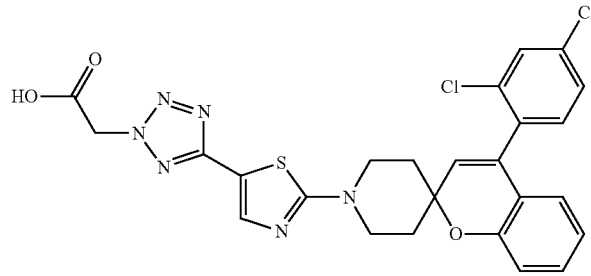 | 1.0 |
| 9 | 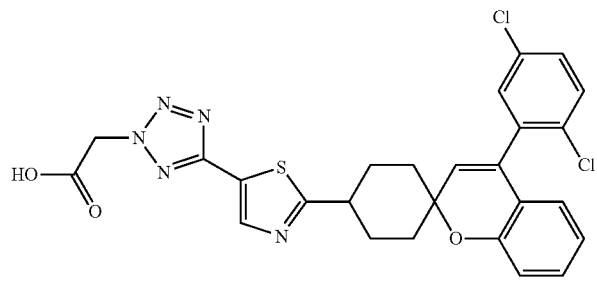 [SMILES: O=C(O)Cn1nnc(-c2cnc(C3CCC4(C=C(c5cc(Cl)ccc5Cl)c5ccccc5O4)CC3)s2)n1] | 1.4 nM |
| 10 | 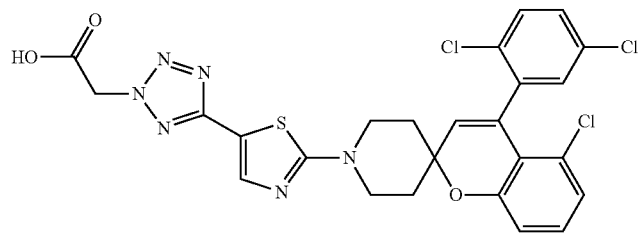 [SMILES: O=C(O)Cn1nnc(-c2cnc(N3CCC4(C=C(c5cc(Cl)ccc5Cl)c5c(Cl)cccc5O4)CC3)s2)n1] | 1.3 nM |
| 11 | 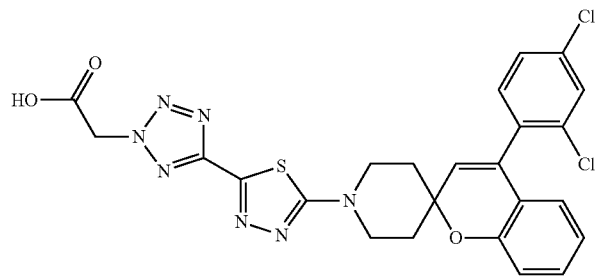 [SMILES: O=C(O)Cn1nnc(-c2nnc(N3CCC4(C=C(c5ccc(Cl)cc5Cl)c5ccccc5O4)CC3)s2)n1] | 1.4 nM |
| 12 | 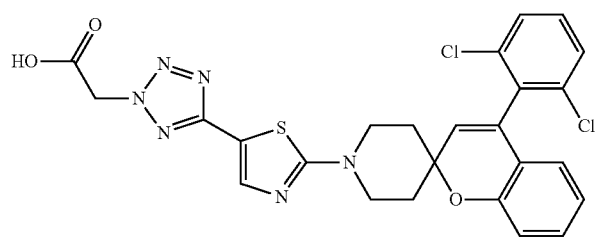 | 1.3 nM |

| Example | Structure | IC$_{50}$ hSCD-1 |
|---------|-----------|------------------|
| 13 | | 0.4 nM | and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. When no number of carbon atoms is specified, $C_{1-6}$ is intended.

The term "alkenyl" shall mean straight or branched-chain alkenes having the specified number of carbon atoms. Examples of alkenyl include vinyl, 1-propenyl, 1-butenyl, 2-butenyl, and the like.

The term "alkynyl" refers to straight or branched-chain alkynes having the specified number of carbon atoms. Examples of alkynyl include ethynyl, propynyl, butynyl, pentynyl, and the like.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means an aromatic monocyclic, bicyclic or tricyclic ring system containing carbon ring atoms. The preferred aryls are monocyclic or bicyclic 6-14 membered aromatic ring systems. Phenyl and naphthyl are preferred aryls. In one embodiment of the present invention, aryl is phenyl and naphthalene. In another embodiment of the present invention, aryl is phenyl. In another embodiment of the present invention, aryl is naphthalene.

"Cycloalkyl" means a non-aromatic monocyclic, bicyclic, tricyclic or bridged saturated carbocyclic ring system, each having the specified number of carbons up to 14 carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

"Cycloheteroalkyl" means a non-aromatic, monocyclic, bicyclic, tricyclic or bridged saturated carbocyclic ring system, each ring having the specified number of carbons up to 14 carbon atoms and containing 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is substituted or unsubstituted piperazine.

"Heteroaryl" means an aromatic or partially aromatic monocyclic, bicyclic, tricyclic or bridged carbocyclic ring system, each ring having the specified number of carbons up to 14 carbon atoms and containing 1, 2, 3, 4 or 5 heteroatoms selected from N, NH, O and S. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, furanyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocycloalkyl and heteroaryl groups, rings and ring systems containing from 3-15 atoms are included, forming 1-3 rings. In one embodiment of the present invention, heteroaryl is furan, benzofuran or dibenzofuran.

The term "5 membered heteroaryl ring" means an aromatic or partially aromatic heterocycle that contains at least one ring heteroatom selected from O, S and N. Examples of 5 membered heteroaryl rings include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, and the like.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term "compounds of structural formula I" includes the compounds of structural formula I, Ia, Ib, Ic, Id, Ie, and If, and pharmaceutically acceptable salts thereof.

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of structural formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural formula I are included in the present invention as well.

The subject compounds are useful in a method of inhibiting the stearoyl-coenzyme A delta-9 desaturase enzyme (SCD) in a patient such as a mammal in need of such inhibition comprising the administration of an effective amount of the compound. The compounds of the present invention are therefore useful to control, prevent, and/or treat conditions and diseases mediated by high or abnormal SCD enzyme activity.

As defined herein, a condition or disease mediated by high or abnormal SCD enzyme activity is defined as any disease or condition in which the activity of SCD is elevated and/or where inhibition of SCD can be demonstrated to bring about symptomatic improvements for the individual so treated. As defined herein, a condition or disease mediated by high or abnormal SCD enzyme activity includes, but is not limited to cardiovascular disease, dyslipidemias, (including but not limiting to disorders of serum levels of triglycerides, hypertriglyceridemia, VLDL, HDL, LDL, cholesterol, and total cholesterol, hypercholesterolemia, as well as cholesterol disorders), familial combined hyperlipidemia, coronary artery disease, atherosclerosis, heart disease, cerebrovascular disease (including but not limited to stroke, ischemic stroke, and transient ischemic attack), peripheral vascular disease, and ischemic retinopathy.

A condition or disease mediated by high or abnormal SCD enzyme activity also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia, and anorexia), weight loss, body mass index and leptin-related diseases.

A condition or disease mediated by high or abnormal SCD enzyme activity also includes fatty liver, hepatic steatosis, hepatitis, non-alcoholic hepatitis, non-alcoholic steatohepatitis, alcoholic hepatitis, acute fatty liver, fatty liver of pregnancy, drug-induced hepatitis, erythrohepatic protporphyria, iron overload disorders, hereditary hemochromatosis, hepatic fibrosis, hepatic cirrhosis, hepatoma and conditions related thereto.

Thus, one aspect of the present invention concerns a method of treating hyperglycemia, diabetes or insulin resistance in a mammalian patient in need of such treatment, which comprises administering to said patient an effective amount of a compound in accordance with structural formula I or a pharmaceutically salt or solvate thereof.

A second aspect of the present invention concerns a method of treating non-insulin dependent diabetes mellitus (Type 2 diabetes) in a mammalian patient in need of such treatment comprising administering to the patient an antidiabetic effective amount of a compound in accordance with structural formula I.

A third aspect of the present invention concerns a method of treating obesity in a mammalian patient in need of such treatment comprising administering to said patient a compound in accordance with structural formula I in an amount that is effective to treat obesity.

A fourth aspect of the invention concerns a method of treating metabolic syndrome and its sequelae in a mammalian patient in need of such treatment comprising administering to said patient a compound in accordance with structural formula I in an amount that is effective to treat metabolic syndrome and its sequelae. The sequelae of the metabolic syndrome include hypertension, elevated blood glucose levels, high triglycerides, and low levels of HDL cholesterol.

A fifth aspect of the invention concerns a method of treating a lipid disorder selected from the group consisting of dyslipidemia, hyperlipidemia, hypertriglyceridemia, hypercholesterolemia, low HDL and high LDL in a mammalian patient in need of such treatment comprising administering to said patient a compound in accordance with structural formula I in an amount that is effective to treat said lipid disorder.

A sixth aspect of the invention concerns a method of treating atherosclerosis in a mammalian patient in need of such treatment comprising administering to said patient a compound in accordance with structural formula I in an amount effective to treat atherosclerosis.

A seventh aspect of the invention concerns a method of treating cancer in a mammalian patient in need of such treatment comprising administering to said patient a compound in accordance with structural formula I in an amount effective to treat cancer.

A further aspect of the invention concerns a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to treat said condition.

Yet a further aspect of the invention concerns a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, and other conditions and disorders where insulin resistance is a component, in a mammalian patient in need of such treatment comprising administering to the patient a compound in accordance with structural formula I in an amount that is effective to delay the onset of said condition.

Yet a further aspect of the invention concerns a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to reduce the risk of developing said condition.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting stearoyl-coenzyme A delta-9 desaturase enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, insulin resistance, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of stearoyl-coenzyme A delta-9 desaturase enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of stearoyl-coenzyme A delta-9 desaturase (SCD) enzyme activity may be demonstrated by the following microsomal and whole-cell based assays:

I. SCD Enzyme Activity Assay:

The potency of compounds of formula I against the stearoyl-CoA desaturase was determined by measuring the conversion of radiolabeled stearoyl-CoA to oleoyl-CoA using rat liver microsome or human SCD1 following previously published procedures with some modifications (Joshi, et al., *J. Lipid Res.*, 18: 32-36 (1977); Talamo, et al., *Anal. Biochem*, 29: 300-304 (1969)). Liver microsome was prepared from male Wistar or Sprague Dawley rats on a high carbohydrate diet for 3 days (LabDiet #5803, Purina). The livers were homogenized (1:10 w/v) in a buffer containing 250 mM sucrose, 1 mM EDTA, 5 mM DTT and 50 mM Tris-HCl (pH 7.5). After a 100,000×g centrifugation for 60 mM, the liver microsome pellet was suspended in a buffer containing 100 mM sodium phosphate, 20% glycerol, 2 mM DTT, and stored at −78° C. Human SCD1 desaturase system was reconstituted using human SCD1 from a baculovirus/Sf9 expression system, cytochrome B5 and cytochrome B5 reductase. Typically, test compound in 2 μL DMSO was incubated for 15 mM at room temperature with 180 μL of the SCD enzyme in a buffer containing 100 mM Tris-HCl (pH 7.5), ATP (5 mM), Coenzyme-A (0.1 mM), Triton X-100 (0.5 mM) and NADH (2 mM). The reaction was initiated by the addition of 20 μL of [$^3$H]-stearoyl-CoA (final concentration=2 μM, radioactivity concentration=1 μCi/mL). After 10 min, the reaction mixture (80 μL) was mixed with a calcium chloride/charcoal aqueous suspension (100 μL charcoal (10% w/v) plus 25 μL CaCl$_2$ (2N). After centrifugation to precipitate the radioactive fatty acid species, tritiated water released from 9,10-[$^3$H]-stearoyl-CoA by the SCD enzyme was quantified on a scintillation counter.

II. Whole Cell-Based SCD (Delta-9), Delta-5 and Delta-6 Desaturase Assays:

Human HepG2 cells were grown on 24-well plates in MEM media (Gibco cat#11095-072) supplemented with 10% heat-inactivated fetal bovine serum at 37° C. under 5% CO$_2$ in a humidified incubator. Test compound dissolved in the media was incubated with the subconfluent cells for 15 min at 37° C. [1-$^{14}$C]-stearic acid was added to each well to a final concentration of 0.05 μCi/mL to detect SCD-catalyzed [$^{14}$C]-oleic acid formation. 0.05 μCi/mL of [1-$^{14}$C]-eicosatrienoic acid or [1-$^{14}$C]-linolenic acid plus 10 μM of 2-amino-N-(3-chlorophenyl)benzamide (a delta-5 desaturase inhibitor) was used to index the delta-5 and delta-6 desaturase activities, respectively. After 4 h incubation at 37° C., the culture media was removed and the labeled cells were washed with PBS (3×1 mL) at room temperature. The labeled cellular lipids were hydrolyzed under nitrogen at 65° C. for 1 h using 400 μL of 2N sodium hydroxide plus 50 μL of L-α-phosphatidylcholine (2 mg/mL in isopropanol, Sigma #P-3556). After acidification with phosphoric acid (60 μL), the radioactive species were extracted with 300 μL of acetonitrile and quantified on a HPLC that was equipped with a C-18 reverse phase column and a Packard Flow Scintillation Analyzer. The levels of [$^{14}$C]-oleic acid over [$^{14}$C]-stearic acid, [$^{14}$C]-arachidonic acid over [$^{14}$C]-eicosatrienoic acid, and [$^{14}$C]-eicosatetraenoic acid (8, 11, 14, 17) over [$^{14}$C]-linolenic acid were used as the corresponding activity indices of SCD, delta-5 and delta-6 desaturase, respectively.

The SCD inhibitors of formula I, including the compounds of Examples 1 to 15, exhibit an SCD inhibition constant IC$_{50}$ of less than 1 μM and more typically less than 0.1 μM.

In Vivo Efficacy of Compounds of the Present Invention:

The in vivo efficacy of compounds of formula I was determined by following the conversion of [1-$^{14}$C]-stearic acid to [1-$^{14}$C]oleic acid in animals as exemplified below. Mice were dosed with a compound of formula I and one hour later the radioactive tracer, [1-$^{14}$C]-stearic acid, was dosed at 20 μCi/kg IV. At 3 h post dosing of the compound, the liver was harvested and then hydrolyzed in 10 N sodium hydroxide for 24 h at 80° C., to obtain the total liver fatty acid pool. After phosphoric acid acidification of the extract, the amount of [1-$^{14}$C]-stearic acid and [1-$^{14}$C]-oleic acid was quantified on a HPLC that was equipped with a C-18 reverse phase column and a Packard Flow Scintillation Analyzer.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of formula I, and either administered separately or in the same pharmaceutical composition, include, but are not limited to:

(a) dipeptidyl peptidase-IV (DPP-4) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (NN-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib;

(s) inhibitors of fructose 1,6-bisphosphatase, such as those disclosed in U.S. Pat. Nos. 6,054,587; 6,110,903; 6,284,748; 6,399,782; and 6,489,476;

(t) acetyl CoA carboxylase-1 and/or -2 inhibitors;

(u) AMPK activators; and (v) agonists of GPR-119.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004).

Specific DPP-IV inhibitor compounds include sitagliptin (MK-0431); vildagliptin (LAF 237); denagliptin; P93/01; saxagliptin (BMS 477118); RO0730699; MP513; SYR-322: ABT-279; PHX1149; GRC-8200; and TS021.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. No. 6,294,534, U.S. Pat. Nos. 6,350,760, 6,376,509, 6,410,548, 6,458,790, 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

One particular aspect of combination therapy concerns a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment comprising administering to the patient a therapeutically effective amount of a compound of structural formula I and an HMG-CoA reductase inhibitor.

More particularly, this aspect of combination therapy concerns a method of treating a condition selected from the group consisting of hypercholesterolemia, atherosclerosis, low HDL levels, high LDL levels, hyperlipidemia, hypertriglyceridemia and dyslipidemia in a mammalian patient in need of such treatment wherein the HMG-CoA reductase inhibitor is a statin selected from the group consisting of lovastatin, simvastatin, pravastatin, cerivastatin, fluvastatin, atorvastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound of structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound of structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin selected from the group consisting of: lovastatin, simvastatin, pravastatin, cerivastatin, fluvastatin, atorvastatin, and rosuvastatin.

In another aspect of the invention, a method for delaying the onset or reducing the risk of developing atherosclerosis in a human patient in need of such treatment is disclosed, wherein the HMG-Co A reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises:
(1) a compound of structural formula I;
(2) a compound selected from the group consisting of:
 (a) dipeptidyl peptidase IV (DPP-IV) inhibitors;
 (b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (NN-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib;

(s) inhibitors of fructose 1,6-bisphosphatase, such as those disclosed in U.S. Pat. Nos. 6,054,587; 6,110,903; 6,284, 748; 6,399,782; and 6,489,476;

(t) acetyl CoA carboxylase-1 and/or -2 inhibitors;

(u) AMPK activators; and (v) agonists of GPR 119; and (3) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of stearoyl-CoA delta-9 desaturase enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Preparation of Compounds of the Invention:

The compounds of structural formula I can be prepared according to the procedures of the following Schemes and Examples, using appropriate materials and are further exemplified by the following specific example. The compound illustrated in the example is not, however, to be construed as forming the only genus that is considered as the invention. The Example further illustrates details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESMS).

List of Abbreviations: ACN is acetonitrile; Ac$_2$O is acetic anhydride; AcOH is acetic acid; Boc is tert-butyloxycarbonyl; Celite™ is diatomaceous earth; conc. is concentrated; CuSO$_4$ is copper sulfate; DBU is 1,8-diazabicyclo[5.4.0]undec-7-ene; DCM is dichloromethane; DIPEA or DIEA is diisopropyl ethyl amine; DME is dimethoxy ethane; DMF is N,N-dimethylformamide; DMSO is dimethyl sulfoxide; dppf is 1,1''-bis(diphenylphosphino)ferrocene; equiv is equivalent(s); ESI is electrospray ionization; Et$_3$N is triethylamine; EtOAc is ethyl acetate; EtOH is ethyl alcohol; Et$_2$O is diethyl ether; g is gram(s); h is hour(s); HCl is hydrochloric acid; i-PrOH is isopropanol; K$_2$CO$_3$ is potassium carbonate; LC is liquid chromatography; L is liter(s); LiHMDS is lithium hexamethyl disilazide; M is molar; min is minute(s); ml or mL is milliliter; mmol is millimole(s); MeOH is methyl alcohol; MgSO$_4$ is magnesium sulfate; MOMCl is chloromethyl methyl ether; MS is mass spectrum; MTBE is methyl tert-butyl ether; N is Normal; NaHMDS is sodium hexamethyl disilazide; NaOH is sodium hydroxide; NaN$_3$ is sodium azide; NMP is N-methyl-2-pyrrolidinone; NMR is nuclear magnetic resonance spectroscopy; Ph is phenyl; PhNTf$_2$ is 1,1,1-trifluoro-N-phenyl-N-[(trifluoromethyl)-sulfonyl] methanesulfonamide; Pd(Ph$_3$)$_4$ is palladium tetrakis triphenyl-phosphine; sat. is saturated; SiO$_2$ is silicon dioxide; rt or RT is room temperature; t-BuOH is tert-butanol; t-BuONO is tert-butyl nitrite; TEA is triethyl amine; Tf is triflate; TFA is trifluoroacetic acid; TFAA is trifluoroacetic anhydride; THF is tetrahydrofuran; TLC is thin layer chromatography; TMP is 2,2,6,6-tetramethylpiperidine; and wt % is weight percent.

Method A

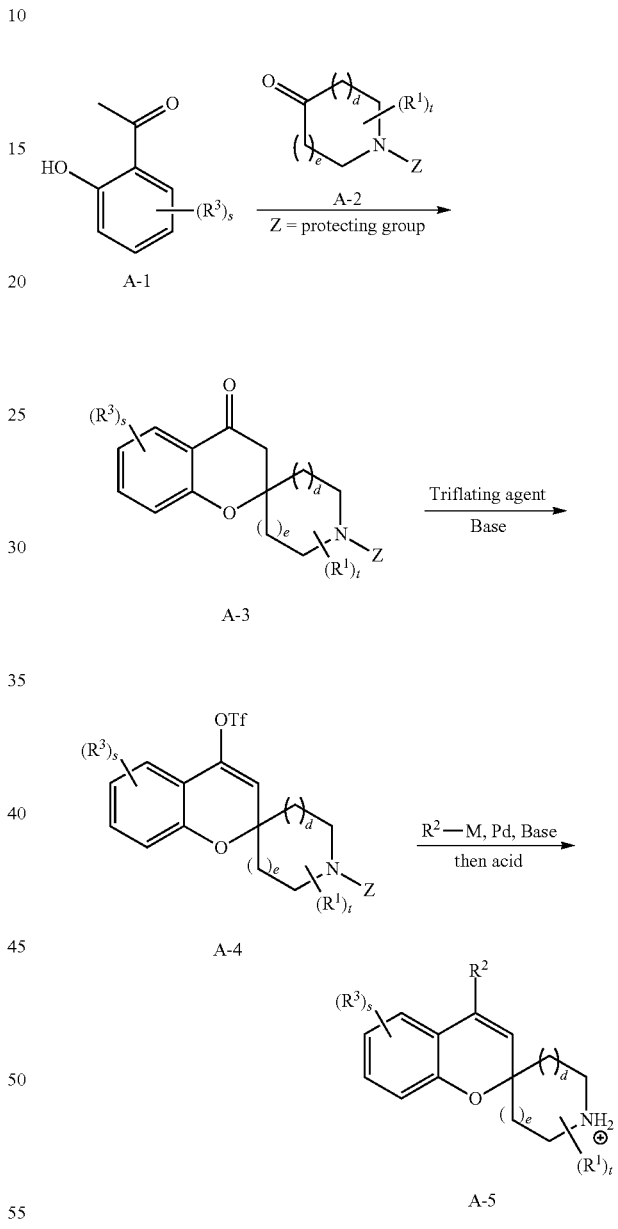

An appropriately substituted 2'-hydroxyacetophenone A-1 is reacted with an appropriately substituted "Z" protected cyclic ketone intermediate A-2 in the presence of a base, such as pyrrolidine, in a solvent, such as methanol, to give the spiro-intermediate A-3. The carbonyl of intermediate A-3 is then reacted with a triflating agent, such as PhNTf$_2$, in the presence of a base, such as LiHMDS, to give the enol triflate A-4. The final amine salt A-5 is obtained in a two step sequence via a coupling reaction between the enol triflate A-4 and an aryl/alkyl organometallic complex R$^2$-M wherein R$^2$ is a previously defined and M is a metal, such as a R$^2$B(OH)$_2$—

MeBF$_3$ complex, in the presence of Pd, such as Pd(PPh$_3$)$_4$, and subsequent removal of the protection group Z under appropriate conditions.

Method B

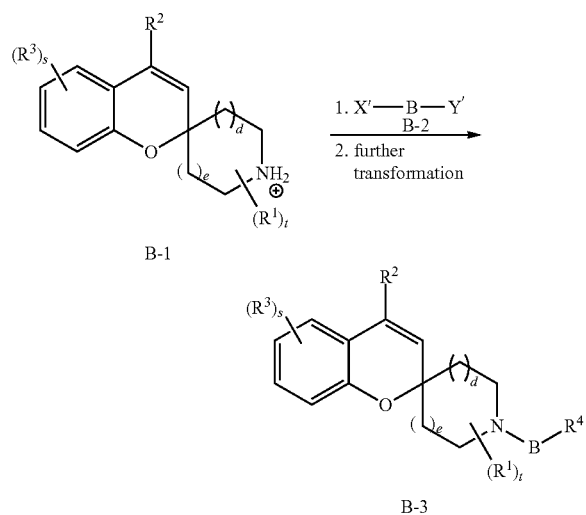

An appropriately substituted spiro intermediate B-1, prepared according to Method A, is reacted with an appropriately halo-substituted (X'=Cl, Br) heteroaryl B-2, wherein heteroaryl ring B is as previously defined, and Y' is a functional group such as halogen (Cl, Br, I), ester, amide, nitrile or heterocycle which is suitable for the transformation to substituent R$^4$ as previously defined. The functional group Y' is then converted by typical standard transformations to substituent R$^4$ to give the desired moiety for final product B-3.

Intermediate 1

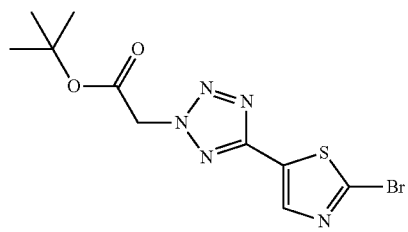 [SMILES: CC(C)(C)OC(=O)Cn1nnc(-c2cnc(Br)s2)n1]

tert-Butyl [5-(2-bromo-1,3-thiazol-5-yl)-2H-tetrazol-2-yl]acetate

Step 1: 2-Bromo-1,3-thiazole-5-carboxamide Into a 2 L round-bottom flask was added ethyl 2-bromothiazole-5-carboxylate (50.0 g, 212 mmol), THF (500 mL) and MeOH (250 mL). To this mixture was added concentrated ammonium hydroxide in water (590 mL) and the reaction mixture was stirred at room temperature for 4 h. The solvents were removed under reduced pressure, and the resulting crude mixture poured into a separatory funnel containing brine (1 L). The aqueous layer was extracted with EtOAc (4×500 mL) and the combined organic layers were washed with brine, dried over Na$_2$SO$_4$, filtered and concentrated under reduced pressure to give the title compound.

Step 2: 2-Bromo-1,3-thiazole-5-carbonitrile Into a 2 L round-bottom flask containing 2-bromo-1,3-thiazole-5-carboxamide (41.5 g, 201 mmol) in CH$_2$Cl$_2$ (1.3 L) was added triethylamine (70 mL, 502 mmol). The resulting solution was cooled to 0° C. and trifluoroacetic anhydride (34 mL, 241 mmol) was added slowly over 15 minutes. The reaction mixture was allowed to warm to room temperature and stirred for 2 h. Then the reaction mixture was poured into a 3 L separatory funnel containing saturated aqueous NaHCO$_3$ solution (500 mL). The aqueous layer was extracted with dichloromethane (2×1.2 L) and the combined organic layers were washed with brine, dried over Na$_2$SO$_4$, filtered and concentrated under reduced pressure. The resulting crude reaction mixture was filtered through a short plug of silica gel on a sintered glass funnel, and washed with copious quantities of EtOAc. The resulting filtrate was concentrated under reduced pressure to provide the title compound.

Step 3: 5-(2-Bromo-1,3-thiazol-5-yl)-2H-tetrazole A solution of 2-bromo-1,3-thiazole-5-carbonitrile (5.00 g, 26.5 mmol) in 2-propanol (75 mL) and water (38 mL) was treated with ZnBr$_2$ (5.96 g, 26.5 mmol) and sodium azide (2.58 g, 39.7 mmol). The reaction mixture was heated at 120° C. for 5 h, then cooled. The cooled reaction mixture was diluted with water (50 mL) and acidified to pH=3 using aqueous 1 M HCl solution (approximately 20 mL). The mixture was poured into a 500 mL separatory funnel and the aqueous layer was extracted with EtOAc (4×100 mL). The combined organic layers were washed with brine, dried over Na$_2$SO$_4$, filtered and concentrated under reduced pressure to provide the title compound.

Step 4: tert-Butyl [5-(2-bromo-1,3-thiazol-5-yl)-2H-tetrazol-2-yl]acetate Into a 250 mL round-bottom flask containing 5-(2-bromo-1,3-thiazol-5-yl)-2H-tetrazole (5.43 g, 22.5 mmol) in THF (81 m) was added triethylamine (7.2 mL, 52 mmol) and tert-butyl bromoacetate (34 mmol). The resulting mixture was heated at 80° C. for 1 h, and then cooled to room temperature. Then the reaction mixture was poured into a separatory funnel containing water (80 mL) and the aqueous layer was extracted with EtOAc (2×160 mL). The combined organic layers were washed with brine, dried over Na$_2$SO$_4$, filtered and concentrated under reduced pressure. Purification by column chromatography through silica gel, eluting with 100% hexanes to 50:50 hexanes:EtOAc as a gradient, provided the title compound as a single regioisomer. $^1$H NMR (CDCl$_3$, 400 MHz) 8.22 (1H, s), 5.32 (2H, s), 1.47 (9H, s). MS (ESI, Q$^+$) m/z 346, 348 (M+1, $^{79}$Br, $^{81}$Br).

Intermediate 2

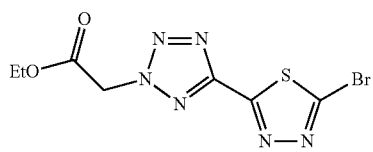 [SMILES: CCOC(=O)Cn1nnc(-c2nnc(Br)s2)n1]

Ethyl [5-(5-bromo-1,3,4-thiadiazol-2-yl)-2H-tetrazol-2-yl]acetate

Step 1: Ethyl 5-bromo-1,3,4-thiadiazole-2-carboxylate To a suspension of ethyl 5-amino-1,3,4-thiadiazole-2-carboxylate in CH$_3$CN (0.32 M) was added CuBr$_2$ (2 equiv). The mixture turned dark green and was stirred for 15 min at room temperature. Then t-BuONO (2 equiv, 90%) was added dropwise over 15-20 min. The mixture became slightly warm and gas evolved after about 5 min and then throughout the addition. After completion of the addition and after gas evolution subsided, the mixture was heated at 60° C. for 30 min. Solvent was then evaporated in vacuo. Water and EtOAc were added and the mixture was stirred until the dark green color disappeared. The mixture was filtered through Celite™ and washed with EtOAc. The EtOAc layer was separated, washed with diluted brine, dried ($Na_2SO_4$) and concentrated to give the title compound. $^1$H NMR (400 MHz, acetone-$d_6$): δ 4.52 (q, 2H), 1.43 (t, 3H).

Step 2: 5-Bromo-1,3,4-thiadiazole-2-carboxamide To a solution of ethyl 5-bromo-1,3,4-thiadiazole-2-carboxylate in THF (1.1 M) at room temperature was added concentrated $NH_4OH$ (2.9 equiv). The mixture was stirred at room temperature overnight and a precipitate appeared in the aqueous layer. Then the volatile solvent was removed in vacuo. The resulting mixture was diluted with water and the precipitate was collected, washed with water and dried under vacuum to give the title compound.

Step 3: 5-Bromo-1,3,4-thiadiazole-2-carbonitrile To a solution of 5-bromo-1,3,4-thiadiazole-2-carboxamide and $Et_3N$ (2.3 equiv) in THF (0.5 M) at 0° C. was added TFAA (1.1 equiv). The mixture was then warmed to room temperature and stirred for 30 min, then the solvent was evaporated in vacuo. The resulting residue was diluted with water. The resulting precipitate was collected, washed with water, and dried to give the title compound.

Step 4: Ethyl [5-(5-bromo-1,3,4-thiadiazol-2-yl)-2H-tetrazol-2-yl]acetate To a suspension of 5-bromo-1,3,4-thiadiazole-2-carbonitrile (1 g, 5 mmol) and $ZnBr_2$ (1.1 g, 5 mmol) in i-PrOH (10 mL) and $H_2O$ (5 mL) was added $NaN_3$ (0.65 g, 10 mmol) in a sealed tube. The mixture was stirred at 120° C. overnight and then cooled to room temperature. The mixture was adjusted to pH=4 with HCl (2 M) and extracted with EtOAc (3×50 mL). The combined organic layers was dried over $Na_2SO_4$, filtered and concentrated in vacuo to afford the crude 5-(5-bromo-1,3,4-thiadiazol-2-yl)-1H-tetrazole.

Step 5: Ethyl [5-(5-bromo-1,3,4-thiadiazol-2-yl)-2H-tetrazol-2-yl]acetate To a solution of 5-(5-bromo-1,3,4-thiadiazol-2-yl)-1H-tetrazole (1 g, 4.3 mmol) in DMF (20 mL) was added $Cs_2CO_3$ (2.1 g, 6.45 mmol) and ethyl bromoacetate (0.95 mL, 8.6 mmol). The resulting solution was stirred at 90° C. for 1 hour. Then the solution was partitioned between EtOAc (100 mL) and water (200 mL). The combined organic layers were dried over anhydrous $Na_2SO_4$, filtered and evaporated in vacu. to give the crude product. Chromatography of the crude product over silica afforded the title compound as a white solid, contaminated with the 1-alkylated isomer ethyl [5-(5-bromo-1,3,4-thiadiazol-2-yl)-1H-tetrazol-1-yl]acetate. $^1$HNMR (CDCl$_3$, 300 MHz): δ 5.70 (s, 2H), 4.26 (q, 2H), 1.28 (t, 3H).

Intermediate 3

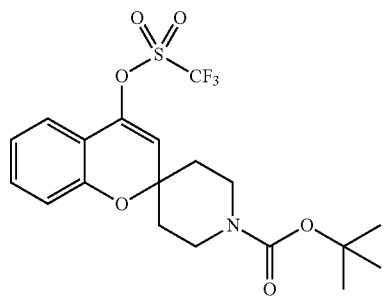 [SMILES: CC(C)(C)OC(=O)N1CCC2(C=C(OS(=O)(=O)C(F)(F)F)c3ccccc3O2)CC1]

tert-Butyl-4-{[(trifluoromethyl)sulfonyl]oxy}-1'H-spiro[chromene-2,4'-piperidine]-1'-carboxylate Step 1: tert-Butyl-4-oxo-3,4-dihydro-1'H-spiro[chromene-2,4'-piperidine]-1'-carboxylate To a solution of benzophenone (11.3 g, 83 mmol) in methanol (151 mL) was added pyrrolidine (7.47 mL, 90 mmol). After 5 min, Boc-piperidinone (15 g, 75 mmol) was added and the mixture stirred at 85° C. for 3 h. The reaction mixture was then cooled down to room temperature and concentrated under reduced pressure. The resulting oily residue was purified by Combiflash™ chromatography ($SiO_2$ (120 g), eluting with 5-60% EtOAc/hexanes over 40 min) to afford the title compound as an oil.

Step 2: tert-Butyl-4-{[(trifluoromethyl)sulfonyl]oxy}-1'H-spiro[chromene-2,4'-piperidine]-1'-carboxylate To a solution of tert-butyl-4-oxo-3,4-dihydro-1'H-spiro[chromene-2,4'-piperidine]-1'-carboxylate (8.8 g, 27.7 mmol) and $PhNTf_2$ (12.9 g, 36.0 mmol) in dry THF (184 mL) was added LiHMDS (36.0 mL, 36.0 mmol) at −78° C. After the addition was completed the mixture was stirred at 0° C. for 1 h. Then the reaction mixture was quenched with saturated $NaHCO_3$ (100 mL), diluted with ether (75 mL). The layers were separated and the organic layer was washed with 1N NaOH (50 mL), dried over $MgSO_4$, filtered and concentrated under reduced pressure. The resulting pale oily residue was purified by Combiflash™ chromatography ($SiO_2$ (50 g), eluting with 5-40% EtOAc/hexanes over 40 min) to afford the title compound as an oil. $^1$H NMR (500 MHz, DMSO-$d_6$): δ 7.36 (t, 1H), 7.22 (d, 1H), 7.07 (t, 1H), 7.03 (d, 1H), 6.14 (s, 1H), 3.74 (d, 2H), 3.25-3.16 (m, 2H), 1.91 (d, 2H), 1.81-1.71 (m, 2H), 1.42 (s, 9H). MS (+ESI) m/z 472.0 (MNa$^+$).

Intermediate 4

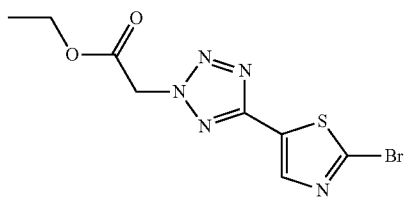 [SMILES: CCOC(=O)Cn1nnc(-c2cnc(Br)s2)n1]

Ethyl [5-(2-bromo-1,3-thiazol-5-yl)-2H-tetrazol-2-yl]acetate

Step 1: 2-Bromo-1,3-thiazole-5-carboxamide Into a 2 L round-bottom flask was added ethyl 2-bromothiazole-5-carboxylate (50.0 g, 212 mmol), THF (500 mL) and MeOH (250 mL). To this mixture was added concentrated ammonium hydroxide in water (590 mL) and the reaction mixture was stirred at room temperature for 4 h. Then the solvents were removed under reduced pressure, and the resulting crude mixture was poured into a separatory funnel containing brine (1 L). The aqueous layer was extracted with EtOAc (4×500 mL). The combined organic layers were washed with brine, dried over $Na_2SO_4$, filtered and concentrated under reduced pressure to give the title compound.

Step 2: 2-Bromo-1,3-thiazole-5-carbonitrile Into a 2 L round-bottom flask containing 2-bromo-1,3-thiazole-5-carboxamide (41.5 g, 201 mmol) in $CH_2Cl_2$ (1.3 L) was added triethylamine (70 mL, 502 mmol). The resulting solution was cooled to 0° C. and trifluoroacetic anhydride (34 mL, 241 mmol) was added slowly over 15 minutes. Then the reaction mixture was allowed to warm to room temperature and stirred for 2 h. The reaction mixture was then poured into a 3 L separatory funnel containing saturated aqueous $NaHCO_3$ solution (500 mL). The aqueous layer was extracted with dichloromethane (2×1.2 L) and the combined organic layers were washed with brine, dried over $Na_2SO_4$, filtered and concentrated under reduced pressure. The resulting crude reaction mixture was filtered through a short plug of silica gel on a sintered glass funnel, and washed with copious quantities of EtOAc. The resulting filtrate was concentrated under reduced pressure to provide the title compound.

Step 3: 5-(2-Bromo-1,3-thiazol-5-yl)-2H-tetrazole A solution of 2-bromo-1,3-thiazole-5-carbonitrile (5.00 g, 26.5 mmol) in 2-propanol (75 mL) and water (38 mL) was treated with $ZnBr_2$ (5.96 g, 26.5 mmol) and sodium azide (2.58 g, 39.7 mmol). The reaction mixture was heated at 120° C. for 5 h. Then the cooled reaction mixture was diluted with water (50 mL) and acidified to pH=3 using aqueous 1 M HCl solution (approximately 20 mL). The mixture was poured into a 500 mL separatory funnel and the aqueous layer was extracted with EtOAc (4×100 mL). The combined organic layers were washed with brine, dried over $Na_2SO_4$, filtered and concentrated under reduced pressure to provide the title compound.

Step 4: Ethyl [5-(2-bromo-1,3-thiazol-5-yl)-2H-tetrazol-2-yl]acetate Into a 250 mL round-bottom flask containing 5-(2-bromo-1,3-thiazol-5-yl)-2H-tetrazole (5.43 g, 22.5 mmol) in THF (81 mL) was added triethylamine (7.2 mL, 52 mmol) and ethyl bromoacetate (3.8 mL, 34 mmol). The resulting mixture was heated at 80° C. for 1 h, and then cooled to room temperature. Then the reaction mixture was poured into a separatory funnel containing water (80 mL) and the aqueous layer was extracted with EtOAc (2×160 mL). The combined organic layers were washed with brine, dried over $Na_2SO_4$, filtered and concentrated under reduced pressure. Purification by column chromatography through silica gel, eluting with 100% hexanes to 50:50 hexanes:EtOAc as a gradient, provided the title compound as a single regioisomer. $^1$H NMR ($d_6$-DMSO, 400 MHz) 8.39 (1H, s), 5.93 (2H, s), 4.21 (2H, q), 1.22 (3H, t).

Intermediate 5

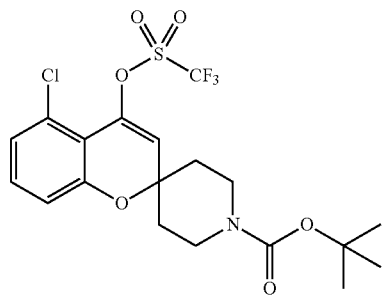 [SMILES: CC(C)(C)OC(=O)N1CCC2(C=C(OS(=O)(=O)C(F)(F)F)c3c(Cl)cccc3O2)CC1]

tert-Butyl 5-chloro-4-{[(trifluoromethyl)sulfonyl]oxy}-1'H-spiro[chromene-2,4'-piperidine]-1'-carboxylate Step 1: 1-Chloro-3-(methoxymethoxy)benzene To a solution of 3-chlorophenol (20 g, 0.16 mol) in DCM (200 mL) was added DIPEA (247 g, 1.72 mol), followed by MOMCl (125 g, 1.56 mol). The reaction mixture was stirred at room temperature for 4 h, quenched with water and extracted with DCM (3×80 mL). The combined organic layers were washed with brine and dried over anhydrous $Na_2SO_4$. Then the solvent was removed under reduced pressure and the residue was purified by silica gel chromatography to afford the title compound.

Step 2: 1-[2-Chloro-6-(methoxymethoxy)phenyl]ethanone To a solution of 1-chloro-3-(methoxymethoxy)benzene (16 g, 0.093 mol) in THF (160 mL) stirring at −75° C. was added TMP (14.1 g, 0.1 mol) and n-BuLi (40 mL, 0.1 mol, 2.5 M in hexane) dropwise over 30 min. After stirring for a further 2 h at −75° C., $Ac_2O$ (10.44 g, 0.1 mol) was added dropwise at −75° C. over 30 min. The reaction mixture was stirred at room temperature for 30 min, then quenched with 10 mL of water and extracted with EtOAc (3×80 mL). The combined organic layers were washed with brine and dried over anhydrous $Na_2SO_4$. The solvent was removed under reduced pressure and the resulting residue was purified by silica gel chromatography to afford the title compound.

Step 3: 1-(2-Chloro-6-hydroxyphenyl)ethanone To a solution of 1-[2-chloro-6-(methoxymethoxy)phenyl]ethanone (9.5 g, 0.044 mol) in THF (100 mL) was added concentrated HCl (9 g, 0.088 mol, M=12). The resulting mixture was stirred at 65° C. for 3 h, quenched with water (30 mL) and extracted with EtOAc (3×50 mL). The combined organic layers were washed with brine (30 mL) and dried over anhydrous $Na_2SO_4$. The solvent was removed under reduced pressure and the residue was purified by silica gel chromatography to afford the title compound.

Step 4: tert-Butyl 5-chloro-4-oxo-3,4-dihydro-1'H-spiro[chromene-2,4'-piperidine]-1'-carboxylate Into a 100 mL 3-necked round bottom flask was dissolved tert-butyl 4-oxopiperidine-1-carboxylate (5 g, 25.3 mmol) and pyrrolidine (2.52 g, 35 mmol) in methanol (50 mL). After 5 min, 1-(2-chloro-6-hydroxyphenyl)ethanone (4.3 g, 25.3 mmol) was added and the reaction mixture was stirred for 1 hour at 65° C.

The reaction mixture was then allowed to cool to room temperature, and concentrated under reduced pressure. To the resulting residue was added 100 mL of ethyl acetate, and the resulting solution was washed with water (2×50 mL). The organic layer was separated, dried over anhydrous sodium sulfate and concentrated under reduced pressure. The resulting residue was purified by silica gel chromatography to afford the title compound.

Step 5: tert-Butyl 5-chloro-4-{[(trifluoromethyl)sulfonyl]oxy}-1'H-spiro[chromene-2,4'-piperidine]-1'-carboxylate To a solution of tert-butyl 5-chloro-4-oxo-3,4-dihydro-1'H-spiro[chromene-2,4'-piperidine]-1'-carboxylate (4 g, 11.4 mmol) in THF (60 mL) was added dropwise NaHMDS (7.2 mL, 14.8 mmol) at −78° C. The reaction mixture was stirred at −78° C. for 2 h, then a solution of PhNTf$_2$ (5.28 g, 14.8 mmol) in THF (20 mL) was added dropwise. The resulting mixture was stirred at −78° C. over 30 min, then warmed to 0° C. and stirred for 1 h. Then the reaction mixture was quenched with saturated NH$_4$Cl (10 mL), and extracted with EtOAc (3×50 mL). The combined organic layers were washed with brine (20 mL), dried over Na$_2$SO$_4$ and concentrated under reduced pressure. The resulting residue was purified by silica gel chromatography (Petroleum ether/Ethyl Acetate=10/1) to afford the title compound. $^1$H NMR (CDCl$_3$ 400 MHz) δ 7.15-7.19 (m, 1H), 7.00-7.02 (m, 1H), 6.85-6.88 (m, 1H), 5.71 (s, 1H), 3.80-3.83 (m, 2H), 3.21-3.27 (m, 2H), 2.02-2.06 (m, 2H), 1.68-1.72 (m, 2H), 1.46 (s, 9H).

Intermediate 6

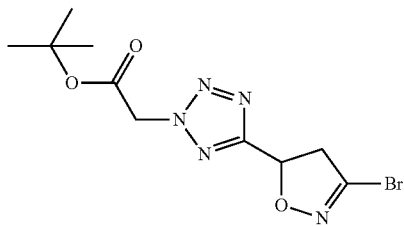 [SMILES: CC(C)(C)OC(=O)Cn1nnc(C2CC(Br)=NO2)n1]

tert-Butyl [5-(3-bromo-4,5-dihydroisoxazol-5-yl)-2H-tetrazol-2-yl]acetate

Step 1: Ethyl 3-bromo-4,5-dihydroisoxazole-5-carboxylate To a round-bottom flask containing hydroxycarbonimidic dibromide (100 g, 490 mmol) was slowly added DMF (300 mL) followed by ethyl acrylate (59 g, 590 mmol). The mixture was cooled to −10° C. and then a solution of KHCO$_3$ (99 g, 990 mmol) in water (400 mL) was added dropwise over 90 min, at a rate which maintained the internal temperature below 0° C. Stirring was continued at 0° C. for 1.5 h. Then the reaction mixture was poured into a 4 L separatory funnel containing water (500 mL) and the aqueous layer was extracted with MTBE (3×500 mL). The combined organic layers were washed with brine, dried over MgSO$_4$, filtered and concentrated under reduced pressure to give a yellow oil which was used directly in Step 2.

Step 2: 3-Bromo-4,5-dihydroisoxazole-5-carboxamide Ethyl 3-bromo-4,5-dihydroisoxazole-5-carboxylate (109 g, 490 mmol) was added to a 1 L round-bottom flask containing 2.0 M NH$_3$ in MeOH (295 mL). The reaction mixture was heated at 50° C. for 2.5 h and then cooled to room temperature and stirred overnight for 16 h. The resulting slurry was diluted with 500 mL of diethyl ether and stirred in an ice-bath for 1 h. The product was isolated by filtration under vacuum, affording the title compound as a tan solid. $^1$H NMR (CDCl$_3$, 400 MHz): δ 6.70 (1H, bs), 5.92 (1H, bs), 5.06 (1H, dd, J=11.0, 6.5 Hz), 3.64-3.51 (2H, m). MS (ESI, Q$^+$) m/z 193, 195 (M+1, $^{79}$Br, $^{81}$Br).

Step 3: 3-Bromo-4,5-dihydroisoxazole-5-carbonitrile To a solution of 3-bromo-4,5-dihydroisoxazole-5-carboxamide (30.0 g, 155 mmol) in THF (360 mL) was added triethylamine (43.0 mL, 311 mmol). The solution was cooled to 0° C. and TFAA (33.0 mL, 233 mmol) was added slowly over 20 min, at a rate which maintained the internal temperature below 15° C. The reaction mixture was stirred at 0° C. for 1 h. The reaction mixture was poured into a 2 L separatory funnel containing water (500 mL) and the aqueous layer was extracted with MTBE (3×500 mL). The combined organic layers were washed with a saturated aqueous NaHCO$_3$ solution (2×250 mL) and brine, dried over MgSO$_4$, filtered and concentrated under reduced pressure to afford the title compound.

Step 4: 5-(3-Bromo-4,5-dihydroisoxazol-5-yl)-2H-tetrazole To a 2 L round-bottom flask equipped with a reflux condenser, heating mantle, under N$_2$, was added 3-bromo-4,5-dihydroisoxazole-5-carbonitrile (39.4 g, 225 mmol), zinc oxide (1.8 g, 23 mmol), THF (40 mL) and water (200 mL). To this solution was added slowly a solution of sodium azide (16 g, 250 mmol) in water (10 mL) over 5 min and the mixture was warmed to 75° C. for 16 h. Heating was applied at a rate at which the internal temperature of the reaction mixture did not exceed 80° C. The reaction mixture was cooled to 0° C. and acidified to pH 3-4 with the slow addition of 2 N aqueous HCl solution. During the acidification, the internal temperature was maintained below 5° C. The reaction mixture was poured into a 2 L separatory funnel and the aqueous layer was extracted with EtOAc (3×500 mL). The combined organic layers were washed with brine, dried over MgSO$_4$, filtered and concentrated under reduced pressure to afford the title compound.

Step 5: tert-Butyl [5-(3-bromo-4,5-dihydroisoxazol-5-yl)-2H-tetrazol-2-yl]acetate To a 2 L round-bottom flask equipped with a reflux condenser, heating mantle, under N$_2$, was added 5-(3-bromo-4,5-dihydroisoxazol-5-yl)-2H-tetrazole (49 g, 225 mmol) and THF (500 mL). Triethylamine (53 mL, 383 mmol) was added to the mixture and the solution was heated to 55° C. while tert-butyl bromoacetate (66 g, 338 mmol) was added. The mixture was heated at 55° C. for 1 h and then cooled to room temperature. The reaction mixture was poured into a 2 L reparatory funnel containing 1 N aqueous HCl solution (500 mL) and the aqueous layer was extracted with EtOAc (3×500 mL). The combined organic layers were washed with brine, dried over MgSO$_4$, filtered and concentrated under reduced pressure. Purification by column chromatography through Iatrobead™ silica gel, eluting with 75:15:5 hexanes/EtOAc/CH$_2$Cl$_2$, afforded the title product in a greater than 10:1 regioisomeric purity. $^1$H NMR (CDCl$_3$, 400 MHz): δ 5.98 (1H, dd, J=11.0, 7.5 Hz), 5.35 (2H, s), 3.87 (1H, dd, J=17.5, 7.5 Hz), 3.70 (1H, dd, J=17.5, 11.0 Hz), 1.50 (9H, s). MS (ESI, Q⁺) m/z 332, 334 (M+1, $^{79}$Br, $^{81}$Br).

Intermediate 7

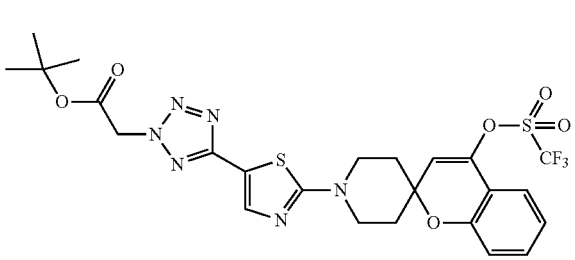 [SMILES: CC(C)(C)OC(=O)Cn1nnc(-c2cnc(N3CCC4(C=C(OS(=O)(=O)C(F)(F)F)c5ccccc5O4)CC3)s2)n1]

tert-Butyl {5-[2-(4-{[(trifluoromethyl)sulfonyl]oxy}-1'H-spiro[chromene-2,4'-piperidin]-1-yl)-1,3-thiazol-5-yl]-2H-tetrazol-2-yl}acetate Step 1: 4-Oxo-3,4-dihydrospiro[chromene-2,4'-piperidinium]chloride. To a solution of tert-butyl-4-oxo-3,4-dihydro-1'H-spiro[chromene-2,4'-piperidine]-1'-carboxylate (40.7 g, 128 mmol) (Intermediate 3, step 1) in DCM (128 ml) was added 4M HCl in dioxane (39.0 ml, 1282 mmol) dropwise. After 2 minutes at room temperature, a precipitate began to form. The mixture was stirred for an additional 2 h. Then the volatiles were evaporated under reduced pressure. The resulting solid was resuspended in ether and hexanes (1:1), filtered, washed with ether/hexanes and dried under vacuum for 1 h under mild heating to give the title compound as solid.

Step 2: tert-Butyl {5-[2-(4-oxo-3,4-dihydro-1H-spiro[naphthalene-2,4'-piperidin]-1'-yl)-1,3-thiazol-5-yl]-2H-tetrazol-2-yl}acetate To a solution of Intermediate 1 (15 g, 43.3 mmol) in NMP (217 ml) was added 4-oxo-3,4-dihydrospiro[chromene-2,4'-piperidinium]chloride (12.54 g, 49.8 mmol), followed by DBU (19.44 ml, 130 mmol). The reaction was heated to 130° C. for 20 min. The reaction was cooled, diluted with 1N HCl and extracted 2× with EtOAc. The combined organic layers were further washed with 1N HCl (1×); water (2×), dried (Na₂SO₄), filtered and concentrated under pressure. The residue was triturated with Et₂O/CH₂Cl₂/hexanes, filtered and the resulting solid was washed with hexanes and dried to afford the title compound as a solid.

Step 3: tert-Butyl {5-[2-(4-{[(trifluoromethyl)sulfonyl]oxy}-1'H-spiro[chromene-2,4'-piperidin]-1'-yl)-1,3-thiazol-5-yl]-2H-tetrazol-2-yl}acetate The title compound was prepared in a similar manner as that described for Example 5 (Step 5) from tert-butyl {5-[2-(4-oxo-3,4-dihydro-1H-spiro[naphthalene-2,4'-piperidin]-1'-yl)-1,3-thiazol-5-yl]-2H-tetrazol-2-yl}acetate and PhNTf₂. ¹H NMR (500 MHz, CDCl₃): δ 7.94 (s, 1H), 7.33-7.31 (m, 2H), 7.04 (t, 1H), 6.96 (d, 1H), 5.61 (s, 1H), 5.32 (s, 2H), 3.92 (d, 2H), 3.63 (t, 2H), 2.28 (d, 2H), 1.92 (dt, 2H), 1.58 (s, 9H). MS (+ESI) m/z 615.1 (MO.

Example 1

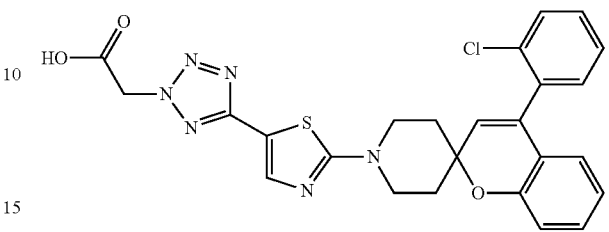

(5-{2-[4-(2-Chlorophenyl)-1'H-spiro[chromene-2,4'-piperidin]-1'-yl]-1,3-thiazol-5-yl}-2H-tetrazol-2-yl) acetic acid Step 1: 4-(2-Chlorophenyl)spiro[chromene-2,4'-piperidine]hydrochloride To a mixture of (2-chlorophenyl)boronic acid (209 mg, 1.34 mmol), palladium tetrakis triphenylphosphine (116 mg, 0.10 mmol) and potassium carbonate (231 mg, 1.67 mmol) under N₂ was added a degassed solution of Intermediate 3 (300 mg, 0.67 mmol) in DME (2.96 mL) and tert-butanol (1.48 mL). The reaction mixture was stirred at an external temperature of 86° C. for 16 h. Then the reaction mixture was cooled down to room temperature, diluted with DCM (5 mL) and saturated NaHCO₃ (15 mL) and passed trough a cartridge separator. The aqueous layer was washed in the cartridge with DCM (2×5 mL), and the combined organic layers were evaporated under reduced pressure. The resulting residue was purified by Combiflash™ chromatography (SiO₂ (12 g), eluting with 0-30% EtOAc/hexanes over 40 min). The resulting intermediate was diluted with 4N HCl in dioxane (5 mL) and placed in a round bottom flask equipped with a condenser. The reaction mixture was heated periodically (every 10 min) to reflux using a heat gun for a total of 30 min. Then the volatiles were evaporated under reduced pressure to afford the title compound as a solid.

Step 2: tert-Butyl(5-{2-[4-(2-chlorophenyl)-1'H-spiro[chromene-2,4'-piperidin]-1'-yl]-1,3-thiazol-5-yl}-2H-tetrazol-2-yl)acetate To a solution of Intermediate 1 (90 mg, 0.26 mmol) and 4-(2-chlorophenyl)spiro[chromene-2,4'-piperidine]hydrochloride (100 mg, 0.29 mmol) in NMP (1.3 mL) was added DBU (118 µl, 0.78 mmol). The mixture was directly warmed to 130° C. for 30 min, then rapidly cooled to −78° C., and then warmed to room temperature. The reaction mixture was diluted with water (5 mL) and 1N HCl (5 mL), then extracted with EtOAc (3×3 mL). The combined organic layers were washed with 1N HCl (10 mL), water (10 mL), brine (10 mL), dried with MgSO₄, filtered and evaporated under reduced pressure. The resulting residue was purified by Combiflash™ chromatography (SiO₂ (12 g), eluting with 5-40% EtOAc/hexanes over 40 min) to afford the title compound as a solid.

Step 3: (5-{2-[4-(2-Chlorophenyl)-1'H-spiro[chromene-2,4'-piperidin]-1'-yl]-1,3-thiazol-5-yl}-2H-tetrazol-2-yl)acetic acid To a solution of tert-butyl(5-{2-[4-(2-chlorophenyl)-1'H-spiro[chromene-2,4'-piperidin]-1'-yl]-1,3-thiazol-5-yl}-2H-tetrazol-2-yl)acetate (105 mg, 0.18 mmol) in THF (5 mL) and water (1 mL) was added LiOH (18.7 mg, 0.78 mmol). The reaction mixture was stirred at room temperature for 1 h. The reaction mixture was concentrated under reduced pressure.

The resulting residue was acidified with 1N HCl, extracted with EtOAc (3×5 mL), dried with MgSO₄, filtered and evaporated under reduced pressure. The resulting residue was purified by trituration using DCM/hexanes (1/10) to give the title compound as a solid. ¹H NMR (500 MHz, DMSO-d₆): δ 7.89 (s, 1H), 7.59-7.57 (m, 2H), 7.47-7.44 (m, 3H), 7.37-7.35 (m, 2H), 7.20 (t, 2H), 7.00 (d, 2H), 6.85 (t, 2H), 6.53 (d, 2H), 5.83 (s, 2H), 5.68 (s, 4H), 3.87 (d, 4H), 3.67-3.57 (m, 6H), 2.11-2.06 (m, 3H), 2.01-1.95 (m, 4H). MS (+ESI) m/z 521.0 (MH⁺).

Example 2

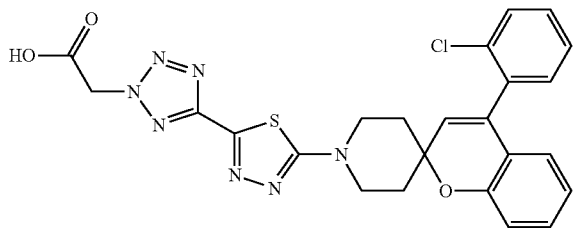 [SMILES: O=C(O)Cn1nnc(-c2nnc(N3CCC4(C=C(c5ccccc5Cl)c5ccccc5O4)CC3)s2)n1]

(5-{5-[4-(2-Chlorophenyl)-1'H-spiro[chromene-2,4'-piperidin]-1'-yl]-1,3,4-thiadiazol-2-yl}-2H-tetrazol-2-yl)acetic acid Step 1: Ethyl(5-{5-[4-(2-chlorophenyl)-1'H-spiro[chromene-2,4'-piperidin]-1'-yl]-1,3,4-thiadiazol-2-yl}-2H-tetrazol-2-yl)acetate To a solution of Intermediate 2 (65 mg, 0.204 mmol) and 4-(2-chlorophenyl)spiro[chromene-2,4'-piperidine]hydrochloride (74.5 mg, 0.214 mmol) (Example 1, Step 1) in THF (1.02 mL) was added TEA (85 µl, 0.61 mmol). The reaction mixture was heated to 70° C. for 16 h. Then the volatiles were evaporated under reduced pressure. The resulting mixture was diluted with water (5 mL) and 1N HCl (5 mL), then extracted with EtOAc (3×3 mL). The combined organic layers were dried with MgSO₄, filtered and evaporated under reduced pressure. The resulting residue was purified by Combiflash™ chromatography (SiO₂ (12 g), eluting with 5-40% EtOAc/hexanes over 40 min) to afford the title compound as a solid.

Step 2: (5-{5-[4-(2-Chlorophenyl)-1'H-spiro[chromene-2,4'-piperidin]-1'-yl]-1,3,4-thiadiazol-2-yl}-2H-tetrazol-2-yl)acetic acid The title compound was prepared in a similar manner as that described for Example 1 (Step 3) from ethyl (5-{5-[4-(2-chlorophenyl)-1'H-spiro[chromene-2,4'-piperidin]-1'-yl]-1,3,4-thiadiazol-2-yl}-2H-tetrazol-2-yl)acetate and LiOH at room temperature. ¹H NMR (500 MHz, DMSO-d₆): δ 7.59-7.57 (m, 1H), 7.46 (ddd, 2H), 7.37-7.35 (m, 1H), 7.21-7.19 (m, 1H), 7.01 (d, 1H), 6.88-6.84 (m, 1H), 6.54 (d, 1H), 5.83 (s, 3H), 3.89 (s, 2H), 3.73 (s, 2H), 2.17-2.09 (m, 2H), 2.01 (d, 2H). MS (+ESI) m/z 522.1 (MH⁺).

Example 3

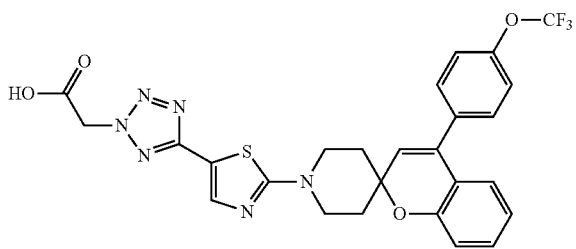 [SMILES: O=C(O)Cn1nnc(-c2cnc(N3CCC4(C=C(c5ccc(OC(F)(F)F)cc5)c5ccccc5O4)CC3)s2)n1]

[5-(2-{-4-[4-(Trifluoromethoxy)phenyl]-1'H-spiro [chromene-2,4'-piperidin]-1'-yl}-1,3-thiazol-5-yl)-2H-tetrazol-2-yl]acetic acid Step 1: 4-[4-(Trifluoromethoxy)phenyl]spiro[chromene-2,4'-piperidine]hydrochloride The title compound was prepared in a similar manner as that described for Example 1 (Step 1) from Intermediate 3 and [4-(trifluoromethoxy)phenyl]boronic acid.

Step 2: tert-Butyl[5-(2-{4-[4-(trifluoromethoxy)phenyl]-1'H-spiro[chromene-2,4'-piperidin]-1'-yl}-1,3-thiazol-5-yl)-2H-tetrazol-2-yl]acetate The title compound was prepared in a similar manner as that described for Example 1 (Step 2) from 4-[4-(trifluoromethoxy)phenyl]-spiro[chromene-2,4'-piperidine]hydrochloride and Intermediate 1.

Step 3: [5-(2-{4-[4-(Trifluoromethoxy)phenyl]-1'H-spiro[chromene-2,4'-piperidin]-1'-yl}-1,3-thiazol-5-yl)-2H-tetrazol-2-yl]acetic acid The title compound was prepared in a similar manner as that described for Example 1 (Step 3) from tert-butyl[5-(2-{4-[4-(trifluoromethoxy)-phenyl]-1'H-spiro[chromene-2,4'-piperidin]-1'-yl}-1,3-thiazol-5-yl)-2H-tetrazol-2-yl]acetate and LiOH at room temperature. ¹H NMR (500 MHz, DMSO-d₆): δ 7.89 (s, 1H), 7.51 (d, 2H), 7.45 (d, 2H), 7.28-7.24 (m, 1H), 7.05 (d, 1H), 6.98-6.93 (m, 2H), 5.94 (s, 1H), 5.69 (s, 2H), 3.87 (d, 2H), 3.65-3.58 (m, 2H), 2.05 (d, 2H), 2.01-1.93 (m, 2H). MS (+ESI) m/z 571.20 (MH⁺).

Example 4

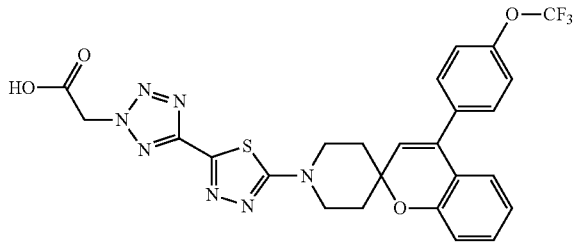 [SMILES: O=C(O)Cn1nnc(-c2nnc(N3CCC4(C=C(c5ccc(OC(F)(F)F)cc5)c5ccccc5O4)CC3)s2)n1]

(5-{5-[4-(2-Chlorophenyl)-1'H-spiro[chromene-2,4'-piperidin]-1'-yl]-1,3,4-thiadiazol-2-yl}-2H-tetrazol-2-yl)acetic acid Step 1: Ethyl[5-(5-{4-[4-(trifluoromethoxy)phenyl]-1'H-spiro[chromene-2,4'-piperidin]-1'-yl}-1,3,4-thiadiazol-2-yl)-2H-tetrazol-2-yl]acetate The title compound was prepared in a similar manner as that described for Example 2 (Step 1) from 4-[4-(trifluoromethoxy)-phenyl]spiro [chromene-2,4'-piperidine]hydrochloride and Intermediate 2.

Step 2: (5-{5-[4-(2-Chlorophenyl)-1'H-spiro[chromene-2,4'-piperidin]-1'-yl]-1,3,4-thiadiazol-2-yl}-2H-tetrazol-2-yl)acetic acid The title compound was prepared in a similar manner as that described for Example 1 (Step 3) from ethyl [5-(5-{-4-[4-(trifluoromethoxy)phenyl]-1'H-spiro [chromene-2,4'-piperidin]-1'-yl}-1,3,4-thiadiazol-2-yl)-2H-tetrazol-2-yl]acetate and LiOH at room temperature. ¹H NMR (500 MHz, DMSO-d₆): δ 7.51 (d, 2H), 7.46 (d, 2H), 7.28-7.24 (m, 1H), 7.05 (d, 1H), 6.98-6.94 (m, 2H), 5.94 (s, 1H), 5.83 (s, 2H), 3.90 (d, 2H), 3.76-3.70 (m, 2H), 2.09-1.98 (m, 4H). MS (+ESI) m/z 572.1 (MH+).

Example 5

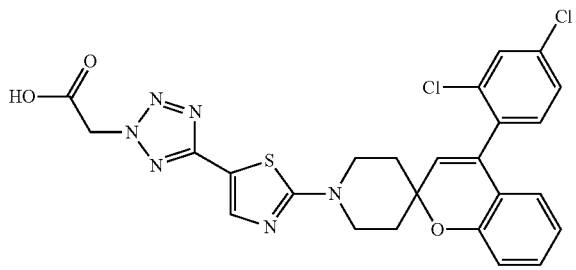

(5-{2-[4-(2,4-Dichlorophenyl)-1'H-spiro[chromene-2,4'-piperidin]-1'-yl]-1,3-thiazol-5-yl}-2H-tetrazol-2-yl)acetic acid Step 1: 4-(2,4-Dichlorophenyl)spiro[chromene-2,4'-piperidine]hydrochloride The title compound was prepared in a similar manner as that described for Example 1 (Step 1) from Intermediate 3 and (2,4-dichlorophenyl)boronic acid.

Step 2: tert-Butyl(5-{2-[4-(2,4-dichlorophenyl)-1'H-spiro[chromene-2,4'-piperidin]-1'-yl]-1,3-thiazol-5-yl}-2H-tetrazol-2-yl)acetate The title compound was prepared in a similar manner as that described for Example 1 (Step 2) from 4-(2,4-dichlorophenyl)spiro[chromene-2,4'-piperidine]hydrochloride and Intermediate 1.

Step 3: (5-{2-[4-(2,4-Dichlorophenyl)-1'H-spiro[chromene-2,4'-piperidin]-1'-yl]-1,3-thiazol-5-yl}-2H-tetrazol-2-yl)acetic acid The title compound was prepared in a similar manner as that described for Example 1 (Step 3) from tert-butyl(5-{2-[4-(2,4-dichlorophenyl)-1'H-spiro-[chromene-2,4'-piperidin]-1'-yl]-1,3-thiazol-5-yl}-2H-tetrazol-2-yl)acetate and LiOH at room temperature. $^1$H NMR (500 MHz, DMSO-$d_6$): δ 7.89 (s, 1H), 7.76 (d, 1H), 7.54 (dd, 1H), 7.40 (d, 1H), 7.01 (d, 1H), 6.86 (s, 1H), 6.55 (d, 1H), 5.86 (s, 1H), 5.67 (s, 2H), 3.86 (s, 2H), 3.65-3.59 (m, 2H), 2.13-2.06 (m, 2H), 2.00-1.93 (m, 2H). MS (+ESI) m/z 555.0 (MH+).

Example 6

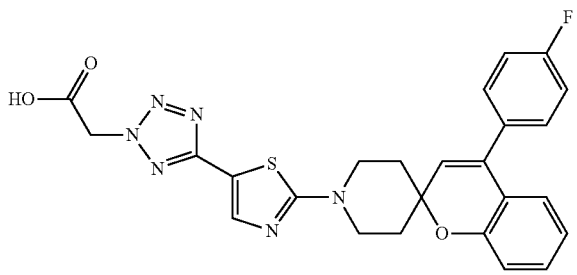 [SMILES: O=C(O)Cn1nnc(-c2cnc(N3CCC4(C=C(c5ccc(F)cc5)c5ccccc5O4)CC3)s2)n1]

2-(5-(2-(4-(4-Fluorophenyl)spiro[chromene-2,4'-piperidine]-1'-yl)thiazol-5-yl)-2H-tetrazol-2-yl)acetic acid Step 1 tert-Butyl-4-(4-fluorophenyl)spiro[chromene-2,4'-piperidine]-1'-carboxylate The title compound was prepared in a similar manner as that described for Example 1 (step 1) from Intermediate 3 and (4-fluorophenyl)boronic acid.

Step 2 4-(4-Fluorophenyl)spiro[chromene-2,4'-piperidine] A solution of tert-butyl-4-(4-fluorophenyl)spiro[chromene-2,4'-piperidine]-1'-carboxylate (1.25 g, 3.17 mmol) in DCM (6 mL) and TFA (3 mL, 38.9 mmol) was stirred at 0° C. for 60 min. The reaction was diluted with DCM, washed with a mixture of 20% NaOH (30 mL) and brine. The organic layer was separated and dried over MgSO$_4$, filtered and concentrated under reduced pressure. Upon storage under high vacuum, the resulting oil turned a white solid characterized as the title compound.

Step 3 Ethyl 2-(5-(2-(4-(4-fluorophenyl)spiro[chromene-2,4'-piperidine]-1'-yl)thiazol-5-yl)-2H-tetrazol-2-yl)acetate In a pressure vial, a mixture of 4-(4-fluorophenyl)spiro[chromene-2,4'-piperidine] (128 mg, 0.433 mmol), Intermediate 4 (175 mg, 0.550 mmol) and K$_2$CO$_3$ (127 mg, 0.919 mmol) were suspended in dry DME (2 mL). The vial was sealed and the mixture was stirred under N$_2$ at an external temperature of 110° C. for 2 h. The reaction mixture was then cooled to room temperature, and diluted with DCM/methanol and concentrated under reduced pressure in the presence of silica gel. The resulting solid residue was purified by Combiflash™ chromatography (SiO$_2$ (12 g), eluting with 3-10% EtOAc/hexanes) to afford the title compound as a solid.

Step 4 2-(5-(2-(4-(4-Fluorophenyl)spiro[chromene-2,4'-piperidine]-1'-yl)thiazol-5-yl)-2H-tetrazol-2-yl)acetic acid A solution of ethyl 2-(5-(2-(4-(4-fluorophenyl)spiro[chromene-2,4'-piperidine]-1'-yl)thiazol-5-yl)-2H-tetrazol-2-yl)acetate (192 mg, 0.361 mmol) in THF (3 mL) and ethanol (1 mL), stirred at 0° C., was treated with a solution of sodium hydroxide (141 mg, 3.53 mmol) in water (2 mL). The reaction mixture was stirred at 0° C. for 2 h, then diluted with DCM, washed with a solution of 5% KHSO$_4$ in water, dried over MgSO$_4$, filtered and concentrated under reduced pressure. The resulting residue was purified by reverse phase chromatography to afford the title compound as a white solid. $^1$H NMR (500 MHz, DMSO-$d_6$): δ 7.89 (s, 1H), 7.41 (dd, 2H), 7.30-7.21 (m, 3H), 7.04 (d, 1H), 6.99-6.91 (m, 2H), 5.88 (s, 1H), 5.68 (s, 2H), 3.86 (d, 2H), 3.66-3.56 (m, 2H), 2.10-2.02 (m, 2H), 2.00-1.90 (m, 2H). MS (+ESI) m/z 505.10 (MH+).

Example 7

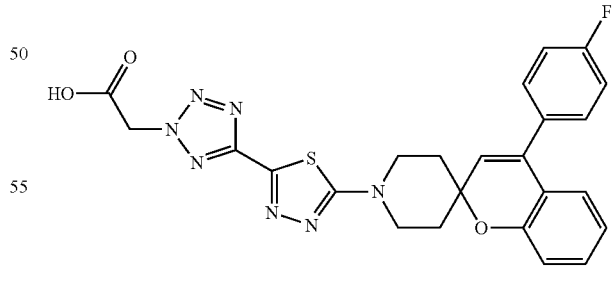

2-(5-(5-(4-(4-Fluorophenyl)spiro[chromene-2,4'-piperidine]-1'-yl)-1,3,4-thiadiazol-2-yl)-2H-tetrazol-2-yl)acetic acid Step 1: Ethyl 2-(5-(5-(4-(4-fluorophenyl)spiro[chromene-2,4'-piperidine]-1'-yl)-1,3,4-thiadiazol-2-yl)-2H-tetrazol-2-yl)acetate A mixture of 4-(4-fluorophenyl)spiro[chromene-2, 4'-piperidine] (171 mg, 0.58 mmol) (Example 6, Step 2), Intermediate 2 (203 mg, 0.64 mmol) and $K_2CO_3$ (144 mg, 1.04 mmol) was suspended in dry DME (3 mL). The reaction mixture was stirred under $N_2$ at an external temperature of 81° C. for 1.5 h. Then the reaction mixture was cooled down to room temperature, diluted with DCM (5 mL), washed with 5% $KHSO_4$ (10 mL), dried over $MgSO_4$, filtered and concentrated under reduced pressure. The resulting oily residue was purified by Combiflash™ chromatography ($SiO_2$ (12 g), eluting with 10-60% EtOAc/hexanes) to afford the title compound as an oil.

Step 2: 2-(5-(5-(4-(4-Fluorophenyl)spiro[chromene-2,4'-piperidine]-1'-yl)-1,3,4-thiadiazol-2-yl)-2H-tetrazol-2-yl) acetic acid The title compound was prepared in a similar manner as that described for Example 6 (step 4) from ethyl 2-(5-(5-(4-(4-fluorophenyl)-spiro[chromene-2,4'-piperidine]-1'-yl)-1,3,4-thiadiazol-2-yl)-2H-tetrazol-2-yl)acetate and NaOH at 0° C. $^1$H NMR (500 MHz, DMSO-$d_6$): δ 7.41 (t, 2H), 7.32-7.21 (m, 3H), 7.04 (d, 1H), 6.99-6.91 (m, 2H), 5.88 (s, 1H), 5.83 (s, 2H), 3.89 (d, 2H), 3.72 (t, 2H), 2.07 (d, 2H), 2.00 (t, 2H). MS (+ESI) m/z 506.1 (MH$^+$).

Examples 8-28 in Table 1 were prepared according to the procedures of Examples 1-7.

TABLE 1

| Example | Structure | Characterisation by Mass Spectrometry |
|---------|-----------|---------------------------------------|
| 8 | 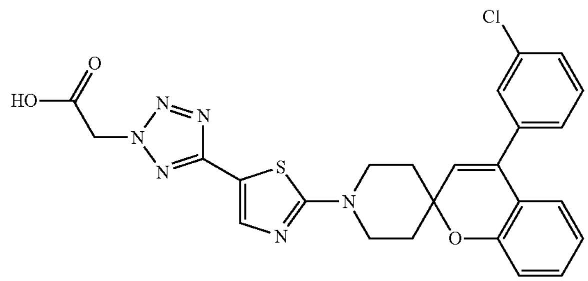 [SMILES: O=C(O)Cn1nnc(-c2cnc(N3CCC4(C=C(c5cccc(Cl)c5)c5ccccc5O4)CC3)s2)n1] | MS: m/z 521.0 (MH+) |
| 9 | 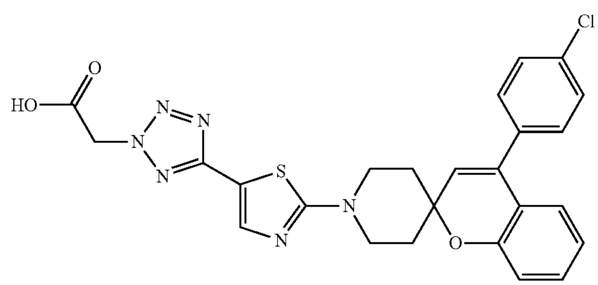 [SMILES: O=C(O)Cn1nnc(-c2cnc(N3CCC4(C=C(c5ccc(Cl)cc5)c5ccccc5O4)CC3)s2)n1] | MS: m/z 521.0 (MH+) |
| 10 | 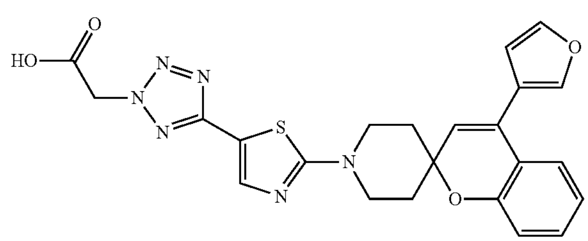 [SMILES: O=C(O)Cn1nnc(-c2cnc(N3CCC4(C=C(c5ccoc5)c5ccccc5O4)CC3)s2)n1] | MS: m/z 477.2 (MH+) |
| 11 | 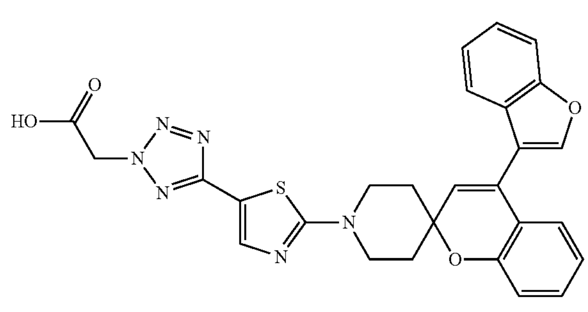 [SMILES: O=C(O)Cn1nnc(-c2cnc(N3CCC4(C=C(c5coc6ccccc56)c5ccccc5O4)CC3)s2)n1] | MS: m/z 527.2 (MH+) |

TABLE 1-continued
| Example | Structure | Characterisation by Mass Spectrometry |
|---|---|---|
| 12 | 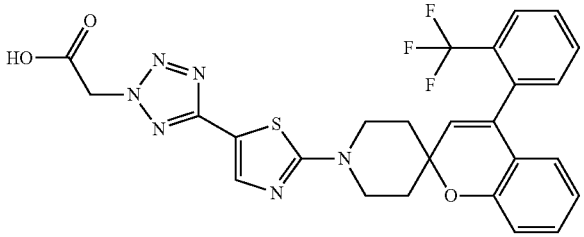 [SMILES: O=C(O)Cn1nnc(-c2cnc(N3CCC4(C=C(c5ccccc5C(F)(F)F)c5ccccc5O4)CC3)s2)n1] | MS: m/z 555.1 (MH+) |
| 13 | 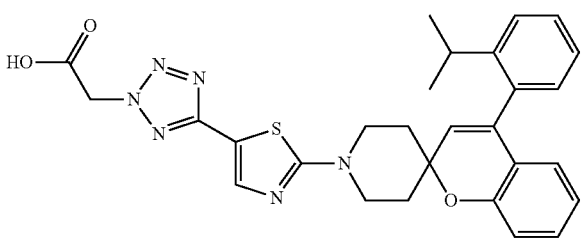 [SMILES: CC(C)c1ccccc1C1=CC2(CCN(c3ncc(-c4nnn(CC(=O)O)n4)s3)CC2)Oc2ccccc21] | MS: m/z 529.1 (MH+) |
| 14 | 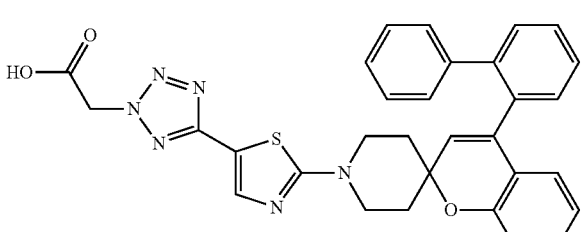 | MS: m/z 563.2 (MH+) |
| 15 | 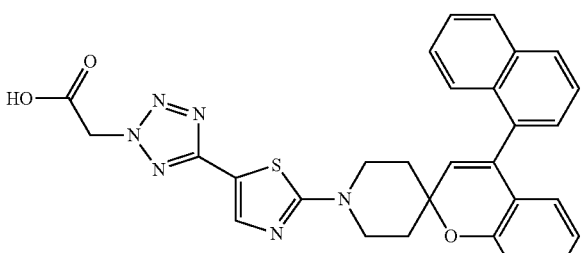 | MS: m/z 537.2 (MH+) |
| 16 | 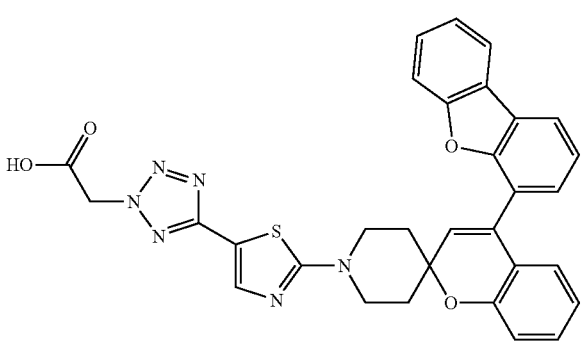 [SMILES: O=C(O)Cn1nnc(-c2cnc(N3CCC4(C=C(c5cccc6c5oc5ccccc56)c5ccccc5O4)CC3)s2)n1] | MS: m/z 577.2 (MH+) |

TABLE 1-continued
| Example | Structure | Characterisation by Mass Spectrometry |
|---|---|---|
| 17 | 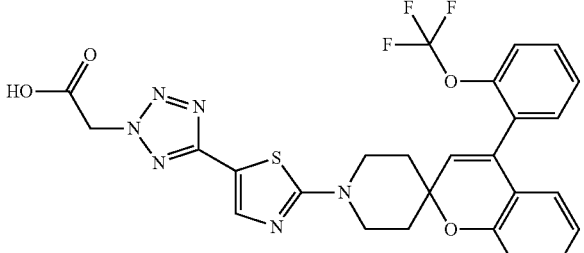 | MS: m/z 571.0 (MH+) |
| 18 | 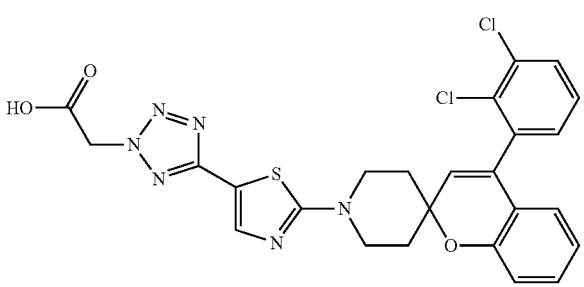 | MS: m/z 555.0 (MH+) |
| 19 | 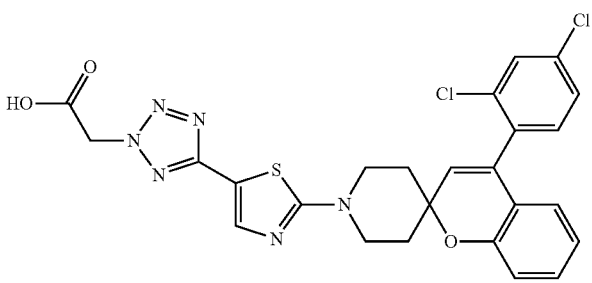 [SMILES: O=C(O)Cn1nnc(-c2cnc(N3CCC4(C=C(c5ccc(Cl)cc5Cl)c5ccccc5O4)CC3)s2)n1] | MS: m/z 555.0 (MH+) |
| 20 | 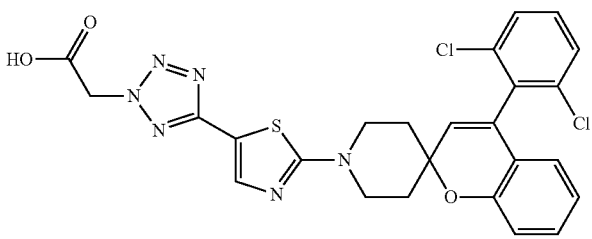 [SMILES: O=C(O)Cn1nnc(-c2cnc(N3CCC4(C=C(c5c(Cl)cccc5Cl)c5ccccc5O4)CC3)s2)n1] | MS: m/z 555.0 (MH+) |
| 21 | 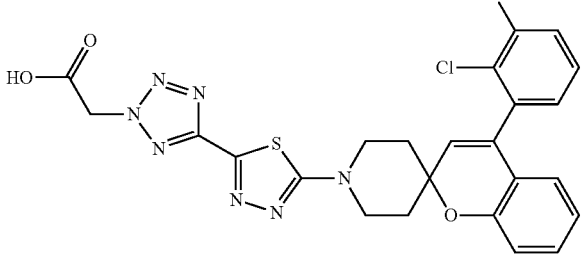 | MS: m/z 556.0 (MH+) |

TABLE 1-continued

| Example | Structure | Characterisation by Mass Spectrometry |
|---|---|---|
| 22 | 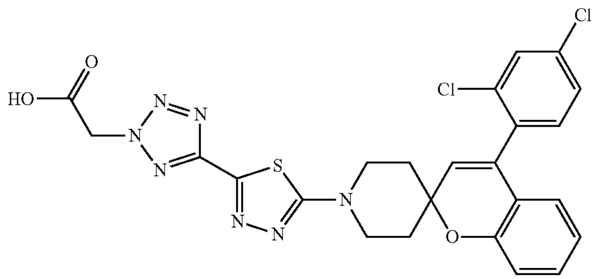 | MS: m/z 556.0 (MH+) |
| 23 | 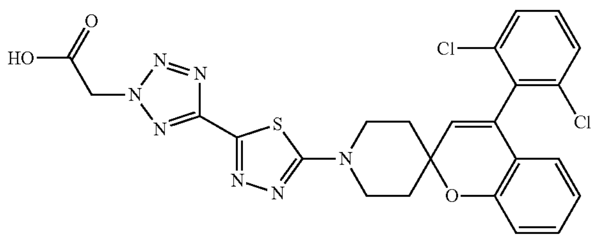 | MS: m/z 556.0 (MH+) |
| 24 | 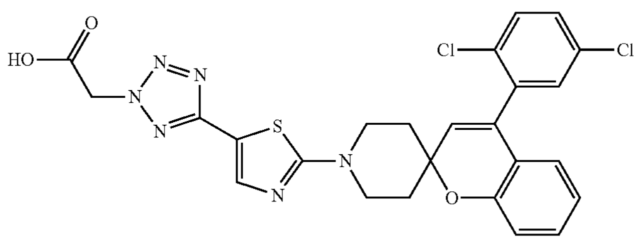 | MS: m/z 555.0 (MH+) |
| 25 | 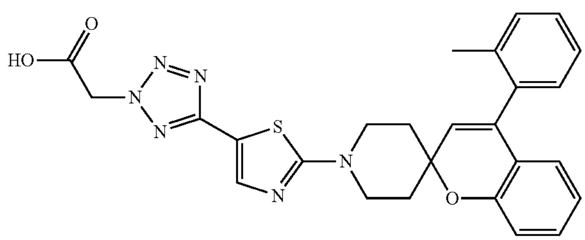 [SMILES: Cc1ccccc1C1=CC2(CCN(c3ncc(-c4nnn(CC(=O)O)n4)s3)CC2)Oc2ccccc21] | MS: m/z 501.0 (MH+) |
| 26 | 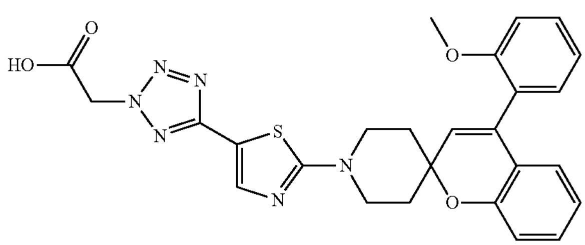 [SMILES: COc1ccccc1C1=CC2(CCN(c3ncc(-c4nnn(CC(=O)O)n4)s3)CC2)Oc2ccccc21] | MS: m/z 517.0 (MH+) |
| 27 | 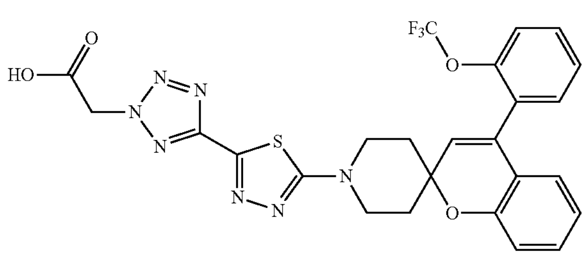 [SMILES: O=C(O)Cn1nnc(-c2nnc(N3CCC4(C=C(c5ccccc5OC(F)(F)F)c5ccccc5O4)CC3)s2)n1] | MS: m/z 572.2 (MH+) |

TABLE 1-continued

| Example | Structure | Characterisation by Mass Spectrometry |
|---|---|---|
| 28 | 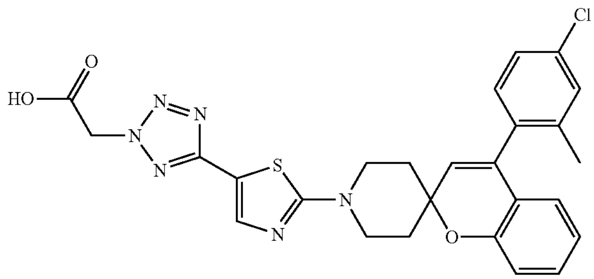 [SMILES: Cc1cc(Cl)ccc1C1=CC2(CCN(c3ncc(-c4nnn(CC(=O)O)n4)s3)CC2)Oc2ccccc21] | MS: m/z 535.0 (MH+) |
| 29 | 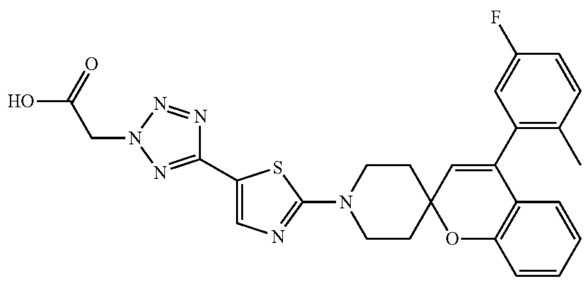 [SMILES: Cc1ccc(F)cc1C1=CC2(CCN(c3ncc(-c4nnn(CC(=O)O)n4)s3)CC2)Oc2ccccc21] | MS: m/z 519.1 (MH+) |
| 30 | 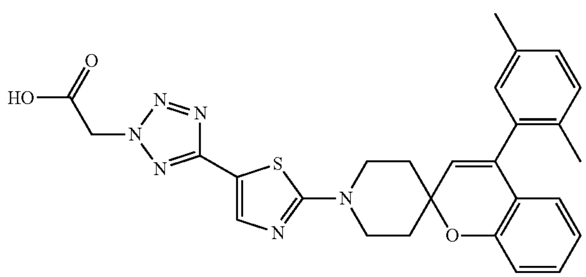 [SMILES: Cc1ccc(C)c(C2=CC3(CCN(c4ncc(-c5nnn(CC(=O)O)n5)s4)CC3)Oc3ccccc32)c1] | MS: m/z 515.1 (MH+) |
| 31 | 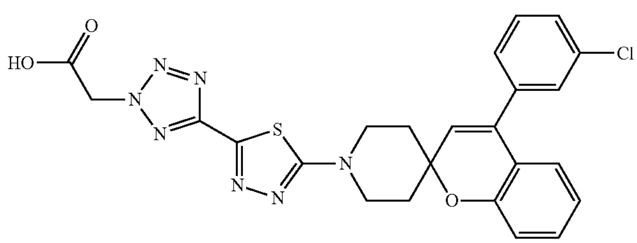 [SMILES: O=C(O)Cn1nnc(-c2nnc(N3CCC4(C=C(c5cccc(Cl)c5)c5ccccc5O4)CC3)s2)n1] | MS: m/z 522.1 (MH+) |

Example 32

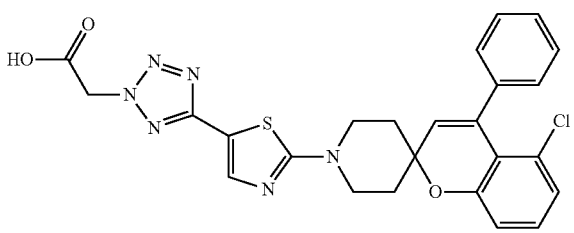 [SMILES: O=C(O)Cn1nnc(-c2cnc(N3CCC4(C=C(c5ccccc5)c5c(Cl)cccc5O4)CC3)s2)n1]

{5-[2-(5-Chloro-4-phenyl-1'H-spiro[chromene-2,4'-piperidin]-1'-yl)-1,3-thiazol-5-yl]-2H-tetrazol-2-yl}acetic acid Step 1: tert-Butyl 5-chloro-4-phenyl-1'H-spiro[chromene-2,4'-piperidine]-1'-carboxylate To a degassed solution of Intermediate 5 (100 mg, 0.21 mmol) in toluene (3 mL) was added phenyl boronic acid (33 mg, 0.21 mmol), $K_2CO_3$ (57 mg, 0.41 mmol), LiCl (25 mg, 0.58 mmol) and $Pd(PPh_3)_4$ (25 mg, 0.02 mmol). The resulting mixture was stirred at 90° C. for 12 hours, then cooled to room temperature, quenched with water (10 mL) and extracted with EtOAc (3×5 mL). The combined organic layers were washed with brine (10 mL), dried over $Na_2SO_4$ and concentrated under reduced pressure. The resulting residue was purified by preparative-TLC (Petroleum Ether/Ethyl Acetate=5/1) to afford the title compound.

Step 2: 5-Chloro-4-phenylspiro[chromene-2,4'-piperidine] To a solution of tert-butyl 5-chloro-4-phenyl-1'-spiro[chromene-2,4'-piperidine]-1'-carboxylate (55 g, 0.13 mmol) in dioxane (1 mL) was added HCl/dioxane (1 mL, 4 mmol). The reaction mixture was stirred at room temperature for 3 h. The reaction mixture was then concentrated under reduced pressure to afford the title compound.

Step 3: tert-Butyl {5-[2-(5-chloro-4-phenyl-1'H-spiro[chromene-2,4'-piperidin]-1'-yl)-1,3-thiazol-5-yl]-2H-tetrazol-2-yl}acetate To a solution of 5-chloro-4-phenylspiro[chromene-2,4'-piperidine] (50 mg, 0.13 mmol) and Intermediate 1 (44 mg, 0.13 mmol) in DMF (2 mL) was added $K_2CO_3$ (53 mg, 0.39 mmol). The reaction mixture was stirred at 60° C. for 10 h. After cooling to room temperature, the reaction mixture was diluted with water (10 mL) and extracted with EtOAc (2×10 mL). The combined organic layers were washed with brine (10 mL), dried over $Na_2SO_4$ and concentrated under reduced pressure. The resulting residue was purified by preparative TLC (Petroleum Ether/Ethyl Acetate=3:1) to afford the title compound.

Step 4: {5-[2-(5-Chloro-4-phenyl-1'H-spiro[chromene-2,4'-piperidin]-1'-yl)-1,3-thiazol-5-yl]-2H-tetrazol-2-yl}acetic acid To a solution of tert-butyl{5-[2-(5-chloro-4-phenyl-1'H-spiro[chromene-2,4'-piperidin]-1'-yl)-1,3-thiazol-5-yl]-2H-tetrazol-2-yl}acetate (50 mg, 0.09 mmol) in dioxane (1 mL) was added HCl/dioxane (1 mL, 4 mmol). The reaction mixture was stirred at room temperature for 3 h, then concentrated under reduced pressure to afford the title compound. $^1$H NMR (DMSO-$d_6$ 400 MHz) δ 7.76 (m, 1H), 6.98-7.32 (m, 8H), 5.95 (s, 1H), 4.90 (s, 2H), 3.51-3.78 (m, 4H), 1.93-1.96 (m, 4H). MS (+ESI) m/z 521.1 (MH$^+$).

Examples 33-42 in Table 2 were prepared according to the procedure of Example 32.

TABLE 2

| Example | Structure | Characterisation by Mass Spectrometry |
|---|---|---|
| 33 | 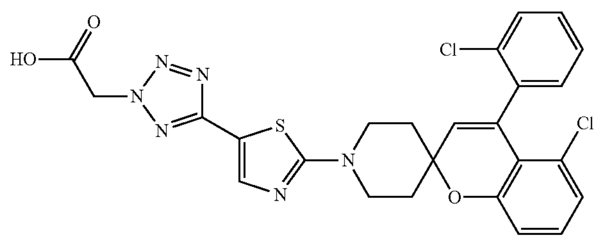 [SMILES: O=C(O)Cn1nnc(-c2cnc(N3CCC4(C=C(c5ccccc5Cl)c5c(Cl)cccc5O4)CC3)s2)n1] | MS: m/z 555.0 (MH+) |
| 34 | 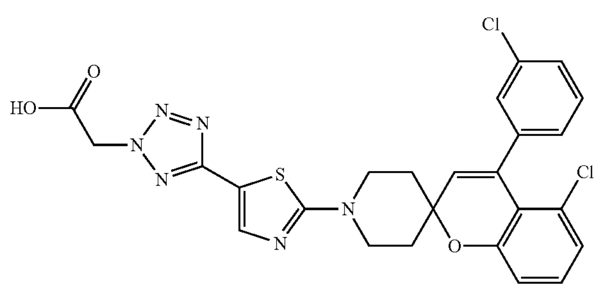 [SMILES: O=C(O)Cn1nnc(-c2cnc(N3CCC4(C=C(c5cccc(Cl)c5)c5c(Cl)cccc5O4)CC3)s2)n1] | MS: m/z 555.0 (MH+) |
| 35 | 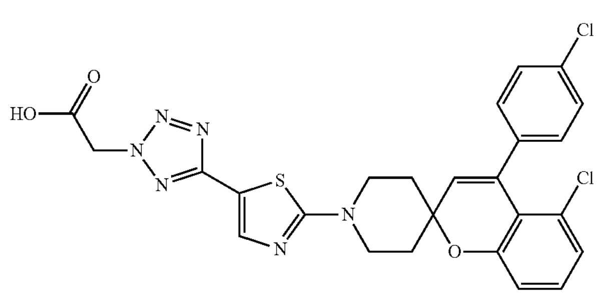 [SMILES: O=C(O)Cn1nnc(-c2cnc(N3CCC4(C=C(c5ccc(Cl)cc5)c5c(Cl)cccc5O4)CC3)s2)n1] | MS: m/z 555.0 (MH+) |
| 36 | 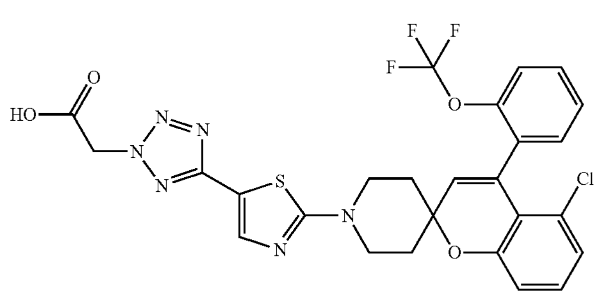 [SMILES: O=C(O)Cn1nnc(-c2cnc(N3CCC4(C=C(c5ccccc5OC(F)(F)F)c5c(Cl)cccc5O4)CC3)s2)n1] | MS: m/z 604.1 (MH+) |

TABLE 2-continued

| Example | Structure | Characterisation by Mass Spectrometry |
|---|---|---|
| 37 | 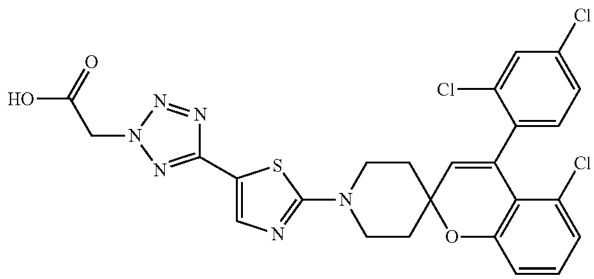 [SMILES: O=C(O)Cn1nnc(-c2cnc(N3CCC4(C=C(c5ccc(Cl)cc5Cl)c5c(Cl)cccc5O4)CC3)s2)n1] | MS: m/z 588.9 (MH+) |
| 38 | 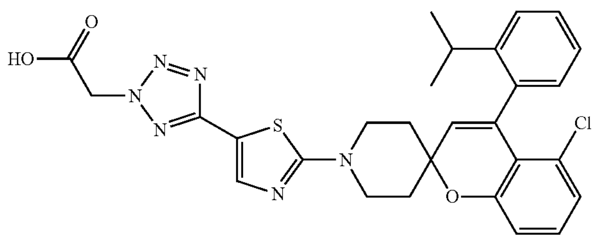 [SMILES: CC(C)c1ccccc1C1=CC2(CCN(c3ncc(-c4nnn(CC(=O)O)n4)s3)CC2)Oc2cccc(Cl)c21] | MS: m/z 563.1 (MH+) |
| 39 | 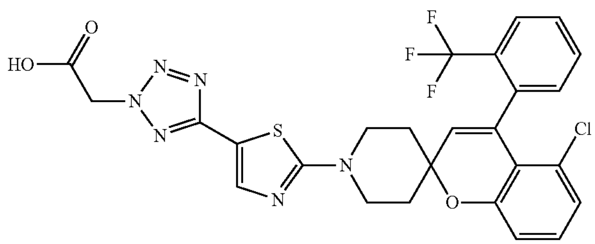 [SMILES: O=C(O)Cn1nnc(-c2cnc(N3CCC4(C=C(c5ccccc5C(F)(F)F)c5c(Cl)cccc5O4)CC3)s2)n1] | MS: m/z 589.1 (MH+) |
| 40 | 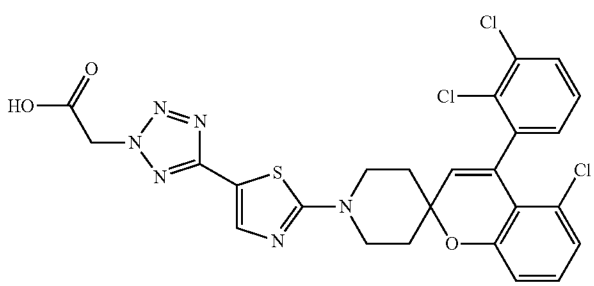 [SMILES: O=C(O)Cn1nnc(-c2cnc(N3CCC4(C=C(c5cccc(Cl)c5Cl)c5c(Cl)cccc5O4)CC3)s2)n1] | MS: m/z 589.1 (MH+) |
| 41 | 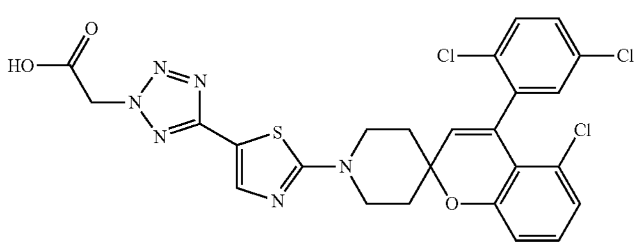 [SMILES: O=C(O)Cn1nnc(-c2cnc(N3CCC4(C=C(c5cc(Cl)ccc5Cl)c5c(Cl)cccc5O4)CC3)s2)n1] | MS: m/z 589.0 (MH+) |
| 42 | 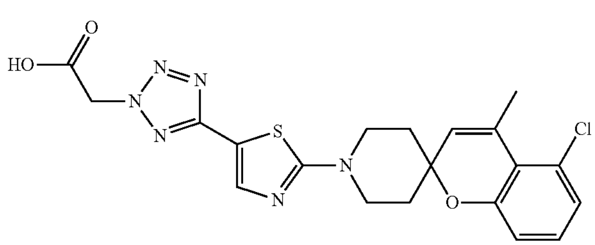 [SMILES: CC1=CC2(CCN(c3ncc(-c4nnn(CC(=O)O)n4)s3)CC2)Oc2cccc(Cl)c21] | MS: m/z 458.1 (MH+) |

Example 42 was prepared according to the procedure of Example 32 with Step 1 being replaced by Step 1 of Example 43.

Example 43

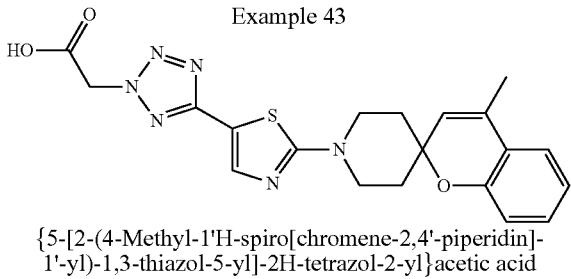

{5-[2-(4-Methyl-1'H-spiro[chromene-2,4'-piperidin]-1'-yl)-1,3-thiazol-5-yl]-2H-tetrazol-2-yl}acetic acid Step 1: 4-Methylspiro[chromene-2,4'-piperidine]hydrochloride To a degassed solution of Intermediate 3 (302 mg, 0.67 mmol) in THF (3.7 mL) and water (0.56 mL) was added potassium methyltrifluoroborate (78 mg, 0.64 mmol), PdCl$_2$(dppf)-CH$_2$Cl$_2$ (78 mg, 0.096 mmol) and cesium carbonate (521 mg, 1.60 mmol). The mixture was stirred at reflux for 16 h in a sealed tube. Then the volatiles were evaporated under reduced pressure. The residue was diluted with water (10 mL)/1N HCl (10 mL) and extracted with EtOAc (3×5 mL). The combined organic layers were dried, filtered and evaporated under reduced pressure, and the resulting residue was purified by Combiflash™ chromatography (SiO$_2$ (12 g), eluting with 0-30% EtOAc/hexanes over 40 min). The resulting intermediate was diluted with 4 N HCl in dioxane (5 mL) and placed in a round bottom flask equipped with a condenser. The mixture was heated periodically (every 10 min) to reflux using a heat gun for a total of 30 min. Then the volatiles were evaporated under reduced pressure to afford the title compound as a solid.

Step 2: tert-Butyl {5-[2-(4-methyl-1'H-spiro[chromene-2,4'-piperidin]-1'-yl)-1,3-thiazol-5-yl]-2H-tetrazol-2-yl}acetate The title compound was prepared in a similar manner as that described for Example 1 Step 2) from 4-methylspiro[chromene-2,4'-piperidine]hydrochloride and Intermediate 1.

Step 3: {5-[2-(4-Methyl-1'H-spiro[chromene-2,4'-piperidin]-1'-yl)-1,3-thiazol-5-yl]-2H-tetrazol-2-yl}acetic acid The title compound was prepared in a similar manner as that described for Example 1 (Step 3) from tert-butyl{5-[2-(4-methyl-1'H-spiro[chromene-2,4'-piperidin]-1'-yl)-1,3-thiazol-5-yl]-2H-tetrazol-2-yl}acetate and LiOH at room temperature. $^1$H NMR (500 MHz, DMSO-d$_6$): δ 7.87 (s, 1H), 7.24 (d, 2H), 7.19 (t, 2H), 6.95 (t, 2H), 6.91 (d, 2H), 5.65 (s, 4H), 5.63 (s, 2H), 3.82 (d, 4H), 3.55 (t, 4H), 2.01 (d, 5H), 1.96 (d, 3H), 1.83 (t, 4H). MS (+ESI) m/z 425.20 (MH$^+$).

Example 44

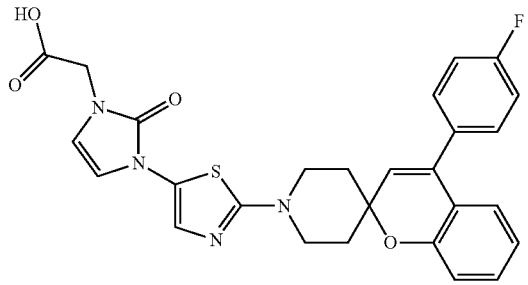 [SMILES: O=C(O)Cn1ccn(-c2cnc(N3CCC4(C=C(c5ccc(F)cc5)c5ccccc5O4)CC3)s2)c1=O]

2-(3-(2-(4-(4-Fluorophenyl)spiro[chromene-2,4'-piperidine]-1'-yl)thiazol-5-yl)-2-oxo-2,3-dihydro-1H-imidazol-1-yl)acetic acid Step 1: Ethyl N-{[(2,2-dimethoxyethyl)amino]carbonyl}glycinate To a solution of ethyl isocyanatoacetate (8.84 mL, 77 mmol) in CH$_2$Cl$_2$ (100 mL) at 0° C. was added amino-acetaldehyde dimethyl acetal (8.86 mL, 81 mmol) over a period of 10 min. The mixture was then stirred for 30 min and quenched with water. The CH$_2$Cl$_2$ layer was separated, washed with water, dried (Na$_2$SO$_4$) and concentrated to give the crude title compound as an oil.

Step 2: Ethyl (2-oxo-2,3-dihydro-1H-imidazol-1-yl)acetate To a solution of ethyl N-{[(2,2-dimethoxyethyl)amino]carbonyl}glycinate (16 g, 68.3 mmol) in acetic acid (20 mL) was added 80% aqueous formic acid (80 mL, 1669 mmol). The reaction mixture was stirred at 65° C. for 1 h. Then the reaction mixture was concentrated in vacuo. The resulting residue was diluted with small amount of water (~10 to 20 mL) and extracted with EtOAc (3×50 mL). The combined EtOAc extracts were concentrated and dried under reduced pressure. The resulting residue was triturated with Et$_2$O to give the title compound as a pale yellow solid.

Step 3 1'-(5-Bromothiazol-2-yl)-4-(4-fluorophenyl)spiro[chromene-2,4'-piperidine] In a pressure vial, a mixture of 4-(4-fluorophenyl)spiro[chromene-2,4'-piperidine] (233 mg, 0.79 mmol), 2,5-dibromothiazole (279 mg, 1.15 mmol) and K$_2$CO$_3$ (190 mg, 1.38 mmol) was suspended in dry DME (3.5 mL). The reaction mixture was stirred under N$_2$ atmosphere at an external temperature of 110° C. for 2 h. The reaction mixture was allowed to warm up to room temperature, then diluted with DCM, and concentrated in the presence of silica gel. The resulting solid residue was purified by Combiflash™ chromatography (SiO$_2$ (12 g), eluting with 1.5-25% EtOAc/hexanes) to afford the title compound as a foam.

Step 4 Ethyl 2-(3-(2-(4-(4-fluorophenyl)spiro[chromene-2,4'-piperidine]-1'-yl)thiazol-5-yl)-2-oxo-2,3-dihydro-1H-imidazol-1-yl)acetate A mixture of 1'-(5-bromothiazol-2-yl)-4-(4-fluorophenyl)spiro[chromene-2,4'-piperidine] (93.2 mg, 0.20 mmol), ethyl (2-oxo-2,3-dihydro-1H-imidazol-1-yl)acetate (Example 38, Step 2) (52 mg, 0.31 mmol), copper (I) iodide (39 mg, 0.21 mmol) and K$_3$PO$_4$ (105 mg, 0.49 mmol) was suspended in dry dioxane (2 mL). The reaction mixture was stirred under vacuum for 3 min, then the reaction mixture was backfilled with N$_2$, treated with neat N1,N2-dimethylethane-1,2-diamine (22.9 mg, 0.26 mmol), covered with aluminum foil and stirred in an oil bath preheated at 94° C. for 3.5 h. The reaction mixture was then diluted with DCM (3 mL), washed with saturated NH$_4$Cl (10 mL), 5% KHSO$_4$ (10 mL), dried over MgSO$_4$, filtered and concentrated under reduced pressure. The resulting oily residue was purified by Combiflash™ chromatography (SiO$_2$ (12 g), eluting with 5-70% EtOAc/hexanes) to afford the title compound as a foam.

Step 5 2-(3-(2-(4-(4-Fluorophenyl)spiro[chromene-2,4'-piperidine]-1'-yl)thiazol 5-yl)-2-oxo-2,3-dihydro-1H-imidazol-1-yl)acetic acid The title compound was prepared in a similar manner as that described for Example 6 (step 4) from ethyl 2-(3-(2-(4-(4-fluorophenyl)spiro[chromene-2,4'-piperidine]-1'-yl)thiazol-5-yl)-2-oxo-2,3-dihydro-1H-imidazol-1-yl)acetate and NaOH at 0° C. $^1$H NMR (500 MHz, DMSO-d$_6$): δ 7.41 (dd, 2H), 7.31-7.20 (m, 4H), 7.03-6.89 (m, 4H), 6.78 (d, 1H), 5.87 (s, 1H), 4.35 (s, 2H), 3.71 (d, 2H), 3.48 (t, 2H), 2.01 (d, 2H), 1.96-1.86 (m, 2H). MS (+ESI) m/z 519.1 (MH+).

Example 45

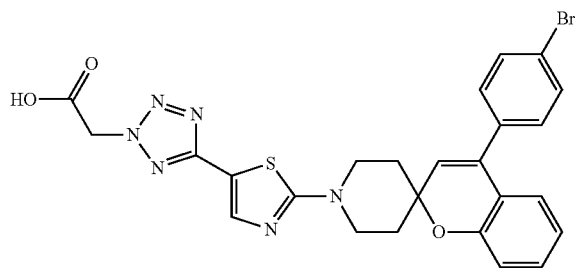

(5-{2-[4-(4-Bromophenyl)-1'H-spiro[chromene-2,4'-piperidin]-1'-yl]-1,3-thiazol-5-yl}-2H-tetrazol-2-yl)acetic acid Step 1: tert-Butyl 4-(4,4,5,5-tetramethyl-1,3,2-dioxaborolan-2-yl)-1'H-spiro[chromene-2,4'-piperidine]-1'-carboxylate To a degassed solution of Intermediate 3 (2 g, 4.45 mmol) in dioxane (11.1 ml) was added 4,4,4',4',5,5,5',5'-octamethyl-2,2'-bi-1,3,2-dioxaborolane (1.695 g, 6.67 mmol), potassium acetate (0.568 g, 5.78 mmol) and PdCl$_2$(dppf)-CH$_2$Cl$_2$ adduct (0.182 g, 0.22 mmol). The reaction mixture was heated to 85° C. and stirred for 16 h. The volatiles were evaporated under reduced pressure and the residue was purified by Combiflash™ chromatography (SiO$_2$ (12 g), eluting with 0-40% EtOAc/hexanes) to afford the title compound Step 2: 4-(4-Bromophenyl)spiro[chromene-2,4'-piperidine]hydrochloride The title compound was prepared in a similar manner as that described for Example 1, Step 1 from tert-butyl 4-(4,4,5,5-tetramethyl-1,3,2-dioxaborolan-2-yl)-1'H-spiro[chromene-2,4'-piperidine]-1'-carboxylate and 1,4-dibromobenzene.

Step 3: (5-{2-[4-(4-Bromophenyl)-1'H-spiro[chromene-2,4'-piperidin]-1'-yl]-1,3-thiazol-5-yl}-2H-tetrazol-2-yl)acetic acid The title compound was prepared in a similar manner as that described for Example 1, Steps 2 and 3 from 4-(4-bromophenyl)spiro[chromene-2,4'-piperidine]hydrochloride and Intermediate 1. $^1$H NMR (500 MHz, DMSO-d$_6$): δ 7.89 (s, 1H), 7.65 (d, 2H), 7.33 (d, 2H), 7.27-7.23 (m, 1H), 7.04 (d, 1H), 6.99-6.93 (m, 2H), 5.92 (s, 1H), 5.70 (s, 2H), 3.86 (d, 2H), 3.64-3.58 (m, 2H), 2.05 (d, 2H), 1.99-1.94 (m, 2H). MS (+ESI) m/z 565.0/567.0 (MH+).

Example 46

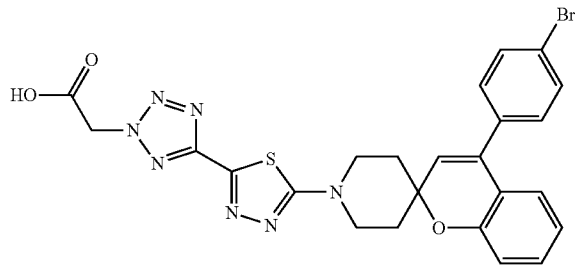 [SMILES: O=C(O)Cn1nnc(-c2nnc(N3CCC4(C=C(c5ccc(Br)cc5)c5ccccc5O4)CC3)s2)n1]

(5-{5-[4-(4-Bromophenyl)-1'H-spiro[chromene-2,4'-piperidin]-1'-yl]-1,3,4-thiadiazol-2-yl}-2H-tetrazol-2-yl)acetic acid Step 1: (5-{5-[4-(4-Bromophenyl)-1'H-spiro[chromene-2,4'-piperidin]-1'-yl]-1,3,4-thiadiazol-2-yl}-2H-tetrazol-2-yl) acetic acid The title compound was prepared in a similar manner as that described for Example 2, Steps 1 and 2 from 4-(4-bromophenyl)spiro[chromene-2,4'-piperidine]hydrochloride and Intermediate 2. $^1$H NMR (500 MHz, DMSO-d$_6$): δ 7.66 (d, 2H), 7.33 (d, 2H), 7.28-7.23 (m, 1H), 7.05 (d, 1H), 6.99-6.91 (m, 2H), 5.92 (s, 1H), 5.82 (s, 2H), 3.88 (s, 2H), 3.72 (t, 2H), 2.07-1.99 (m, 4H). MS (+ESI) m/z 566.0/568.0 (MH+).

Example 47

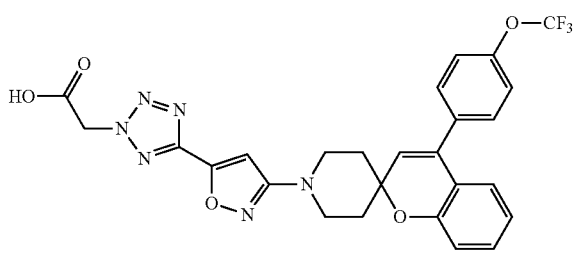 [SMILES: O=C(O)Cn1nnc(-c2cc(N3CCC4(C=C(c5ccc(OC(F)(F)F)cc5)c5ccccc5O4)CC3)no2)n1]

[5-(3-{4-[4-(Trifluoromethoxy)phenyl]-1'H-spiro[chromene-2,4'-piperidin]-1'-yl}isoxazol-5-yl)-2H-tetrazol-2-yl]acetic acid Step 1: tert-Butyl[5-(3-{4-[4-(trifluoromethoxy)phenyl]-3,4-dihydro-1'H-spiro[chromene-2,4'-piperidin]-1'-yl}-4,5-dihydroisoxazol-5-yl)-2H-tetrazol-2-yl]acetate To a solution of Intermediate 6 (325 mg, 0.978 mmol) and 4-[4-(trifluoromethoxy)phenyl]spiro[chromene-2,4'-piperidine]hydrochloride (428 mg, 1.076 mmol) (Example 3, step 1) in t-BuOH (4892 µl) was added sodium bicarbonate (247 mg, 2.94 mmol). The reaction mixture was directly warmed to 115° C. and stirred for 16 h. Then the reaction mixture was diluted with MTBE and poured into water/1N HCl (20 mL) and extracted with EtOAc (3×5 mL). The combined organic layers were dried (MgSO$_4$), filtered and evaporated under reduced pressure. The residue was purified by Combiflash™ chromatography (SiO$_2$ (12 g), eluting with 25-80% EtOAc/hexanes) to afford the title compound.

Step 2: tert-Butyl [5-(3-{4-[4-(trifluoromethoxy)phenyl]-3,4-dihydro-1'H-spiro[chromene-2,4'-piperidin]-1'-yl}isoxazol-5-yl)-2H-tetrazol-2-yl]acetate To a solution of tert-butyl [5-(3-{4-[4-(trifluoromethoxy)phenyl]-3,4-dihydro-1'H-spiro[chromene-2,4'-piperidin]-1'-yl}-4,5-dihydroisoxazol-5-yl)-2H-tetrazol-2-yl]acetate (98 mg, 0.160 mmol) in pyridine (1.5 ml, 18.55 mmol) was added I$_2$ (60.9 mg, 0.240 mmol). The reaction mixture was heated to 110° C. and stirred for 20 h. The reaction was diluted with water/1N HCl (10 mL) and extracted with EtOAc (3×3 mL). The combined organic layers were dried filtered and evaporated under reduced pressure. The residue was purified by Combiflash™ chromatography (SiO$_2$ (12 g), eluting with 10-70% EtOAc/hexanes) to afford the title compound as a solid.

Step 3: 5-(3-{4-[4-(Trifluoromethoxy)phenyl]-1'H-spiro[chromene-2,4'-piperidin]-1'-yl}isoxazol-5-yl)-2H-tetrazol-2-yl]acetic acid The title compound was prepared in a similar manner as that described for Example 1 (Step 3) from tert-butyl [5-(3-{4-[4-(trifluoromethoxy)phenyl]-3,4-dihydro-1'H-spiro[chromene-2,4'-piperidin]-1'-yl}isoxazol-5-yl)-2H-tetrazol-2-yl]acetate and LiOH at room temperature. ¹H NMR (500 MHz, DMSO-d₆): δ 7.50 (d, 2H), 7.45 (d, 2H), 7.28 (s, 1H), 7.25 (t, 1H), 7.03 (d, 1H), 6.97-6.90 (m, 2H), 5.93 (s, 1H), 5.84 (s, 2H), 3.66 (d, 2H), 3.44 (d, 2H), 2.00-1.87 (m, 4H). MS (+ESI) m/z 555.4 (MH⁺).

Example 48

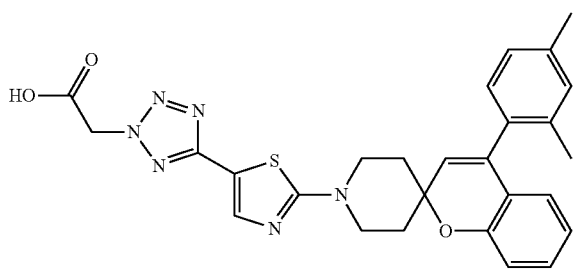 [SMILES: Cc1ccc(C2=CC3(CCN(c4ncc(-c5nnn(CC(=O)O)n5)s4)CC3)Oc3ccccc32)c(C)c1]

(5-{2-[4-(2,4-Dimethylphenyl)-1'H-spiro[chromene-2,4'-piperidin]-1'-yl]-1,3-thiazol-5-yl}-2H-tetrazol-2-yl)acetic acid Step 1: (5-{2-[4-(2,4-Dimethylphenyl)-1'H-spiro[chromene-2,4'-piperidin]-1'-yl]-1,3-thiazol-5-yl}-2H-tetrazol-2-yl)acetic acid The title compound was prepared in a similar manner as that described for Example 1, Steps 1 and 3 from (4-chloro-2-methylphenyl)boronic acid and Intermediate 7. ¹H NMR (500 MHz, DMSO-d₆): δ 7.88 (s, 1H), 7.18 (t, 1H), 7.12 (s, 1H), 7.07 (d, 1H), 7.00 (dd, 2H), 6.83 (t, 1H), 6.52 (d, 1H), 5.67 (s, 3H), 3.87 (d, 2H), 3.62 (t, 2H), 2.32 (s, 3H), 2.27-2.14 (m, 2H) 2.08 (s, 3H), 2.04-1.87 (m, 2H). MS (+ESI) m/z 515.1 (MH⁺).

Examples 49-65 in Table 3 were prepared according to the procedure of Example 48.

TABLE 3

| Example | Structure | Characterisation by Mass Spectrometry |
|---|---|---|
| 49 | ![structure] | MS: m/z 505.1 (MH+) |
| 50 | ![structure] | MS: m/z 515.1 (MH+) |
| 51 | ![structure] | MS: m/z 535.0 (MH+) |

TABLE 3-continued
| Example | Structure | Characterisation by Mass Spectrometry |
|---|---|---|
| 52 | 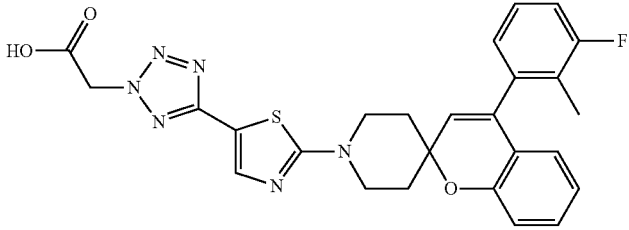 [SMILES: Cc1c(F)cccc1C1=CC2(CCN(c3ncc(-c4nnn(CC(=O)O)n4)s3)CC2)Oc2ccccc21] | MS: m/z 519.1 (MH+) |
| 53 | 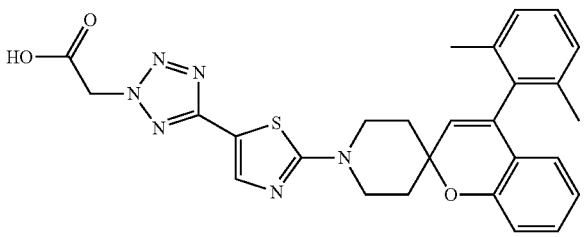 | MS: m/z 515.1 (MH+) |
| 54 | 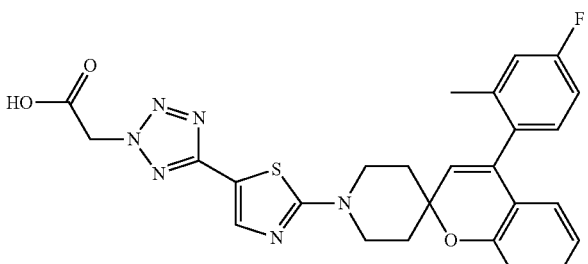 | MS: m/z 519.1 (MH+) |
| 55 | 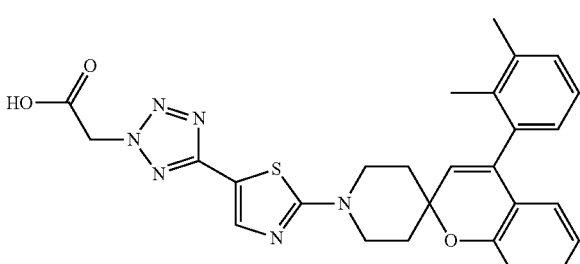 | MS: m/z 515.1 (MH+) |
| 56 | 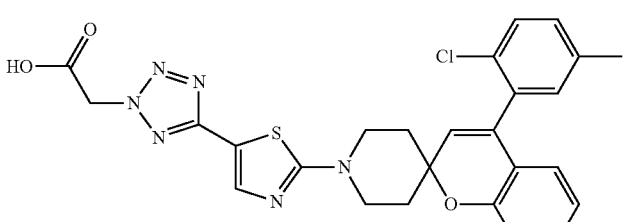 | MS: m/z 535.0 (MH+) |
| 57 | 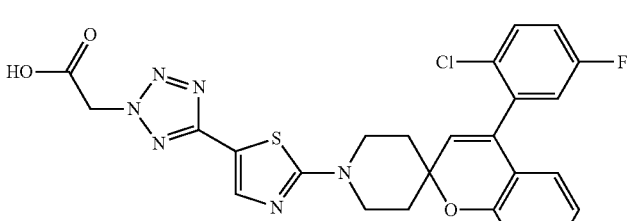 | MS: m/z 539.1 (MH+) |

TABLE 3-continued
| Example | Structure | Characterisation by Mass Spectrometry |
|---|---|---|
| 58 | 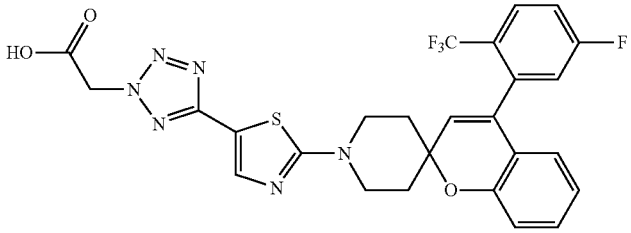 [SMILES: O=C(O)Cn1nnc(-c2cnc(N3CCC4(C=C(c5cc(F)ccc5Cl)c5ccccc5O4)CC3)s2)n1] | MS: m/z 573.1 (MH+) |
| 59 | 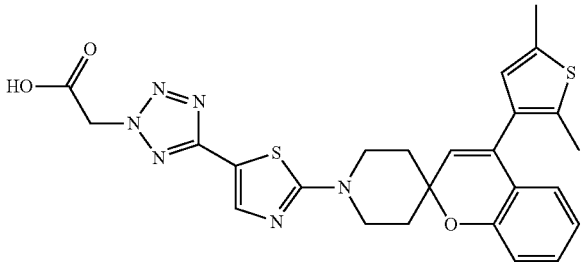 [SMILES: Cc1cc(C2=CC3(CCN(c4ncc(-c5nnn(CC(=O)O)n5)s4)CC3)Oc3ccccc32)c(C)s1] | MS: m/z 521.1 (MH+) |
| 60 | 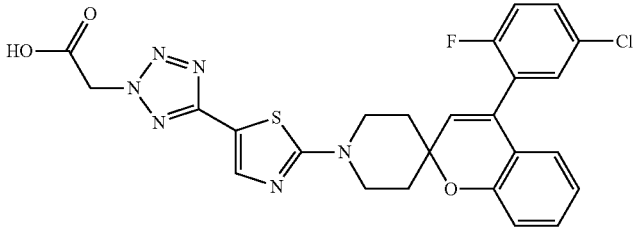 | MS: m/z 539.1 (MH+) |
| 61 | 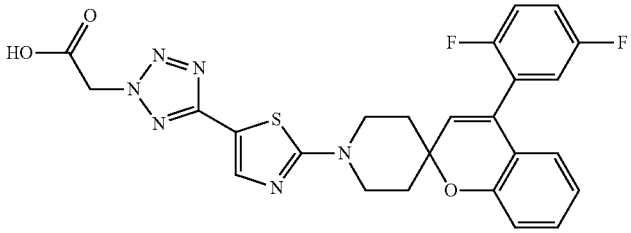 [SMILES: O=C(O)Cn1nnc(-c2cnc(N3CCC4(C=C(c5cc(F)ccc5F)c5ccccc5O4)CC3)s2)n1] | MS: m/z 523.0 (MH+) |
| 62 | 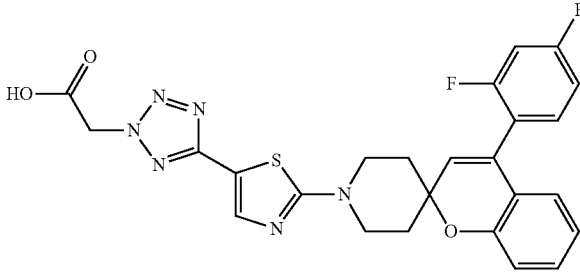 | MS: m/z 523.0 (MH+) |
| 63 | 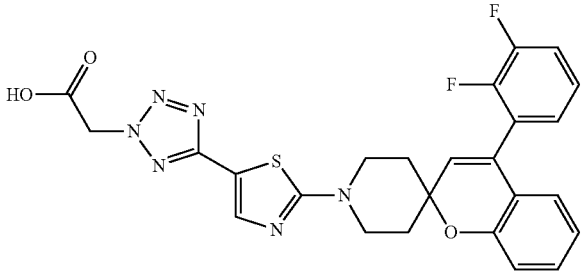 [SMILES: O=C(O)Cn1nnc(-c2cnc(N3CCC4(C=C(c5cccc(F)c5F)c5ccccc5O4)CC3)s2)n1] | MS: m/z 523.0 (MH+) |

TABLE 3-continued

| Example | Structure | Characterisation by Mass Spectrometry |
|---|---|---|
| 64 | 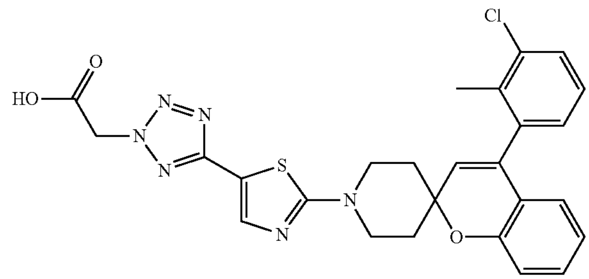 [SMILES: Cc1c(Cl)cccc1C1=CC2(CCN(c3ncc(-c4nnn(CC(=O)O)n4)s3)CC2)Oc2ccccc21] | MS: m/z 535.0 (MH+) |
| 65 | 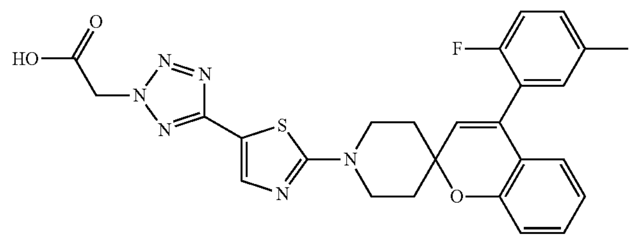 | MS: m/z 519.1 (MH+) |

What is claimed is:

1. A compound of structural formula I:

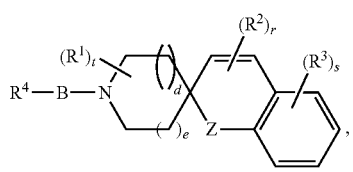

or a pharmaceutically acceptable salt thereof, wherein

Z is independently selected from the group consisting of: S, S(O), S(O)$_2$, O, NH and CH$_2$, wherein each NH is unsubstituted or substituted with R$^g$, and wherein CH$_2$ is unsubstituted or substituted with R$^2$;

B is a 5 membered heteroaryl ring containing 1, 2 or 3 heteroatoms selected from NH, O and S, wherein any CH is unsubstituted or substituted with one substituent selected from R$^a$, and wherein any NH is unsubstituted or substituted with one substituent selected from R$^b$;

each R$^1$ is independently selected from the group consisting of: hydrogen, halogen, and C$_{1-3}$ alkyl, wherein alkyl is unsubstituted or substituted with one to three substituents independently selected from halogen and hydroxy;

each R$^2$ is independently selected from the group consisting of:
(1) hydrogen,
(2) halogen,
(3) aryl,
(4) heteroaryl,
(5) biphenyl,
(6) C$_{1-6}$ alkyl,
(7) (CH$_2$)$_n$OR$^e$,
(8) (CH$_2$)$_n$N(R$^e$)$_2$,
(9) (CH$_2$)$_n$C≡N,
(10) (CH$_2$)$_n$COR$^e$, and
(11) (CH$_2$)$_n$S(O)$_q$R$^e$, wherein CH$_2$, alkyl, phenyl, aryl and heteroaryl are unsubstituted or substituted with one to three substituents independently selected from R$^f$;

each R$^3$ is independently selected from the group consisting of:
(1) hydrogen,
(2) halogen,
(3) —C$_{1-6}$ alkyl,
(4) —OC$_{1-6}$ alkyl,
(5) (CH$_2$)$_n$OR$^e$,
(6) (CH$_2$)$_n$N(R$^e$)$_2$,
(7) (CH$_2$)$_n$C≡N,
(8) (CH$_2$)$_n$COR$^e$, and
(9) (CH$_2$)$_n$S(O)$_q$R$^e$, wherein alkyl is unsubstituted or substituted with hydroxy or one to three halogens, and wherein any CH$_2$ in R$^3$ is unsubstituted or substituted with one to two groups independently selected from halogen, hydroxy, and C$_{1-4}$ alkyl unsubstituted or substituted with one to five fluorines;

R$^4$ is selected from the group consisting of:

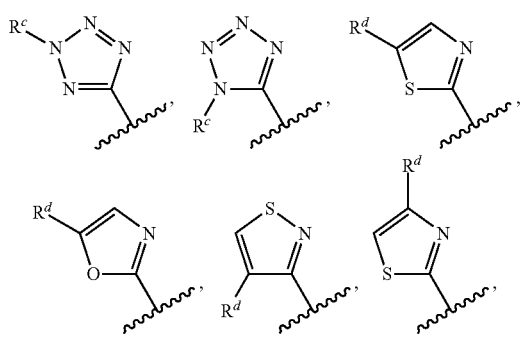

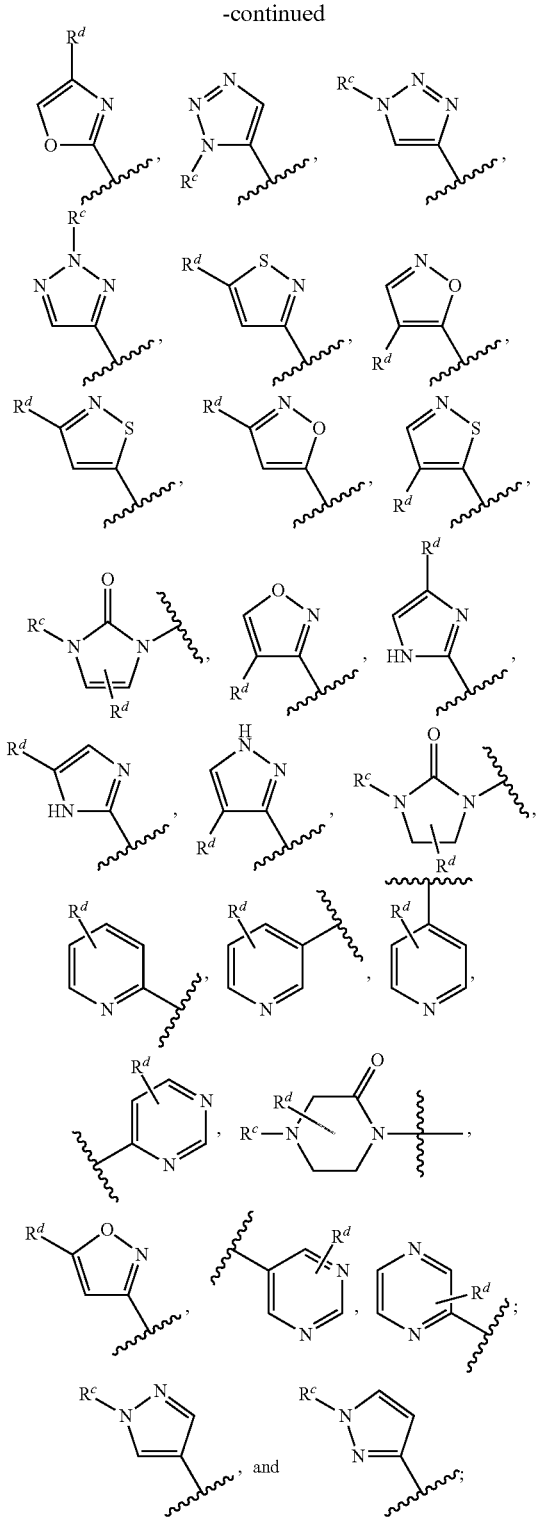

each $R^a$ is independently selected from the group consisting of:
(1) hydrogen,
(2) halogen,
(3) cyano,
(4) $C_{1-4}$ alkyl, unsubstituted or substituted with one to five fluorines,
(5) $C_{1-4}$ alkoxy, unsubstituted or substituted with one to five fluorines,
(6) $C_{1-4}$ alkylthio, unsubstituted or substituted with one to five fluorines,
(7) $C_{1-4}$ alkylsulfonyl,
(8) —$CO_2H$,
(9) $C_{1-4}$ alkyloxycarbonyl, and
(10) $C_{1-4}$ alkylcarbonyl;

each $R^b$ is independently selected from the group consisting of:
(1) hydrogen, and
(2) $C_{1-4}$ alkyl,
wherein alkyl is unsubstituted or substituted with one to five fluorines;

each $R^c$ is independently selected from the group consisting of:
(1) —$(CH_2)_m CO_2H$,
(2) —$(CH_2)_m CO_2 C_{1-3}$ alkyl,
(3) —$(CH_2)_m$—$NR^b$—$(CH_2)_p CO_2H$,
(4) —$(CH_2)_m$—$NR^b$—$(CH_2)_p CO_2 C_{1-3}$ alkyl,
(5) —$(CH_2)_m$—O—$(CH_2)_p CO_2H$,
(6) —$(CH_2)_m$—O—$(CH_2)_p CO_2 C_{1-3}$ alkyl,
(7) —$(CH_2)_m$—S—$(CH_2)_p CO_2H$, and
(8) —$(CH_2)_m$—S—$(CH_2)_p CO_2 C_{1-3}$ alkyl,
wherein any $CH_2$ in $R^c$ is unsubstituted or substituted with one to two groups independently selected from halogen, hydroxy, and $C_{1-4}$ alkyl unsubstituted or substituted with one to five fluorines;

each $R^d$ is independently selected from the group consisting of:
(1) —$(CH_2)_n CO_2H$,
(2) —$(CH_2)_n CO_2 C_{1-3}$ alkyl,
(3) —$(CH_2)_n$—$NR^b$—$(CH_2)_p CO_2H$,
(4) —$(CH_2)_n$—$NR^b$—$(CH_2)_p CO_2 C_{1-3}$ alkyl,
(5) —$(CH_2)_n$—O—$(CH_2)_p CO_2H$,
(6) —$(CH_2)_n$—O—$(CH_2)_p CO_2 C_{1-3}$ alkyl,
(7) —$(CH_2)_n$—S—$(CH_2)_p CO_2H$, and
(8) —$(CH_2)_n$—S—$(CH_2)_p CO_2 C_{1-3}$ alkyl,
wherein any $CH_2$ in $R^d$ is unsubstituted or substituted with one to two groups independently selected from the group consisting of: halogen, hydroxy, and $C_{1-4}$ alkyl unsubstituted or substituted with one to five fluorines;

each $R^e$ is independently selected from the group consisting of:
(1) hydrogen, and
(2) $C_{1-6}$ alkyl,
wherein alkyl is unsubstituted or substituted with one to three substituents independently selected from the group consisting of: halogen, cyano, —$C_{1-4}$ alkoxy, —$C_{1-4}$ alkylthio, —$C_{1-4}$ alkylsulfonyl, —$CO_2H$, and —$CO_2 C_{1-4}$ alkyl;

each $R^f$ is independently selected from the group consisting of:
(1) hydrogen,
(2) halogen,
(3) —$C_{1-6}$ alkyl,
(4) —$OC_{1-6}$ alkyl,
(5) $(CH_2)_n OR^e$,
(6) $(CH_2)_n N(R^e)_2$,
(7) $(CH_2)_n C\equiv N$,
(8) $(CH_2)_n COR^e$,
(9) $(CH_2)_n S(O)_q R^e$, and
(10) aryl,
wherein $CH_2$, alkyl and aryl are unsubstituted or substituted with one, two or three groups independently selected from halogen, hydroxy, and $C_{1-4}$ alkyl unsubstituted or substituted with one to five fluorines;

each $R^g$ is independently selected from the group consisting of:
(1) hydrogen, and
(2) $C_{1-6}$ alkyl;
m is an integer from 1 to 3;
n is an integer from 0 to 3;
p is an integer from 1 to 3;
q is an integer from 1 to 2;
r is an integer from 0 to 2;
s is an integer from 0 to 4;
t is an integer from 0 to 8;
d is an integer from 0 to 2; and
e is an integer from 0 to 2,
provided that d+e is 2.

2. The compound of claim 1 wherein Z is O; or a pharmaceutically acceptable salt thereof.

3. The compound of claim 2 wherein d is 1; e is 1; r is 1; s is 0, 1, 2 or 3; and t is 0; or a pharmaceutically acceptable salt thereof.

4. The compound of claim 3 wherein s is 0 or 1; or a pharmaceutically acceptable salt thereof.

5. The compound of claim 1 wherein $R^4$ is selected from the group consisting of:

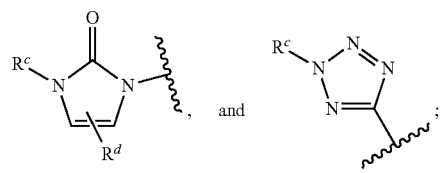

or a pharmaceutically acceptable salt thereof.

6. The compound of claim 5 wherein $R^4$ is

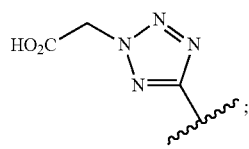 [SMILES: *c1nnn(CC(=O)O)n1]

or a pharmaceutically acceptable salt thereof.

7. The compound of claim 1 wherein B is selected from the group consisting of:

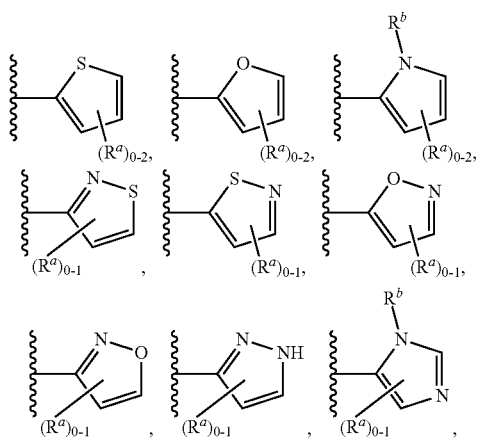

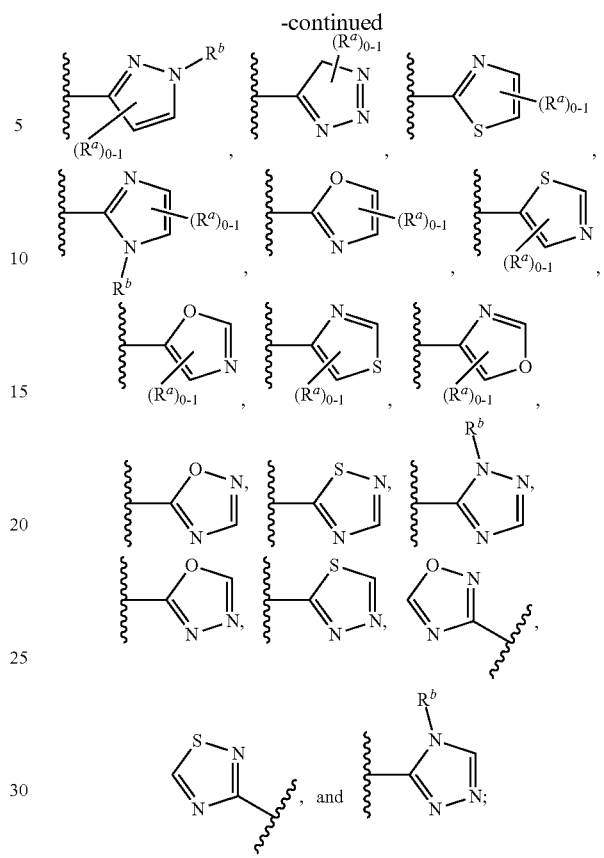

or a pharmaceutically acceptable salt thereof.

8. The compound of claim 7 wherein B is selected from the group consisting of:

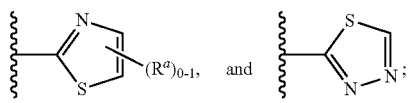

or a pharmaceutically acceptable salt thereof.

9. The compound of claim 8 wherein B is selected from the group consisting of:

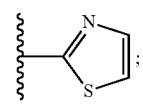

or a pharmaceutically acceptable salt thereof.

10. The compound of claim 1 wherein $R^2$ is independently selected from the group consisting of:
(1) aryl,
(2) heteroaryl,
(3) biphenyl, and
(4) —$C_{1-6}$ alkyl, wherein alkyl, biphenyl, aryl and heteroaryl are unsubstituted or substituted with one to three substituents independently selected from $R^f$; or a pharmaceutically acceptable salt thereof.

11. The compound of claim 1 wherein $R^2$ is phenyl, wherein phenyl is unsubstituted or substituted with one to three substituents independently selected from $R^f$;

or a pharmaceutically acceptable salt thereof.

12. The compound of claim 1 wherein:

Z is O;

B is selected from the group consisting of:

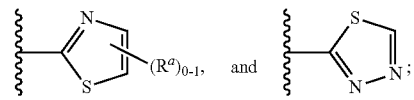

$R^2$ is independently selected from the group consisting of:
(1) aryl,
(2) heteroaryl,
(3) biphenyl, and
(4) —$C_{1-6}$ alkyl, wherein alkyl, biphenyl, aryl and heteroaryl are unsubstituted or substituted with one to three substituents independently selected from $R^f$;

$R^3$ is independently selected from the group consisting of: hydrogen and halogen;

$R^4$ is selected from the group consisting of:

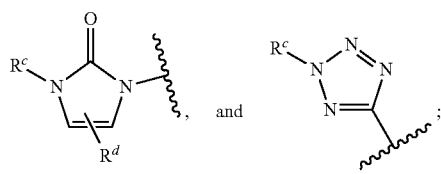

d is 1;
e is 1;
r is 1;
s is 0 or 1; and
t is 0;

or a pharmaceutically acceptable salt thereof.

13. The compound of claim 1 wherein:

Z is O;

B is selected from the group consisting of:

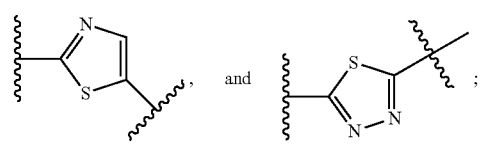 [SMILES: *c1cnc(*)s1 ; *c1nnc(*)s1]

$R^2$ is phenyl, wherein phenyl is unsubstituted or substituted with one to three substituents independently selected from $R^f$;

$R^3$ is independently selected from the group consisting of: hydrogen and halogen;

$R^4$ is

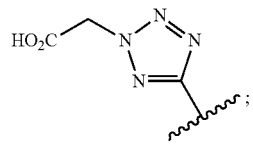 [SMILES: *c1nnn(CC(=O)O)n1]

d is 1;
e is 1;
r is 1;
s is 0 or 1; and
t is 0;

or a pharmaceutically acceptable salt thereof.

14. The compound of claim 13 selected from the group consisting of:

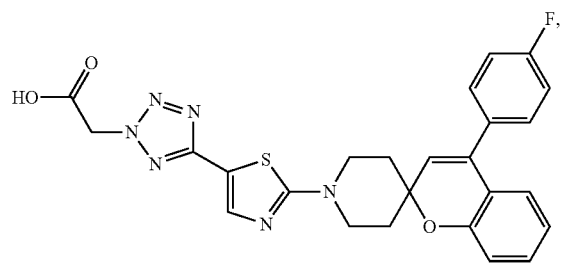

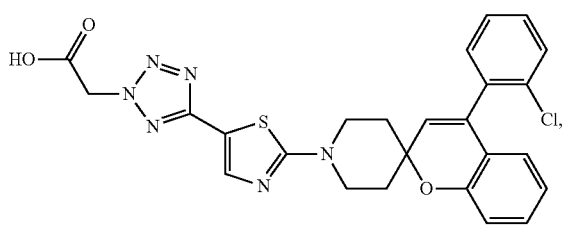

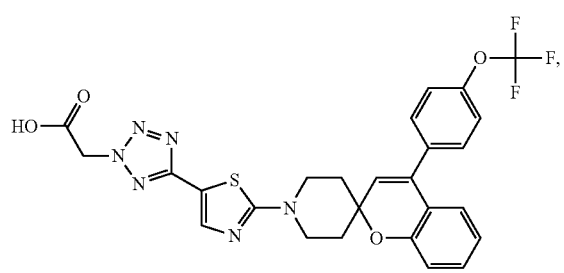

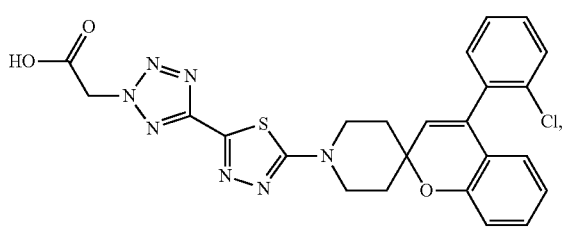

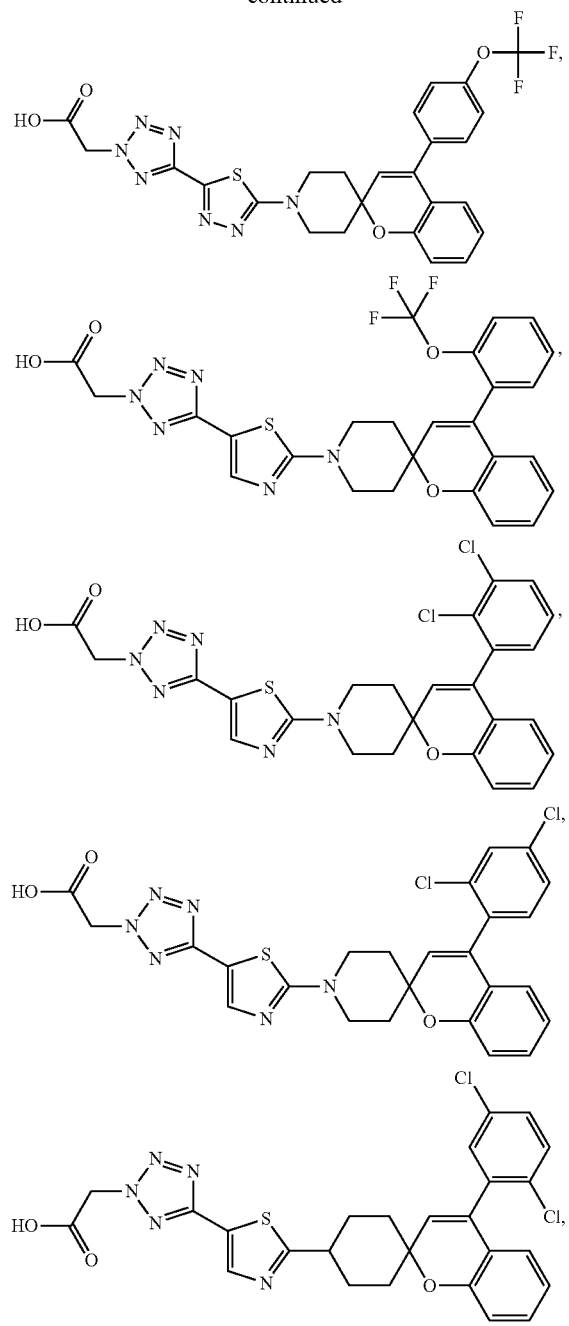

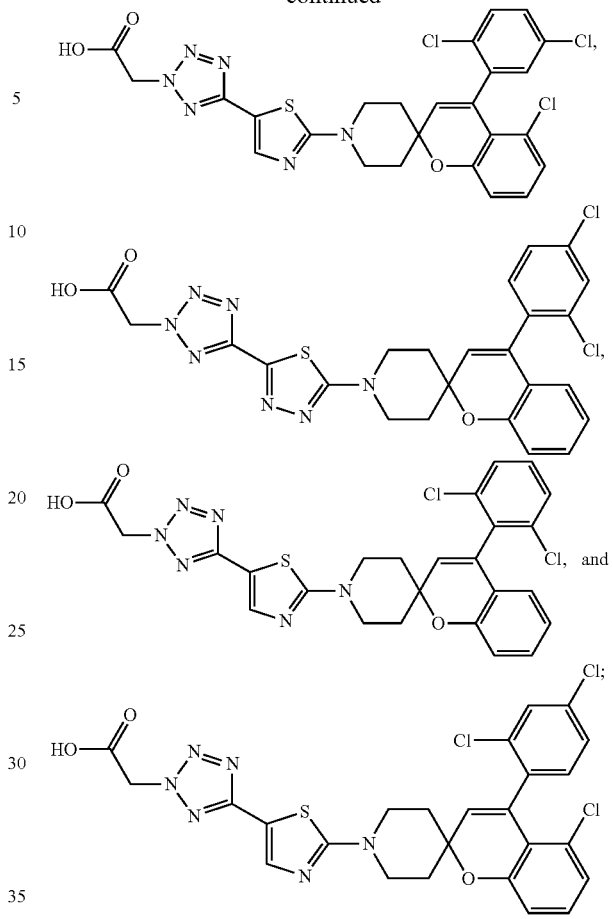

or a pharmaceutically acceptable salt thereof.

15. A pharmaceutical composition comprising a compound of claim 1 in combination with a pharmaceutically acceptable carrier.

16. A method of treating hyperglycemia, diabetes or insulin resistance in a mammal in need thereof which comprises the administration to the mammal of a therapeutically effective amount of a compound of claim 1.

17. A method of treating a lipid disorder selected from the group consisting of dyslipidemia, hyperlipidemia, hypertriglyceridemia, hypercholesterolemia, low HDL, and high LDL in a mammal in need thereof which comprises the administration to the mammal of a therapeutically effective amount of a compound of claim 1.

* * * * *